US012799503B2

(12) United States Patent
Beahm et al.

(10) Patent No.: US 12,799,503 B2
(45) Date of Patent: Nov. 17, 2026

(54) COMPOSITIONS AND METHODS FOR TREATING NGYL1 DEFICIENCY

(71) Applicant: GRACE SCIENCE, LLC, Menlo Park, CA (US)

(72) Inventors: Brendan Beahm, Union City, CA (US); Selina Dwight, Palo Alto, CA (US); William F. Mueller, Redwood City, CA (US); Thomas Wechsler, San Francisco, CA (US); Matt Wilsey, Menlo Park, CA (US); Lei Zhu, San Francisco, CA (US)

(73) Assignee: GRACE SCIENCE, LLC, Menlo Park, CA (US)

(*) Notice: Subject to any disclaimer, the term of this patent is extended or adjusted under 35 U.S.C. 154(b) by 393 days.

(21) Appl. No.: 18/557,194

(22) PCT Filed: Apr. 21, 2022

(86) PCT No.: PCT/US2022/025834
§ 371 (c)(1),
(2) Date: Oct. 25, 2023

(87) PCT Pub. No.: WO2022/231950
PCT Pub. Date: Nov. 3, 2022

(65) Prior Publication Data

US 2024/0218396 A1 Jul. 4, 2024

Related U.S. Application Data

(60) Provisional application No. 63/180,065, filed on Apr. 26, 2021.

(51) Int. Cl.

| | |
|---|---|
| ***C12N 15/86*** | (2006.01) |
| ***A61K 48/00*** | (2006.01) |
| ***A61P 43/00*** | (2006.01) |
| ***C12N 9/80*** | (2006.01) |

(52) U.S. Cl.
CPC .......... *C12N 15/86* (2013.01); *A61K 48/0008* (2013.01); *A61K 48/0058* (2013.01); *A61P 43/00* (2018.01); *C12N 9/80* (2013.01); *C12Y 305/01052* (2013.01)

(58) Field of Classification Search
CPC ..................................................... C12N 15/86
See application file for complete search history.

(56) References Cited

U.S. PATENT DOCUMENTS

| | | | |
|---|---|---|---|
| 5,399,363 A | 3/1995 | Liversidge | |
| 5,478,745 A | 12/1995 | Samulski | |
| 5,543,158 A | 8/1996 | Gref | |
| 5,552,157 A | 9/1996 | Yagi | |
| 5,565,213 A | 10/1996 | Nakamori | |
| 5,567,434 A | 10/1996 | Szoka, Jr. | |
| 5,641,515 A | 6/1997 | Ramtoola | |
| 5,656,016 A | 8/1997 | Ogden | |
| 5,697,899 A | 12/1997 | Hillman | |
| 5,738,868 A | 4/1998 | Shinkarenko | |
| 5,741,516 A | 4/1998 | Webb | |
| 5,770,219 A | 6/1998 | Chiang | |
| 5,779,708 A | 7/1998 | Wu | |
| 5,783,208 A | 7/1998 | Venkateshwaran | |
| 5,795,587 A | 8/1998 | Gao | |
| 5,797,898 A | 8/1998 | Santini, Jr. | |
| 5,871,982 A | 2/1999 | Wilson | |
| 6,001,650 A | 12/1999 | Colosi | |
| 6,083,716 A | 7/2000 | Wilson | |
| 6,156,303 A | 12/2000 | Russell | |
| 6,251,677 B1 | 6/2001 | Wilson | |
| 2017/0096683 A1* | 4/2017 | Scaria | A61P 27/06 |
| 2021/0139563 A1* | 5/2021 | Nolte | C07K 14/005 |

FOREIGN PATENT DOCUMENTS

| | | | |
|---|---|---|---|
| WO | 1998/10088 A1 | 3/1998 | |
| WO | WO-2020210592 A1 * | 10/2020 | A61K 31/713 |

OTHER PUBLICATIONS

Dabaj et al., "NGLY1 Deficiency: A Rare Newly Described Condition with a Typical Presentation". Life (Basel). Feb. 27, 2021;11(3): 187. (Year: 2021).*

Alberts, et al., "Molecular Biology of the Cell, Fifth Edition". New York:Garland Science, 2008. pp. 1-3 and 367 (Year: 2008).*

Zhou, X., et al., "Structural and biochemical studies of the C-terminal domain of mouse peptide-N-glycanase identify it as a mannose-bindingmodule," Proc. Natl. Acad. Sci. USA, 2006, 103(46): 17214-17219.

Zhu, J, et al., "Toll-like receptor 4 deficiency impairs motor coordination," Front. Neurosci. 2016, 10:33.

Zolgensma® (onasemnogene abeparvovec-xioi) USPI. Revised May 2019. AveXis, Inc. Bannockburn, IL, USA Accessed Jun. 2019.

Hinderer, C., et al., "Widespread gene transfer in the central nervous system of cynomolgus macaques following delivery of AAV9 into the cisterna magna," Molecular Therapy—Methods & Clinical Development, 1: 14051 (2014).

Hughes, M.P., et al., "AAV9 intracerebroventricular gene therapy improves lifespan, locomotor function and pathology in a mouse model of Niemann-Pick type C1 disease," Human Molecular Genetics, 27(17): 3079-3098 (2018).

Zhu, L., et al., AAV9-NGLY1 gene replacement therapy improves phenotypic and biomarker endpoints in a rat model of NGLY1 Deficiency, Molecular Therapy Methods & Clinical Development, 27: 259-271 (2022).

(Continued)

*Primary Examiner* — Christopher M Babic
*Assistant Examiner* — Hanan Isam Abuzeineh
(74) *Attorney, Agent, or Firm* — Ballard Spahr LLP

(57) ABSTRACT

Disclosed herein, are compositions and methods useful in expressing a functional NGLY1 protein in a subject by administration of an rAAV containing a transgene encoding NGLY1. Also disclosed herein are methods for treating an NGLY1 gene deficiency in a subject in need thereof.

13 Claims, 9 Drawing Sheets

Specification includes a Sequence Listing.

(56) References Cited

OTHER PUBLICATIONS

Abuduxikuer, K., et al., "Novel NGLYI gene variants in Chinese children with global developmental delay, microcephaly, hypotonia, hypertransaminasemia, alacrimia, and feeding difficulty," J. Hum. Genet., 2020, 65(4): 387-396.
Ahmed, SS, et al., "Sustained correction of a murine model of phenylketonuria following a single intravenous administration of AAVHSC15-PAH," Mol. Ther. Methods Clin. Dev., 2020, 17: 568-580.
Aiello-Laws, L., et al., "Management of adult patients receiving intraventricular chemotherapy for the treatment ofleptomeningeal metastasis," Clin J Oncol Nurs., 2008; 12(3): 429-35.
Arvio, M, et al., "Aspartylglycosaminuria: a review," Orphanet J Rare Dis., 2016; 11(1):162.
Asahina, M., et al., "Nglyl-/-rats develop neurodegenerative phenotypes and pathological abnormalities in their peripheral and central nervous systems," Hum. Mol. Genet., 2020, 29(10):1635-1647.
Asahina, et al., "Reversability of motor dysfunction in the rat model of NGLY1 deficiency," Mol. Brain, 2021, 14: 91 (pp. 1-12).
Atkinson, A.J., "Intracerebroventricular drug administration," Transl. Clin. Pharmacol., 2017, 25(3): 117-124.
Bailey, R.M., et al., "Development of intrathecal AAV9 gene therapy for giant axonal neuropathy," Mol. Ther. Methods Clin. Dev., 2018, 9:160-171.
Balwani, M., et al., "Phase 3 Trial of RNAi Therapeutic Givosiran for Acute Intermittent Porphyria," N. Engl. J. Med., 2020, 382(24): 2289-2301.
Bevan, A.K., et al., "Systemic gene delivery in large species for targeting spinal cord, brain, and peripheral tissues for pediatric disorders," Mol. Ther., 2011, 19(11): 1971-1980.
Bolon, B., et al., "STP position paper: recommended practices for sampling and processing the nervous system (brain, spinal cord, nerve, and eye) during nonclinical general toxicity studies," Toxicol. Pathol., 2013, 41(7): 1028-1048.
Bolon, B, et al., "STP position paper: recommended best practices for sampling, processing, and analysis of the peripheral nervous system (nerves and somatic and autonomic ganglia) during nonclinical toxicity studies," Toxicol. Pathol., Jun. 2018, 46(4): 372-402.
Caglayan, A.O., et al., "NGLYI mutation causes neuromotor impairment, intellectual disability, and neuropathy," Eur. J. Med. Genet., 2015, 58(1): 39-43.
Cahan, E.M., et al., "Orthopaedic phenotyping of NGLYI deficiency using an international, family-led disease registry," Orphanet. J. Rare Dis., 2019,14(1): 148.
Chou, A.H., "Polyglutamine-expanded ataxin-3 causes cerebellar dysfunction of SCA3 transgenic mice by inducing transcriptional dysregulation," Neurobiol. Dis., 2008, 31(1): 89-101.
Clarke, L.A., et al., "Long-term efficacy and safety of laronidase in the treatment of mucopolysaccharidosis," I. Pediatrics, 2009, 123(1): p. 229-40.
Colella, P., et al., "Emerging issues in AAV-mediated in vivo gene therapy," Mot. Ther. Methods Clin. Dev., 2017, 8: 87-104.
Crawley, J.N., "Behavioral phenotyping of rodents," Comp. Med., 2003, 53(2): 140-146.
Crawley, J.N., "Behavioral phenotyping strategies for mutant mice," Neuron., 2008, 57(6): 809-818.
Dabaj, et al., "NGLY1 Deficiency: A Rare Newly Described Condition with a Typical Presentation," Life, 2021, 11: 187 (pp. 1-8).
Davidoff, A.M., et al., "Sex significantly influences transduction of murine liver by recombinant adeno-associated viral vectors through an androgen-dependent pathway," Blood, 2003, 102(2): 480-488.
Duan, D., "Systemic AAV micro-dystrophin gene therapy for Duchenne muscular dystrophy," Mol. Ther., 2018, 26(10): 2337-2356.
Du Bois, R.M., et al., "Six-minute-walk test in idiopathic pulmona,y fibrosis: test validation and minimal clinically important difference," Am. J. Respir. Crit. Care Med., 2011, 183(9): p. 1231-7.
Enns, G.M., et al., "Mutations in NGLYI cause an inherited disorder of the endoplasmic reticulum-associated degradation pathway," Genet. Med., 2014, 16(10): 751-758.
Foust, K.D., et al., "Rescue of the spinal muscular atrophy phenotype in a mouse model by early postnatal delivery of SMN," Nat. Biotechnol., 2010, 28(3): 271-274.
Fujihira, H., et al., "Lethality of mice bearing a knockout of the Nglyl-gene is partially rescued by the additional deletion of the Engase gene," PLoS Genet., 2017, 13(4): el006696.
Ge, H., et al., "Two novel compound heterozygous mutations in NGLYI as a cause of congenital disorder of deglycosylation: a case presentation," BMC Med. Genet., 2020, 21: 135.
Greig J.A., et al., "Determining the minimally effective dose of a clinical candidate AAV vector in a mouse model of Crigler-Najjar syndrome," Mol. Ther. Methods Clin. Dev., 2018, 10: 237-244.
Greene, J.A., et al., "Reform, regulation, and pharmaceuticals—the Kefauver-Harris Amendments at 50," N. Engl. J. Med, 2012, 367(16): p. 1481-3.
Guyenet, S.J., et al., "A simple composite phenotype scoring system for evaluating mouse models of cerebellar ataxia," J. Vis. Exp., 2010, 21: 1787.
Haijes, H.A., et al., "Aspartylglycosamine is a biomarker for NGLYI-CDDG, a congenital disorder of deglycosylation," Mol. Genet. Metab., 2019, 127(4): 368-372.
Hall, PL, et al., "Urine oligosaccharide screening by MALDI-TOF for the identification ofNGL Yl deficiency," Mol. Genet. Metab., 2018, 124(1 ): 82-86.
Hannatz P., et al., "A novel Blind Start study design to investigate vestronidase alfa for mucopolysaccharidosis VII, an ultra-rare genetic disease," Mol. Genet. Metab., 2018, 123(4): 488-494.
Harmatz, P., et al., "Enzyme replacement therapy for mucopolysaccharidosis VI: a phase 3, randomized, double-blind, placebo-controlled, multinational study of recombinant human N-acetylgalactosamine 4-suifatase (recombinant humcm arylsuifatase B or rhASB) and follow-on, open-label extension study," J. Pediatr, 2006, 148(4): p. 533-539.
Harmatz, P., et al., "A novel Blind Start study design to investigate vestronidase aljafor mucopolysaccharidosis VII, an ultra-rare genetic disease," Mol. Genet. Metab., 2018, 123(4): p. 488-494.
Hendriksz, C.J., et al., "Multi-domain impact of elosulfase alfa in Morquio A syndrome in the pivotal Phase III trial," Mol. Genet. Metab., 2015, 114(2): 178-185.
Hirai, T., et al., "Intrathecal AA V serotype 9-mediated delivery of shRNA against TRPVI attenuates thennal hyperalgesia in a mouse model of peripheral nerve injury," Mol. Ther., 2014, 22(2): 409-419.
Hocquemiller, M., et al., "Adeno-associated virus-based gene therapy for CNS diseases," Hum. Gene Ther., 2016, 27 (7): 478-496.
Hordeaux, J., et al., "Adeno-associated virus-induced dorsal root ganglion pathology," Hum. Gene Ther., 2020, 31 (15-16): 808-818.
Huang, C., et al., "Endo-j3-N-acetylglucosaminidase forms N-GlcNAc protein aggregates during ER-associated degradation in Nglyl-defective cells," Proc. Natl. Acad Sci. USA, 2015, 112(5): 1398-1403.
Huang, R, et al., "UPLC-MS/MS analysis of urinary free oligosaccharides for lysosomal storage diseases: diagnosis and potential treatment monitoring," Clin. Chem., 2018, 64(12): 1772-177.
Jackson, K.L., et al., "AAV9 supports wide-scale transduction of the CNS and TDP-43 disease modeling in adult rats," Mol. Ther. Methods Clin. Dev., 2015, 2: 15036.
Kakkis, E.D., et al., "Long-term cmd high-dose trials of enzyme replacement therapy in the canine model of mucopolysaccharidosis I," Biochem. Mol. Med., 1996, 58(2): p. 156-67.
Lalonde, R., et al., "Brain regions and genes affecting limb-clasping responses," Brain Res. Rev., 2011, 67(1-2): 252-259.
Lam, C., et al., "NGLYI-related congenital disorder of deglycosylation. In: Adam MP, Ardinger HH, Pagon RA, Wallace SE, Bean LJH, Stephens K, Amemiya A, editors, GeneReviews®," [Internet]. Seattle (WA): University of Washington, Seattle; 1993-2019. Feb. 8, 2018.
Lam, C., et al. "Prospective phenotyping ofNGLYI-CDDG, the first congenital disorder of deglycosylation," Genet. Med., 2017, 19(2): 160-168.

(56) References Cited

OTHER PUBLICATIONS

Lanoix J, et al., "A rabbit beta-globin polyadenylation signal directs efficient termination of transcription of polyomavirus DNA," EMBO J., 1988, 7(8): 2515-2522.
Lehrbach, N.J., et al., "Protein sequence editing of SKN-IA/Nrfl by peptide:N-glycanase controls proteasome gene expression," Cell, 2019, 177(3): 737-750.
Levitt, N., et al., "Definition of an efficient synthetic poly(A) site," Genes Dev., 1989, 3(7): 1019-1025.
Lipari, P., et al., "NGLYI deficiency—A rare congenital disorder of deglycosylation," JIMD Rep., 2020, 53(1):2-9.
Lipinski, P., et al., "A Liver involvement in NGLYI congenital disorder of deglycosylation," Pol J Pathol., 2020, 71(1) 66-68.
Lipinski, P., et al., "NGLYI deficiency: novel patient, review of the literature and diagnostic algorithm," JIMD Rep., 2020 b51(1): 82-88.
Maguire, C.A., et al., "Mouse gender influences brain transduction by intravascularly administered AAV9", Mol. Ther., 2013, 21(8): 1470-1471.
Mathai, S.C., et al., "The minimal important difference in the 6-minute walk test for patients with pulmonary arterial hypertension," Am. J. Respir. Crit. Care Med., 2012, 186(5): p. 428-33.
Mazzone, E.S., et al., "Reliability of the North Star Ambulatory Assessment in a multicentric setting," Neuromuscul. Disord., 2009, 19(7): p. 458-61.
Mayhew, J., et al., "Development and preliminary evidence of the psychometric properties of the GNE myopathy functional activity scale," J. Comp. Eff. Res, 2018, 7(4): p. 381-395.
Meadows, A.S., et al., "Threshold for pre-existing antibody levels limiting transduction efficiency of systemic rAAV9 gene delivery: relevance for translation," Mol. Ther. Methods Clin. Dev., 2019, 13: 453-462.
Meadows, A.S., et al., "A GLP-compliant toxicology and biodistribution study: systemic delivery of an rAAV9 vector for the treatment of mucopolysaccharidosis IIIB," Hum. Gene Ther. Clin. Dev., 2015, 26(4): 228-242.
Mendell, J.R., et al., "Single-dose gene-replacement therapy for spinal muscular atrophy," N. Engl. J. Med., 2017, 377 (18): 1713-1722.
Miyazaki, J., et al., "Expression vector system based on the chicken beta-actin promoter directs efficient production of interleukin-5," Gene, 1989, 79(2): 269-277.
Mononen, T., et al., "Liquid-chromatographic detection of aspartylglycosaminuria," Clin Chem., 1986,32(3): 501-502.
Mononen, I., et al., "Enzymatic diagnosis of aspartylglycosaminuria by fluorometric assay of glycosylasparaginase in serum, plasma, or lymphocytes," Clin. Chem., 1994, 40(3): 385-388.
Moser, V.C., et al., "Comparison of chlordimeform and carbaryl using a functional observational battery," Fund Appl. Toxicol., 1988, 11(2): 189-206.
Muenzer, J., et al., "A phase II/III clinical study of enzyme replacement therapy with idursuifase in mucopolysaccharidosis II (Hunter syndrome)," Genet. Med., 2006, 8(8): p. 465-73.
Nakamura, S., et al., "Gene therapy for Glutl-deficient mouse using an adeno-associated virus vector with the human intrinsic GLUTI promoter," J. Gene Med., 2018, 20(4): e3013.
Need, A.C., et al., "Clinical application of exome sequencing in undiagnosed genetic conditions," J. Med. Genet., 2012, 49(6): 353-561.
Neville, D.C., et al., "Hydrophobic glycosides of N-acetylglucosamine can act as primers for polylactosamine synthesis and can affect glycolipid synthesis in vivo," Biochem. J., 1995, 307( Pt 3)(Pt 3): 791-797.
Niemir, et al., "Intravenous administration of scAAV9-Hexb normalizes lifespan and prevents pathology in Sandhoff disease mice," Hum. Mol. Genet., 2018, 27(6): 954-968.
Niwa, H., et al., "Efficient selection for high-expression transfectants with a novel eukaryotic vector," Gene, 1991, 108 (2): 193-199.
Nott, A., et al., "Splicing enhances translation in mammalian cells an additional function of the exonjunction complex," Genes Dev., 2004, 18(2): 210-222.
Okuyama, T., et al., "Japan Elaprase Treatment (JET) study: idursuljase enzyme replacement therapy in adult patients with attenuated Hunter syndrome (Mucopolysaccharidosis II, MPS JI)," Mol. Genet. Metab., 2010, 99(1): p. 18-25.
Panneman, D.M., et al., "Variants in NGLYI lead to intellectual disability, myoclonus epilepsy, sensorimotor axonal polyneuropathy and mitochondrial dysfunction," Clin. Genet., 2020, 97(4): 556-566.
Peyrl, A, et al., "Safety of Ommaya reservoirs in children with brain tumors: a 20-year experience with 5472 intraventricular drug administrations in 98 patients," J. Neurooncol., 2014, 120(1): 139-145.
"Photodynamic therapy of subfoveal choroidal neovascularization in age-related macular degeneration with vertepor. fin: one-year results of 2 randomized clinical trials—TAP report. Treatment of age-related macular degeneration with photodynamic therapy (TAP) Study Group," Arch. Ophthalmol., 1999, 117(10): p. 1329-45.
Pinto, P.L., et al., "NGLYI deficiency—A rare congenital disorder of deglycosylation," JIMD Rep., 2020, 53(1): 2-9.
Pocock, S.J., et al., "The analysis of multiple endpoints in clinical trials," Biometrics, 1987, 43(3): p. 487-98.
Powell, S.K., et al., "Viral expression cassette elements to enhance transgene target specificity and expression in gene therapy," Discov. Med., 2015, 19(102): 49-57.
Puhan, M.A., et al., "Interpretation of treatment changes in 6-minute walk distance in patients with COPD," Eur. Respir. J., 2008, 32(3): p. 637-43.
Reeves, B.C., et al., "Reliability of high- and low-contrast letter charts," Ophthalmic Physiol. Opt, 1993, 13(1): p. 17-26.
Ren, L., et al., "Optimizing in vivo NGLYI gene delivery towards gene therapy for NGLYI deficiency," American Society of Gene and Cell Therapy (ASGCT), 22nd Annual Meeting, Apr. 29 to May 2, 2019.
Robinson, L, et al., "Involvement of the cholinergic system in conditioning and perceptual memory," Behav. Brain Res., 2011, 221(2): 443-465.
Saade, D., et al., "Review of safety and interim analysis of efficacy of a first-in-human intrathecal gene transfer study for giant axonal neuropathy," Presented at the 22nd Annual Meeting for the American Society of Gene and Cell Therapy, Washington, DC. Apr. 29-May 2, 2019. Available at https://cslide-us.ctimeetingtech.com/asgct23/attendee/eposter/file/1348#1. Accessed Sep. 2020.
Samaranch L, et al., "Strong cortical and spinal cord transduction after AAV7 and AAV9 delivery into the cerebrospinal fluid of nonhuman primates," Hum. Gene Ther., 2013, 24(5): 526-532.
Seibenhener, M.L., et al., "Use of the open field maze to measure locomotor and anxiety-like behavior in mice," J. Vis. Exp., 2015, (96): e52434.
Suzuki, T., et al., "The cytoplasmic peptide:N-glycanase (NGLYI)—structure, expression and cellular functions," Gene, 2016, 577(1): 1-7.
Suzuki, T., et al., "Endo-beta-N-acetylglucosaminidase, an enzyme involved in processing of free oligosaccharides in the cytosol," Proc. Natl. Acad. Sci. USA, 2002a, 99(15): 9691-9696.
Suzuki, T., et al., "Cytoplasmic peptide N-glycanase (PNGase) in eukaryotic cells: occurrence, primary structure, and potential functions," FASEB J., 2002b, 16(7): 635-641.
Suzuki, T., et al., "PNGI, a yeast gene encoding a highly conserved peptide:N-glycanase," J. Cell Biol., 2000,149(5): 1039-1052.
Talsness, et al., "A *Drosophila* natural variation screen identifies NKCC1 as a substrate ofNGLYI deglycosylation and a modifier ofNGLYI deficiency," bioRxiv, 2020, 04.13.039651; doi: https://doi.org/10.1101/2020.04.13 039651.
Tomlin, F.M., et al., "Inhibition of NGLYI inactivates the transcription factor Nrfl and potentiates proteasome inhibitor cytotoxicity," ACS Cent. Sci., 2017, 3(11): 1143-1155.
Tornøe J, et al., "Generation of a synthetic mammalian promoter library by modification of sequences spacing transcription factor binding sites," Gene, 2002, 297(1-2): 21-32.

(56) References Cited

OTHER PUBLICATIONS

Valencia, P., et al., "Splicing promotes rapid and efficient mRNA export in mammalian cells," Proc. Natl. Acad. Sci. USA, 2008, 105(9): 3386-3391.
Van Keulen, B.J., et al., "Unexplained death in patients with NGLYI mutations may be explained by adrenal insufficiency," Physiol. Rep., 2019, 7(3): el3979.
Vockley, J., et al., "Results. from a 78-week, single-arm, open-label phase 2 study to evaluate UX007 in pediatric and adult patients with severe long-chain fatty acid oxidation disorders (LC-FAOD)," J. Inherit. Metab. Dis., 2019, 42(1): p. 169-177.
Wang, R.Y., et al., "The long-term safety and efficacy of vestronidase a/fa, rhGUS enzyme replacement therapy, in subjects with mucopolysaccharidosis VII," Mol. Genet. Metab., 2020, 129(3): p. 219-227.
Wraith, J.E., et al., "Enzyme replacement therapy for mucopolysaccharidosis I: a randomized, double-blinded, placebo-controlled, multinational study of recombinant human alpha-L-iduronidase (laronidase)," J. Pediatr,, 2004, 144(5): p. 581-8.
Wright, J.F., "Codon modification and PAMPs in clinical AAV vectors: the tortoise or the hare?" Mol. Ther., 2020, 28 (3):701-703.
Wuang, Y.P et al., "Reliability and responsiveness of the Bruininks-Oseretsky Test of Motor Proficiency-Second Edition in children with intellectual disability," Res. Dev. Disabil., 2009, 30(5): p. 847-55.
Xia, B., et al., "Oligosaccharide analysis in urine by maldi-tof mass spectrometry for the diagnosis of lysosomal storage diseases," Clin. Chem., 2013, 59(9): 1357-1368.
Zanta-Boussif, M.A., et al., "Validation of a mutated PRE sequence allowing high and sustained transgene expression while abrogating WHV-X protein synthesis: application to the gene therapy of WAS," Gene Ther., 2009, 16(5): 605-619.

* cited by examiner

COMPOSITIONS AND METHODS FOR TREATING NGYL1 DEFICIENCY

CROSS REFERENCE TO RELATED APPLICATIONS

This application claims the benefit of U.S. Provisional Application No. 63/180,065, filed Apr. 26, 2021. The content of this earlier filed application is hereby incorporated by reference herein in their entirety.

INCORPORATION OF THE SEQUENCE LISTING

The present application contains a sequence listing that is submitted via EFS-Web concurrent with the filing of this application, containing the file name "38132_0001P1_SL.txt" which is 28,672 bytes in size, created on Apr. 11, 2022, and is herein incorporated by reference in its entirety.

BACKGROUND

NGLY1 deficiency is an ultra-rare autosomal recessive disorder caused by the loss of NGLY1 function. The current known prevalence is 27 living U.S. patients in ~331 million. It is an extremely serious pediatric disease that manifests at birth and early development, and severely impacts day-to-day functioning. Because the NGLY1 protein is not a secreted protein, tissue biopsy would be required for its assay, and there is no diagnostic assay for its activity. Whole exome or whole genome sequencing is currently the only way to confirm diagnosis.

Individuals with NGLY1 deficiency have extremely severe symptomatic issues. Day-to-day management by caretakers is required for patient survival. Phenotypically, presentation of the disease includes (1) global developmental delay and/or intellectual disability, (2) (hypo)alacrima, (3) elevated liver transaminases, and (4) hyperkinetic movement disorder. Ninety percent of patients will never walk and must use walkers or wheelchairs from an early age. Nearly all patients (94.6%; 35/37) surveyed as part of an NGLY1 Registry are non-verbal, and those who are able to verbalize rely on augmentative and alternative communication (AAC) devices for communication and therapy. Manual feeding administered by a caregiver or use of a gastrostomy tube (G-tube) is necessary for adequate nutrition. Caregivers must manage all aspects of daily bathing and toileting regimens. Pneumonia and urinary tract infections require frequent hospitalization. About half of patients (51.4%; 18/37) experience seizures that may require hospitalization. Surgeries are common for multiple issues, including spinal fusions, inguinal hernias, tracheostomies, and kidney problems.

Additional multisystem clinical manifestations include apparently progressive cerebral atrophy and acquired microcephaly; ophthalmologic symptoms including lagophthalmos, optic atrophy, and retinal changes; constipation; hepatomegaly and other hepatic abnormalities; hypocholesterolemia; length-dependent sensorimotor axonal loss; muscle atrophy; and joint contractures that limit mobility.

There are 51 variants for the 65 patients identified by the Grace Science Foundation. These include nonsense, missense, frameshift, and splicing mutations interspersed throughout the NGLY1 gene, as well as 3 partial or full gene deletions. Variants are found in the catalytic domain, the AAA ATPase binding PUB domain (IPR018997), and a PAW domain (IPR006588) that binds to the mannose moieties of N-linked oligosaccharide chains (FIG. 3) (Zhou X, et al. Proc Natl Acad Sci USA. 2006; 103(46):17214-17219). The most commonly reported nonsense variant, c.1201A>T (p.Arg401Ter) may portend a more severe presentation corresponding with a near absent transcript (Lam C, et al. NGLY1-related congenital disorder of deglycosylation. In: Adam M P, Ardinger H H, Pagon R A, Wallace S E, Bean L J H, Stephens K, Amemiya A, editors. GeneReviews® [Internet]. Seattle (WA): University of Washington, Seattle; 1993-2019. 2018 Feb. 8).

There is currently no known treatment for NGLY1 deficiency and there is tremendous need in the art for such a treatment.

SUMMARY

An invention disclosed herein are methods for promoting expression of functional NGLY1 protein in a subject, the methods comprising administering to the subject in need of treatment an effective amount of a recombinant adeno-associated virus (rAAV) comprising a capsid comprising a nucleic acid engineered to express human NGLY1 in at least the central nervous system ("CNS") of the subject (and may express in tissues outside the CNS), wherein the subject has an NGLY1 deficiency. In embodiments, the subject comprises two endogenous NGLY1 alleles having a loss-of-function mutation associated with NGLY1 deficiency. In certain embodiments, the subject is an NGLY1 deficiency carrier and has one loss of function allele. In embodiments, the rAAV comprising the transgene engineered to express NGLY1 is administered by intracerebroventricular (ICV) administration or alternatively by administration to the cisterna magna. In embodiments, the rAAV has an AAV9 serotype. The coding sequence for the NGLY1 protein is, in embodiments, codon optimized, including for reduction in the presence of CpG dinucleotides and may have the nucleotide sequence of SEQ ID NO: 1. The methods of administration described herein result in improvement in symptoms and/or biomarkers of NGLY1 deficiency within an appropriate time period after the administration, for example reduction in accumulation of GlcNAc-Asparagine (GNA) in the CNS or other biological samples of a subject, behavioral metrics that can quantify or are indicative of one or more NGLY1 deficiency signs or symptoms, frequency of seizures, developmental delay, neurocognitive function, dystonia, polyneuropathy, abnormal sweat response, gait abnormalities, and motor function.

Also, disclosed herein are methods of treating a subject having NGLY1 deficiency, the methods comprising administering to the subject an effective amount of an rAAV comprising a capsid containing a nucleic acid engineered to express NGLY1 at least in the CNS of the subject, in embodiments where the administration is ICV administration (alternatively, the rAAV may be administered via the cisterna magna).

According to one embodiment of the invention are disclosed herein are methods of reducing accumulation of GlcNAc-Asn (GNA) in at least the CNS of a subject, the methods comprising administering to the subject a therapeutically effective amount of a recombinant adeno-associated virus (rAAV) comprising a nucleic acid construct comprising a transgene encoding NGLY1 operably linked to regulatory elements for expression in the CNS of the subject, where the subject has an NGLY1 deficiency, in particular embodiments where the subject has 2 (or is homozygous for) loss of function NGLY1 alleles, or alternatively, wherein the subject comprises at least one endogenous NGLY1 allele having a loss-of-function mutation associated with NGLY1 deficiency, for example, is a carrier of NGLY1 deficiency, and, in embodiments the rAAV is administered by ICV administration or, alternatively via the cisterna magna. In embodiments, the subject comprises two endogenous NGLY1 alleles having a loss-of-function mutation associated with NGLY1 deficiency.

According to one embodiment of the invention are disclosed herein are methods of monitoring the levels of GlcNAc-Asn (GNA) in the cerebrospinal fluid (CSF) and/or plasma of a subject, the methods comprising determining the levels of GNA in a first sample comprising CSF and/or plasma before administering to the subject a therapeutically effective amount of a recombinant adeno-associated virus (rAAV) comprising a nucleic acid construct comprising a transgene encoding NGLY1 operably linked to regulatory elements for expression in the CNS of the subject, and comparing the levels of GNA in a subsequent sample from the subject after the administration of the rAAV, and determining the efficacy of the rAAV, wherein the subject comprises at least one endogenous NGLY1 allele having a loss-of-function mutation associated with NGLY1 deficiency, and, in embodiments the rAAV is administered by ICV administration or, alternatively via the cisterna magna. In embodiments, the subject comprises two endogenous NGLY1 alleles having a loss-of-function mutation associated with NGLY1 deficiency.

Another embodiment of the invention disclosed herein are rAAVs comprising a nucleic acid engineered to express NGLY1 in at least the central nervous system ("CNS"). In another embodiment the nucleic acid encoding the NGLY1 further comprises a promoter of SEQ ID NO: 4 and intron having SEQ ID NO: 5. Provided are gene expression cassette constructs having nucleotide sequence of SEQ ID NO: 8 (including the nucleotide sequence of SEQ ID NO: 1 operably linked to a CAG promoter and a polyA signal sequence) or SEQ ID NO: 9 (the entire construct with the flanking ITR sequences).

In yet another embodiment of the invention disclosed herein are the nucleic acid molecules expressing the NGLY1 that are incorporated into the rAAVs of the invention.

In another embodiment of the invention are host cells comprising the rAAVs of the invention.

BRIEF DESCRIPTION OF THE DRAWINGS

FIG. 6A shows that GS-100 treatment improves rat latency to fall on rotarod. FIG. 6B shows that ICV administration of GS-100 treatment increases rearing.

FIG. 7 also shows that improvement in rearing behavior is associated with CSF and tissue GNA level reductions following GS-100 treatment.

DETAILED DESCRIPTION

Figure 1:
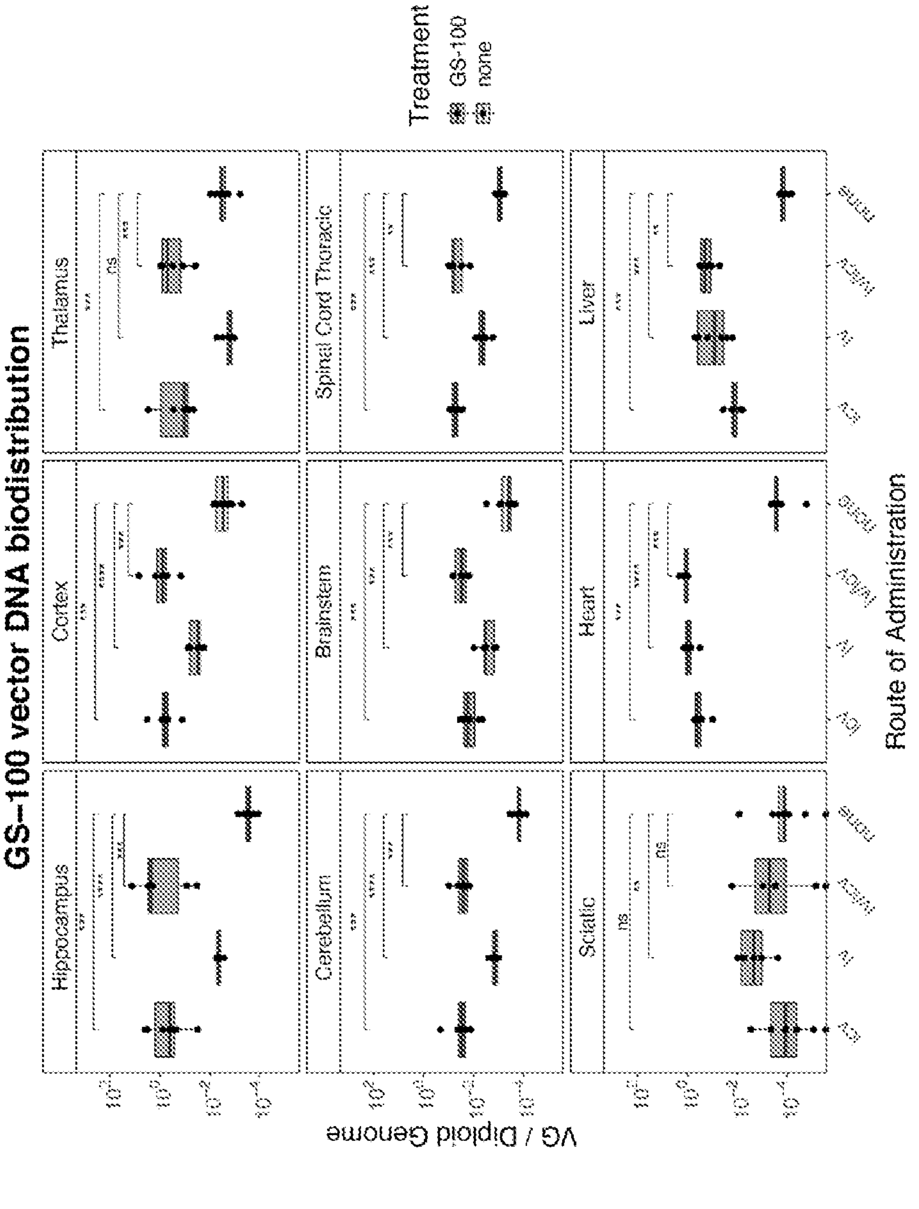
FIG. 1 shows GS-100 (e.g., rAAV9 vector that comprises a codon-optimized full-length version of hNGLY1 (SEQ ID NO: 1) under the control of the CAG promoter and a polyA signal with flanking ITR sequences-see FIG. 8) vector DNA biodistribution.

The invention can be understood more readily by reference to the following detailed description of the invention, the figures and the examples included herein.

The terminology used herein is for the purpose of describing particular aspects of the invention and is not intended to be limiting.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein, the term "transgene" refers to a gene or genetic material that has been transferred or artificially introduced into the genome by a genetic engineering technique from one organism to another, i.e., the host organism.

As used herein, the term "transgene expression" relates to the control of the amount and timing of appearance of the functional product of a transgene in a host organism.

The term “endogenous” as used herein refers to substances and processes originating from within an organism, tissue or cell.

“Inhibit,” “inhibiting” and “inhibition” mean to diminish or decrease gene expression, activity, response, condition, disease, or other biological parameter (e.g., GNA). This can include, but is not limited to, the complete ablation of the activity, response, condition, or disease. This may also include, for example, a 10% inhibition or reduction in gene expression, activity, response, condition, or disease as compared to the wild-type or control level. Thus, in some aspects, the inhibition or reduction can be a 10, 20, 30, 40, 50, 60, 70, 80, 90, 100%, or any amount of reduction in between as compared to native or control levels. In some aspects, the inhibition or reduction is 10-20, 20-30, 30-40, 40-50, 50-60, 60-70, 70-80, 80-90, or 90-100% as compared to wild-type or control levels. In some aspects, the inhibition or reduction is 0-25, 25-50, 50-75, or 75-100% as compared to wild-type or control levels.

“Promote,” “promotion,” and “promoting” refer to an increase in an activity, response, condition, disease, or other biological parameter. This can include but is not limited to the initiation of the activity, response, condition, or disease. This may also include, for example, a 10% increase in the activity, response, condition, or disease as compared to the wild-type or control level. Thus, in some aspects, the increase or promotion can be a 10, 20, 30, 40, 50, 60, 70, 80, 90, 100%, or more, or any amount of promotion in between compared to native or control levels. In some aspects, the increase or promotion is 10-20, 20-30, 30-40, 40-50, 50-60, 60-70, 70-80, 80-90, or 90-100% as compared to wild-type or control levels. In some aspects, the increase or promotion is 0-25, 25-50, 50-75, or 75-100%, or more, such as, for example, 200, 300, 500, or 1000% more as compared to wild-type or control levels. In some aspects, the increase or promotion can be greater than 100 percent as compared to wild-type or control levels, such as 100, 150, 200, 250, 300, 350, 400, 450, 500% or more as compared to the wild-type or control levels.

The term “operatively linked to” refers to the functional relationship of a nucleic acid with another nucleic acid sequence. Promoters, enhancers, transcriptional and translational stop sites, and other signal sequences are examples of nucleic acid sequences linked to other sequences in order confer functional activity of the construct as a whole. For example, operative linkage of DNA to a transcriptional control element refers to the physical and functional relationship between the DNA and promoter such that the transcription of such DNA is initiated from the promoter by an RNA polymerase that specifically recognizes, binds to and transcribes the DNA.

As used herein, the terms “promoter,” “promoter element,” or “promoter sequence” are equivalents and as used herein, refers to a DNA sequence which when operatively linked to a nucleotide sequence of interest is capable of controlling the transcription of the nucleotide sequence of interest into mRNA. A promoter is located 5' (i.e., upstream) of a nucleotide sequence of interest (e.g., proximal to the transcriptional start site of a structural gene), although not necessarily immediately upstream because of the optional inclusion of intervening sequences between the promoter and the sequence to be transcribed, whose transcription into mRNA it controls, and provides a site for specific binding by RNA polymerase and other transcription factors for initiation of transcription.

As used herein, the term “subject” refers to the target of administration, e.g., a human. Thus, the subject of the disclosed methods can be a vertebrate, such as, for example, a mammal, a fish, a bird, a reptile, or an amphibian. The term “subject” also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In some aspects, a subject can be a mammal. In some aspects, a subject can be a human. The term does not denote a particular age or sex. Thus, adult, child, adolescent and newborn subjects, as well as fetuses, whether male or female, are within the scope of this invention.

As used herein, the term “patient” refers to a subject afflicted with a disease or disorder. The term “patient” includes human and veterinary subjects. In some aspects of the methods of this invention, the “patient” has been diagnosed with a need for treatment for NGLY1 deficiency, such as, for example, prior to administering then gene therapy NGLY1 compositions of this invention. In some aspects of the methods of this invention, the patient in need for treatment for NGLY1 deficiency can be heterozygous for a loss of function mutation in the NGLY1 gene or homozygous for a loss of function mutation in the NGLY1 gene.

As used herein, the term “normal” refers to an individual, a sample or a subject that does not have NGLY1 deficiency or does not have an increased susceptibility of developing NGLY1 deficiency.

As used herein, the term “treat” or “treatment” refers to the medical management of a patient with the intent to cure, ameliorate, stabilize, (e.g., NGLY1 deficiency). This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) inhibiting the disease, i.e., arresting its development; or (ii) relieving the disease, i.e., causing regression of the disease (e.g., NGLY1 deficiency).

As used herein, the term “prevent” or “preventing” refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. For example, “prevent” is meant to mean minimize the chance that a subject who has an increased susceptibility for developing NGLY1 deficiency will develop NGLY1 deficiency. In the context as used herein, preventing does not need to eliminate completely all sequele associated with NGLY1 deficiency and would encompass any reduction in the expression of one or more symptoms associated with NGLY1 deficiency.

Disclosed herein, is a therapeutic modality, preferably an AAV9-mediated NGLY1 gene therapy (e.g., GS-100) for treating subjects with NGLY1 deficiency to reduce one or more symptoms associated with NGLY1 deficiency or preventing the development of one or more symptoms associated with NGY1 deficiency. The development of GS-100 included 1) identifying a reliable biomarker for NGLY1 deficiency consistent with a lack of NGLY1 enzymatic activity, and 2) using an animal disease model that exhibits both systemic and CNS/PNS disease hallmarks.

The NGLY1 gene encodes N-glycanase, a conserved cytosolic deglycosylase that is involved in the endoplasmic-reticulum-associated protein degradation (ERAD) pathway. It cleaves N-glycans from the asparagine residues of misfolded proteins at the GlcNAc-Asn bond. In NGLY1's absence, this GlcNAc-Asn bond is left intact, which could lead to the cytoplasmic accumulation of Asn-glycan metabolites like GlcNAc-Asn (aspartylglucosamine or GNA). Loss of NGLY1 activity in cells leads to impaired proteotoxic stress response and defects in energy metabolism. Engineered loss of NGLY1 in rats results in decreased survival early in life, severe neurodegenerative phenotypes, and pathological abnormalities in the peripheral and central nervous systems, similar to what is observed in patients. GNA can be also used as a biomarker of the disease directly related to the activity of NGLY1 and as disclosed herein was found to be elevated in both patient and Ngly1 deficient rat samples.

Compositions

Nucleic Acids. Disclosed herein is a nucleic acid comprising at least one transgene operably linked to a promoter, wherein the transgene encodes NGLY1 (N-glycanase 1; GENE ID: 55768). The NGLY1 gene encodes N-glycanase (EC 3.5.1.52), a highly conserved enzyme that catalyzes deglycosylation of misfolded N-linked glycoproteins by cleaving the glycan chain before the proteins are degraded by the proteasome. NGLY1 is a cytoplasmic component of the endoplasmic reticulum-associated degradation (ERAD) pathway that identifies and degrades misfolded glycoproteins.

The NGLY1 gene can encode an mRNA having the nucleotide sequence of NM 001145293.1, NM 001145294.1, NM 001145295.1, or NM 018297.4. The NGLY1 gene can encode a protein having the amino acid sequence NP 001138765.1, NP 001138766.1, NP 001138767.1 or NP 060767.2. In some embodiments of the invention, the NGLY1 gene is codon-optimized, for example, for expression in a mammal, such as a human. Sequences corresponding to all GenBank accession numbers described in the disclosure are incorporated herein by reference in their entirety. Note that DNA sequences provided herein may also include the reverse complement to form the double stranded DNA sequence or may be a reverse complement of the sequences disclosed herein.

In some aspects, an isolated nucleic acid encoding NGLY1 comprises the following sequence:

```
                                        (SEQ ID NO: 1)
ATGGCCGCTGCTGCCCTGGGATCATCAAGTGGGTCCGCTTCACCTGCCG

TCGCCGAACTGTGCCAGAACACCCCCGAAACCTTCCTGGAGGCaTCCAA

GCTGCTGCTGACCTACGCCGACAACATCCTGCGCAATCCAAACGATGAG

AAGTATCGCTCCATCAGGATCGGCAATACCGCCTTCTCTACAAGGCTGC

TGCCCGTGAGGGGAGCAGTGGAGTGCCTGTTCGAGATGGGCTTTGAGGA

GGGCGAGACACACCTGATCTTTCCCAAGAAGGCCAGCGTGGAGCAGCTG
```

-continued

```
CAGAAGATCAGGGACCTGATCGCCATCGAGAGAAGCTCCCGGCTGGATG

GCTCTAACAAGAGCCACAAGGTGAAGTCTAGCCAGCAGCCTGCAGCAAG

CACACAGCTGCCTACCACACCATCCTCTAATCCATCCGGCCTGAACCAG

CACACCAGGAATAGACAGGGACAGAGCTCCGACCCACCTAGCGCCTCCA

CAGTGGCAGCCGATTCTGCCATCCTGGAGGTGCTGCAGAGCAACATCCA

GCACGTGCTGGTGTACGAGAATCCAGCCCTGCAGGAGAAGGCCCTGGCA

TGCATCCCAGTGCAGGAGCTGAAGCGGAAGAGCCAGGAGAAGCTGTCCA

GGGCAAGGAAGCTGGACAAGGGCATCAATATCAGCGACGAGGATTTCCT

GCTGCTGGAGCTGCTGCACTGGTTTAAGGAGGAGTTCTTTCACTGGGTG

AACAATGTGCTGTGCTCCAAGTGTGGCGGCCAGACCAGGAGCAGAGATC

GGTCCCTGCTGCCTTCTGACGATGAGCTGAAGTGGGGCGCCAAGGAGGT

GGAGGACCACTACTGCGATGCCTGTCAGTTCTCCAACCGCTTTCCCAGG

TATAACAATCCTGAGAAGCTGCTGGAGACAAGATGCGGCCGGTGTGGCG

AGTGGGCCAATTGTTTCACACTGTGCTGTAGAGCCGTGGGCTTTGAGGC

CAGATACGTGTGGGACTATACCGATCACGTGTGGACAGAGGTGTACTCT

CCCAGCCAGCAGAGATGGCTGCACTGCGACGCCTGTGAGGACGTGTGCG

ATAAGCCTCTGCTGTACGAGATCGGCTGGGGCAAGAAGCTGTCTTATGT

GATCGCCTTCAGCAAGGACGAGGTGGTGGATGTGACCTGGCGGTATAGC

TGTAAGCACGAGGAAGTGATCGCCAGGAGAACCAAGGTGAAGGAGGCCC

TGCTGCGCGACACAATCAATGGCCTGAACAAGCAGAGGCAGCTGTTCCT

GTCCGAGAACCGGCGCAAGGAGCTGCTGCAGAGGATCATCGTGGAGCTG

GTGGAGTTTATCTCTCCTAAGACCCCAAAGCCAGGAGAGCTGGGAGGAA

GGATCTCCGGCTCTGTGGCCTGGCGCGTGGCCAGGGGCGAGATGGGCCT

GCAGAGGAAGGAGACACTGTTCATCCCATGCGAGAACGAGAAGATCTCT

AAGCAGCTGCACCTGTGCTACAATATCGTGAAGGACAGATATGTGCGGG

TGTCCAACAATAACCAGACCATCTCTGGCTGGGAGAACGGCGTGTGGAA

GATGGAGAGCATCTTTAGAAAGGTGGAGACAGATTGGCACATGGTGTAC

CTGGCCCGGAAGGAGGGCTCTAGCTTCGCCTATATCAGCTGGAAGTTTG

AGTGTGGCTCCGTGGGCCTGAAGGTGGACAGCATCTCCATCAGAACCTC

CTCTCAGACATTCCAGACCGGCACAGTGGAGTGGAAGCTGaGGTCCGAT

ACCGCCCAGGTGGAGCTGACAGGCGACAATTCCCTGCACTCTTACGCCG

ATTTCTCTGGCGCCACCGAAGTGATCCTGGAGGCAGAGCTGAGCAGGGG

CGACGGCGATGTGGCCTGGCAGCACACACAGCTGTTTAGGCAGAGCCTG

AACGACCACGAGGAGAATTGCCTGGAGATTATTATCAAGTTTTCCGACC

TGTGA.
```

In some embodiments, the nucleic acid sequence encoding NGLY1 comprises at least 80%, at least 85%, at least 90%, at least 95%, at least 96%, at least 97%, at least 98%, or at least 99% identity to SEQ ID NO: 1. In some aspects, the nucleic acid sequence encoding NGLY1 gene comprises up to 20 nucleotides that are different from the NGLY1 gene set forth in SEQ ID NO: 1. In some aspects, the NGLY1 gene comprises 1, 2, 3, 4, 5, 6, 7, 8, 9, 10, 11, 12, 13, 14, 15, 16, 17, 18, 19, or 20 nucleotides that are different from the NGLY1 gene set forth in SEQ ID NO: 1. In some aspects, the nucleic acid sequence encoding NGLY1 gene comprises more than 20 nucleotides that are different from the NGLY1 gene set forth in SEQ ID NO: 1.

In some aspects, the nucleic acid sequence encoding NGLY1 comprises insertions relative to SEQ ID NO: 1. In some aspects, the nucleic acid sequences encoding NGLY1 comprises insertions relative to SEQ ID NO: 1 that do not introduce a frameshift mutation. In some aspects, an insertion in the nucleic acid sequence relative to SEQ ID NO: 1 involves the insertion of multiples of 3 nucleotides (e.g., 3, 6, 9, 12, 15, 18, etc.). In some aspects, an insertion in the nucleic acid sequence relative to SEQ ID NO: 1 leads to an increase in the total number of amino acid residues in the resultant NGLY1 protein (e.g., an increase of 1-3, 15, 3-10, 5-10, 5-15, or 10-20 amino acid residues).

In some aspects, the nucleic acid sequence encoding NGLY1 comprises deletions relative to SEQ ID NO: 1. In some aspects, the nucleic acid sequences encoding NGLY1 comprises deletions relative to SEQ ID NO: 1 that do not introduce a frameshift mutation. In some aspects, a deletion in the nucleic acid sequence relative to SEQ ID NO: 1 involves the deletion of multiples of 3 nucleotides (e.g., 3, 6, 9, 12, 15, 18, etc.). In some aspects, a deletion in the nucleic acid sequence relative to SEQ ID NO: 1 leads to an decrease in the total number of amino acid residues in the resultant NGLY1 protein (e.g., a decrease of 1-3, 1-5, 3-10, 5-10, 5-15, or 10-20 amino acid residues).

In some aspects, the nucleic acid sequence encoding NGLY1 is a codon-optimized sequence (e.g., codon optimized for expression in mammalian cells). In some aspects, a codon-optimized sequence encoding NGLY1 comprises reduced GC content relative to a wild-type sequence that has not been codon-optimized. In some aspects, a codon-optimized sequence encoding NGLY1 comprises a 1-5%, 3-5%, 3-10%, 5-10%, 5-15%, 10-20%, 15-30%, 20-40%, 25-50%, or 30-60% reduction in GC content relative to a wild-type sequence that has not been codon-optimized. In some aspects, a codon-optimized sequence encoding NGLY1 comprises fewer guanine and/or cytosine nucleobases relative to a wild-type sequence that has not been codon-optimized. In some aspects, a codon-optimized sequence encoding NGLY1 comprises 1-5, 3-5, 3-10, 5-10, 5-15, 10-20, 15-30, 20-40, 25-50, or 30-60 fewer guanine and/or cytosine nucleobases relative to a wild-type sequence that has not been codon-optimized. In some aspects, a codon-optimized sequence encoding NGLY1 comprises fewer CpG dinucleotide islands relative to a wild-type sequence that has not been codon-optimized. In some embodiments, a codon-optimized sequence encoding NGLY1 comprises 1-3, 3-5, 3-10, 5-10, 5-15, 10-20, 15-30, 20-40, 25-50, or 30-60 fewer CpG dinucleotide islands relative to a wild-type sequence that has not been codon-optimized In a specific embodiment the nucleotide sequence encoding NGLY1 is SEQ ID NO: 1.

Promoters. In the constructs disclosed herein nucleic acid encoding the NGLY1 protein, including, the nucleotide sequence of SEQ ID NO: 1, is operably linked to a promoter to direct expression of the NGLY1 coding sequence, particularly in CNS cells. In some aspects, the promoter can be a constitutive promoter, for example a chicken beta-actin (CBA) promoter, a retroviral Rous sarcoma virus (RSV) LTR promoter (optionally with the RSV enhancer), a cytomegalovirus (CMV) promoter (optionally with the CMV enhancer) [see, e.g., Boshart et al., Cell, 41:521-530 (1985)], a CMV enhanced chicken 3-actin promoter (CB), a CAG promoter, a SV40 promoter, a dihydrofolate reductase promoter, a β-actin promoter, a phosphoglycerol kinase (PGK) promoter, or an EF1a promoter [Invitrogen]. In some aspects, a promoter can be an enhanced chicken β-actin promoter. In some aspects, a promoter can be a U6 promoter. In some aspects, the promoter can be a CB6 promoter. In some aspects, the promoter can be a JeT promoter. In some aspects, a promoter can be a CB promoter.

In some aspects, the CB promoter comprises the following sequence:

```
                                              (SEQ ID NO: 2)
CACGTTCTGCTTCACTCTCCCCATCTCCCCCCCCTCCCCACCCCCAATT

TTGTATTTATTTATTTTTTAATTATTTTGTGCAGCGATGGGGGCGGGGG

GGGGGGGCGCGCGCCAGGCGGGGCGGGGCGGGGCGAGGGGCGGGGCGGG

GCGAGGCGGAGAGGTGCGGCGGCAGCCAATCAGAGCGGCGCGCTCCGAA

AGTTTCCTTTTATGGCGAGGCGGCGGCGGCGGCGGCCCTATAAAAAGCG

AAGCGCGCGGCGGG.
```

In some aspects, a promoter can be an inducible promoter. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which can be useful include those which are regulated by a specific physiological state, e.g., temperature, acute phase, a particular differentiation state of the cell, or in replicating cells only.

In some aspects, the native promoter for the transgene (e.g., NGLY1) can be used. In some aspects, the native promoter can be used when it is desired that expression of the transgene should mimic the expression of a native wild-type NGLY1 gene (e.g., a non-mutated NGLY1 gene). The native promoter can be used when expression of the transgene must be regulated temporally or developmentally, or in a tissue-specific manner, or in response to specific transcriptional stimuli. In some aspects, other native expression control elements, such as enhancer elements, polyadenylation sites or Kozak consensus sequences can also be used to mimic the native expression.

In some aspects, the promoter drives transgene expression in neuronal tissues. In some aspects, the disclosure provides a nucleic acid operably comprising a tissue-specific promoter operably linked to a transgene. As used herein, "tissue-specific promoter" refers to a promoter that preferentially regulates (e.g., drives or up-regulates) gene expression in a particular cell type relative to other cell types. A cell-type-specific promoter can be specific for any cell type, such as central nervous system (CNS) cells, liver cells (e.g., hepatocytes), heart cells, muscle cells, etc. Examples of tissue-specific promoters include but are not limited to a liver-specific thyroxin binding globulin (TBG) promoter, an insulin promoter, a creatine kinase (MCK) promoter, a a-myosin heavy chain (a-MHC) promoter, or a cardiac Troponin T (cTnT) promoter. Other exemplary promoters include Beta-actin promoter, hepatitis B virus core promoter (Sandig et al., Gene Ther., 3:1002-9 (1996)); alpha-fetoprotein (AFP) promoter (Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998)), and the immunoglobulin heavy chain promoter.

As used herein, the term "hybrid promoter" refers to a regulatory construct capable of driving transcription of an RNA transcript (e.g., a transcript comprising encoded by a transgene) in which the construct comprises two or more regulatory elements artificially arranged. Typically, a hybrid promoter comprises at least one element that is a minimal promoter and at least one element having an enhancer sequence or an intronic, exonic, or UTR sequence comprising one or more transcriptional regulatory elements. In some aspects in which a hybrid promoter comprises an exonic, intronic, or UTR sequence, such sequence(s) can encode upstream portions of the RNA transcript while also containing regulatory elements that modulate (e.g., enhance) transcription of the transcript. In some aspects, two or more elements of a hybrid promoter can be from heterologous sources relative to one another. In some aspects, a hybrid promoter comprises a first sequence from the chicken beta-actin promoter and a second sequence of the CMV enhancer. In some aspects, the hybrid promoter comprises a first sequence from the CMV enhancer and a second sequence from the chicken beta-actin promoter. In some aspects, a hybrid promoter comprises a first sequence from a chicken beta-actin promoter and a second sequence from an intron of a chicken-beta actin gene. In some aspects, a hybrid promoter comprises a first sequence from the chicken beta-actin promoter fused to a CMV enhancer sequence and a sequence from an intron of the chicken-beta actin gene. In some aspects, a hybrid promoter comprises a CB6 promoter. In some aspects, a hybrid promoter comprises a JeT promoter. In some aspects, the promoter can be a CAG promoter. In some aspects, the CAG promoter comprises a CMV enhancer sequence and a CB promoter sequence. In some aspects, the CMV enhancer sequence comprises the following sequence:

(SEQ ID NO: 3)

```
CTAGTCGACATTGATTATTGACTAGTTATTAATAGTAATCAATTACGGG
GTCATTAGTTCATAGCCCATATATGGAGTTCCGCGTTACATAACTTACG
GTAAATGGCCCGCCTGGCTGACCGCCCAACGACCCCCGCCCATTGACGT
CAATAATGACGTATGTTCCCATAGTAACGCCAATAGGGACTTTCCATTG
ACGTCAATGGGTGGAGTATTTACGGTAAACTGCCCACTTGGCAGTACAT
CAAGTGTATCATATGCCAAGTACGCCCCCTATTGACGTCAATGACGGTA
```

-continued

```
AATGGCCCGCCTGGCATTATGCCCAGTACATGACCTTATGGGACTTTCC
TACTTGGCAGTACATCTACGTATTAGTCATCGCTATTAC.
```

In some aspects, CAG promoter comprises the following sequence (including the double stranded DNA sequence with the reverse complement):

(SEQ ID NO: 4)

```
CTAGTCGACATTGATTATTGACTAGTTATTAATAGTAATCAATTACGGG
GTCATTAGTTCATAGCCCATATATGGAGTTCCGCGTTACATAACTTACG
GTAAATGGCCCGCCTGGCTGACCGCCCAACGACCCCCGCCCATTGACGT
CAATAATGACGTATGTTCCCATAGTAACGCCAATAGGGACTTTCCATTG
ACGTCAATGGGTGGAGTATTTACGGTAAACTGCCCACTTGGCAGTACAT
CAAGTGTATCATATGCCAAGTACGCCCCCTATTGACGTCAATGACGGTA
AATGGCCCGCCTGGCATTATGCCCAGTACATGACCTTATGGGACTTTCC
TACTTGGCAGTACATCTACGTATTAGTCATCGCTATTACCATGTCGAGG
ACGCGTCCACGTTCTGCTTCACTCTCCCCATCTCCCCCCCCTCCCCACC
CCCAATTTTGTATTTATTTATTTTTTAATTATTTTGTGCAGCGATGGGG
GCGGGGGGGGGGGGGGCGCGCCAGGCGGGGGGGGGGGGCGAGGGGCGG
GGCGGGGCGAGGCGGAGAGGTGCGGCGGCAGCCAATCAGAGCGGCGCGC
TCCGAAAGTTTCCTTTTATGGCGAGGCGGCGGCGGCGGCGGCCCTATAA
AAAGCGAAGCGCGCGGCGGG.
```

In NGLY1 expressing constructs disclosed herein, the NGLY1 coding sequence, for example SEQ ID NO: 1 is operably linked to the CAG "promoter" or regulatory sequence, which is SEQ ID NO: 4.

In some aspects, the vector can further comprise conventional control elements which are operably linked with elements of the transgene in a manner that permits its transcription, translation and/or expression in a cell transfected with the vector or infected with the virus produced by the disclosure. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (e.g., Kozak consensus sequence); sequences that enhance protein stability; and when desired, sequences that enhance secretion of the encoded product. A number of expression control sequences, including promoters which are native, constitutive, inducible and/or tissue-specific, are known in the art and may be utilized.

In certain embodiments, the constructs comprising the nucleotide sequence encoding NGLY1 include an intron sequence which is operably linked and 5' to the coding sequence. In particular, the intron sequence may be a chimeric intron. In some aspects, a chimeric intron comprises a nucleic acid sequence from a chicken beta-actin gene, for example a non-coding intronic sequence from intron 1 of the chicken beta-actin gene. In some aspects, the intronic sequence of the chicken beta-actin gene ranges from about 50 to about 150 nucleotides in length (e.g., any length between 50 and 150 nucleotides, inclusive). In some aspects, the intronic sequence of the chicken beta-actin gene ranges from about 100 to 120 (e.g., 100, 101, 102, 103, 104, 105, 106, 107, 108, 109, 110, 111, 112, 113, 114, 115, 116, 117, 118, 119, or 120) nucleotides in length. In some aspects, a chimeric intron can be adjacent to one or more untranslated sequences (e.g., an untranslated sequence located between the promoter sequence and the chimeric intron sequence and/or an untranslated sequence located between the chimeric intron and the first codon of the transgene sequence). In some aspects, each of the one or more untranslated sequences can be non-coding sequences from a rabbit beta-globulin gene (e.g., untranslated sequence from rabbit beta-globulin exon 1, exon 2, etc.). In certain embodiments, the intron sequence is as follows (which is one strand of the DNA sequence and may include the reverse complement as well forming the double stranded sequence):

(SEQ ID NO: 5)
TATTGCGGTAGTTTATCACAGTTAAATTGCTAACGCAGTCAGTGCTTCT

GACACAACAGTCTCGAACTTAAGCTGCAGAAGTTGGTCGTGAGGCACTG

GGCAGGTAAGTATCAAGGTTACAAGACAGGTTTAAGGAGACCAATAGAA

ACTGGGCTTGTCGAGACAGAGAAGACTCTTGCGTTTCTGATAGGCACCT

ATTGGTCTTACTGACATCCACTTTGCCTTTCTCTCCACAGGCAGTGTCC

ACTCCCAGTTCAATTACAGCTCTTAAGGCTAGAGTACTTAATACGACTC

ACTATAG.

In some aspects, the rAAV comprises a posttranscriptional response element. As used herein, the term "posttranscriptional response element" refers to a nucleic acid sequence that, when transcribed, adopts a tertiary structure that enhances expression of a gene. Examples of posttranscriptional regulatory elements include, but are not limited to, woodchuck hepatitis virus posttranscriptional regulatory element (WPRE), mouse RNA transport element (RTE), constitutive transport element (CTE) of the simian retrovirus type 1 (SRV-1), the CTE from the Mason-Pfizer monkey virus (MPMV), and the 5' untranslated region of the human heat shock protein 70 (Hsp70 5'UTR). In some embodiments, the rAAV vector comprises a woodchuck hepatitis virus posttranscriptional regulatory element (WPRE). In some aspects, the WPRE can be a mutant WRPE. In some aspects, the WPRE comprises the following sequence:

(SEQ ID NO: 6)
AATCAACCTCTGGATTACAAAATTTGTGAAAGATTGACTGGTATTCTTA

ACTATGTTGCTCCTTTTACGCTATGTGGATACGCTGCTTTAATGCCTTT

GTATCATGCTATTGCTTCCCGTATGGCTTTCATTTTCTCCTCCTTGTAT

AAATCCTGGTTGCTGTCTCTTTATGAGGAGTTGTGGCCCGTTGTCAGGC

AACGTGGCGTGGTGTGCACTGTGTTTGCTGACGCAACCCCCACTGGTTG

GGGCATTGCCACCACCTGTCAGCTCCTTTCCGGGACTTTCGCTTTCCCC

CTCCCTATTGCCACGGCGGAACTCATCGCCGCCTGCCTTGCCCGCTGCT

GGACAGGGGCTCGGCTGTTGGGCACTGACAATTCCGTGGTGTTGTCGGG

GAAATCATCGTCCTTTCCTTGGCTGCTCGCCTGTGTTGCCACCTGGATT

CTGCGCGGGACGTCCTTCTGCTACGTCCCTTCGGCCCTCAATCCAGCGG

ACCTTCCTTCCCGCGGCCTGCTGCCGGCTCTGCGGCCTCTTCCGCGTCT

TCGCCTTCGCCCTCAGACGAGTCGGATCTCCCTTTGGGCCGCCTCCCCG

C.

In some aspects, a polyadenylation sequence can be inserted following the transgene sequences and optionally before a 3' AAV ITR sequence. A rAAV construct useful in the disclosure can also contain an intron, desirably located between the promoter/enhancer sequence and the transgene. In certain embodiments the polyA signal sequence is a rabbit beta globin poly A sequence having the nucleotide sequence as follows:

(SEQ ID NO: 7)
GATCTTTTTCCCTCTGCCAAAAATTATGGGGACATCATGAAGCCCCTTG

AGCATCTGACTTCTGGCTAATAAAGGAAATTTATTTTCATTGCAATAGT

GTGTTGGAATTTTTTGTGTCTCTCACTCG.

Figure 8:
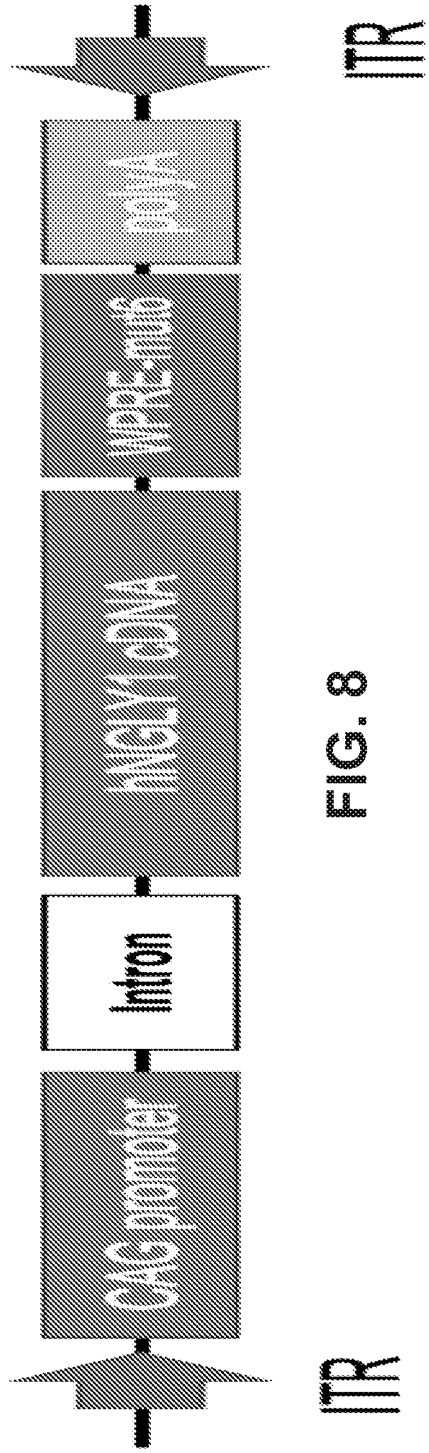
FIG. 8 is a schematic representation of AAV9NGLY1 expression vector GS-100. Inverted terminal repeat (ITR), CMV enhancer/Chicken B-actin promoter combination (CAG), codon optimized human NGLY1 cDNA (hNGLY1cDNA), mutated woodchuck hepatitis virus post-transcriptional regulatory element (WPRE-mut6); and rabbit beta-globin polyadenylation signal (polyA).

In certain embodiments provided herein, the gene expression cassette construct comprises or consists of elements arranged as follows:

CAG promoter—Chimeric Intron Sequence—Codon Optimized NGLY1 coding sequence (SEQ ID NO: 1)-WPRE-Mut6 sequence-Rabbit Beta Globin PolyA signal Sequence. The construct is depicted in FIG. 8. The nucleotide sequence of the gene expression cassette from CAG promoter to polyA signal sequence is as follows:

(SEQ ID NO: 8)
CTAGTCGACATTGATTATTGACTAGTTATTAATAGTAATCAATTACGGGGTCATTAGTTCATAGCCCATATATGGAGTT

CCGCGTTACATAACTTACGGTAAATGGCCCGCCTGGCTGACCGCCCAACGACCCCCGCCCATTGACGTCAATAATGACG

TATGTTCCCATAGTAACGCCAATAGGGACTTTCCATTGACGTCAATGGGTGGAGTATTTACGGTAAACTGCCCACTTGG

CAGTACATCAAGTGTATCATATGCCAAGTACGCCCCCTATTGACGTCAATGACGGTAAATGGCCCGCCTGGCATTATGC

CCAGTACATGACCTTATGGGACTTTCCTACTTGGCAGTACATCTACGTATTAGTCATCGCTATTACCATGTCGAGGACG

CGTCCACGTTCTGCTTCACTCTCCCCATCTCCCCCCCCTCCCCACCCCCAATTTTGTATTTATTTATTTTTTAATTATT

TTGTGCAGCGATGGGGGCGGGGGGGGGGGGGCGCGCCAGGCGGGGCGGGGCGGGGCGAGGGGCGGGGCGGGGCGAGGC

GGAGAGGTGCGGCGGCAGCCAATCAGAGCGGCGCGCTCCGAAAGTTTCCTTTTATGGCGAGGCGGCGGCGGCGGCGGCC

CTATAAAAAGCGAAGCGCGCGGCGGGCGGGAGCAAGCTTTATTGCGGTAGTTTATCACAGTTAAATTGCTAACGCAGTC

AGTGCTTCTGACACAACAGTCTCGAACTTAAGCTGCAGAAGTTGGTCGTGAGGCACTGGGCAGGTAAGTATCAAGGTTA

CAAGACAGGTTTAAGGAGACCAATAGAAACTGGGCTTGTCGAGACAGAGAAGACTCTTGCGTTTCTGATAGGCACCTAT

-continued

TGGTCTTACTGACATCCACTTTGCCTTTCTCTCCACAGGCAGTGTCCACTCCCAGTTCAATTACAGCTCTTAAGGCTAG
AGTACTTAATACGACTCACTATAGGAATTCGCCACCATGGCCGCTGCTGCCCTGGGATCATCAAGTGGGTCCGCTTCAC
CTGCCGTCGCCGAACTGTGCCAGAACACCCCCGAAACCTTCCTGGAGGCATCCAAGCTGCTGCTGACCTACGCCGACAA
CATCCTGCGCAATCCAAACGATGAGAAGTATCGCTCCATCAGGATCGGCAATACCGCCTTCTCTACAAGGCTGCTGCCC
GTGAGGGGAGCAGTGGAGTGCCTGTTCGAGATGGGCTTTGAGGAGGGCGAGACACACCTGATCTTTCCCAAGAAGGCCA
GCGTGGAGCAGCTGCAGAAGATCAGGGACCTGATCGCCATCGAGAGAAGCTCCCGGCTGGATGGCTCTAACAAGAGCCA
CAAGGTGAAGTCTAGCCAGCAGCCTGCAGCAAGCACACAGCTGCCTACCACACCATCCTCTAATCCATCCGGCCTGAAC
CAGCACACCAGGAATAGACAGGGACAGAGCTCCGACCCACCTAGCGCCTCCACAGTGGCAGCCGATTCTGCCATCCTGG
AGGTGCTGCAGAGCAACATCCAGCACGTGCTGGTGTACGAGAATCCAGCCCTGCAGGAGAAGGCCCTGGCATGCATCCC
AGTGCAGGAGCTGAAGCGGAAGAGCCAGGAGAAGCTGTCCAGGGCAAGGAAGCTGGACAAGGGCATCAATATCAGCGAC
GAGGATTTCCTGCTGCTGGAGCTGCTGCACTGGTTTAAGGAGGAGTTCTTTCACTGGGTGAACAATGTGCTGTGCTCCA
AGTGTGGCGGCCAGACCAGGAGCAGAGATCGGTCCCTGCTGCCTTCTGACGATGAGCTGAAGTGGGGCGCCAAGGAGGT
GGAGGACCACTACTGCGATGCCTGTCAGTTCTCCAACCGCTTTCCCAGGTATAACAATCCTGAGAAGCTGCTGGAGACA
AGATGCGGCCGGTGTGGCGAGTGGGCCAATTGTTTCACACTGTGCTGTAGAGCCGTGGGCTTTGAGGCCAGATACGTGT
GGGACTATACCGATCACGTGTGGACAGAGGTGTACTCTCCCAGCCAGCAGAGATGGCTGCACTGCGACGCCTGTGAGGA
CGTGTGCGATAAGCCTCTGCTGTACGAGATCGGCTGGGGCAAGAAGCTGTCTTATGTGATCGCCTTCAGCAAGGACGAG
GTGGTGGATGTGACCTGGCGGTATAGCTGTAAGCACGAGGAAGTGATCGCCAGGAGAACCAAGGTGAAGGAGGCCCTGC
TGCGCGACACAATCAATGGCCTGAACAAGCAGAGGCAGCTGTTCCTGTCCGAGAACCGGCGCAAGGAGCTGCTGCAGAG
GATCATCGTGGAGCTGGTGGAGTTTATCTCTCCTAAGACCCCAAAGCCAGGAGAGCTGGGAGGAAGGATCTCCGGCTCT
GTGGCCTGGCGCGTGGCCAGGGGCGAGATGGGCCTGCAGAGGAAGGAGACACTGTTCATCCCATGCGAGAACGAGAAGA
TCTCTAAGCAGCTGCACCTGTGCTACAATATCGTGAAGGACAGATATGTGCGGGTGTCCAACAATAACCAGACCATCTC
TGGCTGGGAGAACGGCGTGTGGAAGATGGAGAGCATCTTTAGAAAGGTGGAGACAGATTGGCACATGGTGTACCTGGCC
CGGAAGGAGGGCTCTAGCTTCGCCTATATCAGCTGGAAGTTTGAGTGTGGCTCCGTGGGCCTGAAGGTGGACAGCATCT
CCATCAGAACCTCCTCTCAGACATTCCAGACCGGCACAGTGGAGTGGAAGCTGAGGTCCGATACCGCCCAGGTGGAGCT
GACAGGCGACAATTCCCTGCACTCTTACGCCGATTTCTCTGGCGCCACCGAAGTGATCCTGGAGGCAGAGCTGAGCAGG
GGCGACGGCGATGTGGCCTGGCAGCACACACAGCTGTTTAGGCAGAGCCTGAACGACCACGAGGAGAATTGCCTGGAGA
TTATTATCAAGTTTTCCGACCTGTGACTCGAGAATCAACCTCTGGATTACAAAATTTGTGAAAGATTGACTGGTATTCT
TAACTATGTTGCTCCTTTTACGCTATGTGGATACGCTGCTTTAATGCCTTTGTATCATGCTATTGCTTCCCGTATGGCT
TTCATTTTCTCCTCCTTGTATAAATCCTGGTTGCTGTCTCTTTATGAGGAGTTGTGGCCCGTTGTCAGGCAACGTGGCG
TGGTGTGCACTGTGTTTGCTGACGCAACCCCCACTGGTTGGGGCATTGCCACCACCTGTCAGCTCCTTTCCGGGACTTT
CGCTTTCCCCCTCCCTATTGCCACGGCGGAACTCATCGCCGCCTGCCTTGCCCGCTGCTGGACAGGGGCTCGGCTGTTG
GGCACTGACAATTCCGTGGTGTTGTCGGGGAAATCATCGTCCTTTCCTTGGCTGCTCGCCTGTGTTGCCACCTGGATTC
TGCGCGGGACGTCCTTCTGCTACGTCCCTTCGGCCCTCAATCCAGCGGACCTTCCTTCCCGCGGCCTGCTGCCGGCTCT
GCGGCCTCTTCCGCGTCTTCGCCTTCGCCCTCAGACGAGTCGGATCTCCCTTTGGGCCGCCTCCCCGCATCGATGATCT
TTTTCCCTCTGCCAAAAATTATGGGGACATCATGAAGCCCCTTGAGCATCTGACTTCTGGCTAATAAAGGAAATTTATT
TTCATTGCAATAGTGTGTTGGAATTTTTTGTGTCTCTCACTCG.

Recombinant AAVs. In some aspects, the isolated nucleic acids disclosed herein can be recombinant adeno-associated viruses (rAAVs) vectors. In some aspects, the rAAV vectors described herein can be composed of, at a minimum, a transgene and its regulatory sequences, and 5' and 3' AAV inverted terminal repeats (ITRs). It is this recombinant AAV vector that can be packaged into a capsid protein and delivered to a selected target cell. In some aspects, the transgene can be a nucleic acid sequence, heterologous to the vector sequences, which encodes a polypeptide, protein, functional RNA molecule or other gene product, of interest. In some aspects, the nucleic acid coding sequence can be operatively linked to regulatory components in a manner which permits transgene transcription, translation, and/or expression in a cell of a target tissue.

In some aspects, an isolated nucleic acid as described herein comprises a region (e.g., a first region) comprising a first adeno-associated virus (AAV) inverted terminal repeat (ITR), or a variant thereof and a second region comprising a transgene encoding NGLY1. The isolated nucleic acid (e.g., the recombinant AAV vector) can be packaged into a capsid protein and administered to a subject and/or delivered to a selected target cell. The transgene can also comprise a region encoding, for example, a protein and/or an expression control sequence (e.g., a poly-A tail).

Also disclosed herein are vectors comprising a single, cis-acting wild-type ITR. In some aspects, the ITR can be a 5' ITR. In some aspects, the ITR can be a 3' ITR. ITR sequences are about 145 bp in length. In some aspects, the entire sequences encoding the ITR(s) can be used in the molecule, although some degree of minor modification of these sequences is permissible. In some aspects, an ITR can be mutated at its terminal resolution site (TR), which inhibits replication at the vector terminus where the TR has been mutated and results in the formation of a self-complementary AAV. In some aspects, a "cis-acting" plasmid containing the transgene, in which the selected transgene sequence and associated regulatory elements can be flanked by the 5' AAV ITR sequence and a 3' hairpin-forming RNA sequence, can be used. AAV ITR sequences can be obtained from any known AAV, including presently identified mammalian AAV types. In some aspects, an ITR sequence can be an AAV2, AAV3, AAV4, AAV5, AAV6, AAV7, AAV8, AAVrh8, AAV9, AAV10, and/or AAVrh10 ITR sequence. In some aspects, the AAV ITR sequences are AAV2.

In certain aspects, the recombinant AAV genome containing the transgene contains the elements as follows: AAV2ITR-CAG Promoter-NGLY1 coding sequence-polyA signal sequence-AAV2ITR sequence. In particular aspects, the construct further comprises an intron and or a WPRE sequence. In further specific embodiments, the construct contains AAV2 ITR sequence-CAG promoter-Intron Sequence-NGLY1 codon optimized coding sequence-WPRE Mut6 sequence-Rabbit Beta globin polyA signal Sequence-AAV2 ITR sequence. In particular embodiments, the nucleotide sequence of the construct is as follows:

(SEQ ID NO: 9)

```
CCTGCAGGCAGCTGCGCGCTCGCTCGCTCACTGAGGCCGCCCGGGCGTCGGGCGACCTTTGGTCGCCCGGCCTCAGTGAGCGA

GCGAGCGCGCAGAGAGGGAGTGGCCAACTCCATCACTAGGGGTTCCTGCGGCCGCCTAGTCGACATTGATTATTGACTAGTTA

TTAATAGTAATCAATTACGGGGTCATTAGTTCATAGCCCATATATGGAGTTCCGCGTTACATAACTTACGGTAAATGGCCCGC

CTGGCTGACCGCCCAACGACCCCCGCCCATTGACGTCAATAATGACGTATGTTCCCATAGTAACGCCAATAGGGACTTTCCAT

TGACGTCAATGGGTGGAGTATTTACGGTAAACTGCCCACTTGGCAGTACATCAAGTGTATCATATGCCAAGTACGCCCCCTAT

TGACGTCAATGACGGTAAATGGCCCGCCTGGCATTATGCCCAGTACATGACCTTATGGGACTTTCCTACTTGGCAGTACATCT

ACGTATTAGTCATCGCTATTACCATGTCGAGGACGCGTCCACGTTCTGCTTCACTCTCCCCATCTCCCCCCCCTCCCCACCCC

CAATTTTGTATTTATTTATTTTTTAATTATTTTGTGCAGCGATGGGGGCGGGGGGGGGGGGCGCGCGCCAGGCGGGGCGGGGC

GGGGCGAGGGGGGGGCGGGGCGAGGCGGAGAGGTGCGGCGGCAGCCAATCAGAGCGGCGCGCTCCGAAAGTTTCCTTTTATGG

CGAGGCGGCGGCGGCGGCGGCCCTATAAAAAGCGAAGCGCGCGGCGGGCGGGAGCAAGCTTTATTGCGGTAGTTTATCACAGT

TAAATTGCTAACGCAGTCAGTGCTTCTGACACAACAGTCTCGAACTTAAGCTGCAGAAGTTGGTCGTGAGGCACTGGGCAGGT

AAGTATCAAGGTTACAAGACAGGTTTAAGGAGACCAATAGAAACTGGGCTTGTCGAGACAGAGAAGACTCTTGCGTTTCTGAT

AGGCACCTATTGGTCTTACTGACATCCACTTTGCCTTTCTCTCCACAGGCAGTGTCCACTCCCAGTTCAATTACAGCTCTTAA

GGCTAGAGTACTTAATACGACTCACTATAGGAATTCGCCACCATGGCCGCTGCTGCCCTGGGATCATCAAGTGGGTCCGCTTC

ACCTGCCGTCGCCGAACTGTGCCAGAACACCCCCGAAACCTTCCTGGAGGCATCCAAGCTGCTGCTGACCTACGCCGACAACA

TCCTGCGCAATCCAAACGATGAGAAGTATCGCTCCATCAGGATCGGCAATACCGCCTTCTCTACAAGGCTGCTGCCCGTGAGG

GGAGCAGTGGAGTGCCTGTTCGAGATGGGCTTTGAGGAGGGCGAGACACACCTGATCTTTCCCAAGAAGGCCAGCGTGGAGCA

GCTGCAGAAGATCAGGGACCTGATCGCCATCGAGAGAAGCTCCCGGCTGGATGGCTCTAACAAGAGCCACAAGGTGAAGTCTA

GCCAGCAGCCTGCAGCAAGCACACAGCTGCCTACCACACCATCCTCTAATCCATCCGGCCTGAACCAGCACACCAGGAATAGA

CAGGGACAGAGCTCCGACCCACCTAGCGCCTCCACAGTGGCAGCCGATTCTGCCATCCTGGAGGTGCTGCAGAGCAACATCCA

GCACGTGCTGGTGTACGAGAATCCAGCCCTGCAGGAGAAGGCCCTGGCATGCATCCCAGTGCAGGAGCTGAAGCGGAAGAGCC

AGGAGAAGCTGTCCAGGGCAAGGAAGCTGGACAAGGGCATCAATATCAGCGACGAGGATTTCCTGCTGCTGGAGCTGCTGCAC
```

-continued

TGGTTTAAGGAGGAGTTCTTTCACTGGGTGAACAATGTGCTGTGCTCCAAGTGTGGCGGCCAGACCAGGAGCAGAGATCGGTC

CCTGCTGCCTTCTGACGATGAGCTGAAGTGGGGCGCCAAGGAGGTGGAGGACCACTACTGCGATGCCTGTCAGTTCTCCAACC

GCTTTCCCAGGTATAACAATCCTGAGAAGCTGCTGGAGACAAGATGCGGCCGGTGTGGCGAGTGGGCCAATTGTTTCACACTG

TGCTGTAGAGCCGTGGGCTTTGAGGCCAGATACGTGTGGGACTATACCGATCACGTGTGGACAGAGGTGTACTCTCCCAGCCA

GCAGAGATGGCTGCACTGCGACGCCTGTGAGGACGTGTGCGATAAGCCTCTGCTGTACGAGATCGGCTGGGGCAAGAAGCTGT

CTTATGTGATCGCCTTCAGCAAGGACGAGGTGGTGGATGTGACCTGGCGGTATAGCTGTAAGCACGAGGAAGTGATCGCCAGG

AGAACCAAGGTGAAGGAGGCCCTGCTGCGCGACACAATCAATGGCCTGAACAAGCAGAGGCAGCTGTTCCTGTCCGAGAACCG

GCGCAAGGAGCTGCTGCAGAGGATCATCGTGGAGCTGGTGGAGTTTATCTCTCCTAAGACCCCAAAGCCAGGAGAGCTGGGAG

GAAGGATCTCCGGCTCTGTGGCCTGGCGCGTGGCCAGGGGCGAGATGGGCCTGCAGAGGAAGGAGACACTGTTCATCCCATGC

GAGAACGAGAAGATCTCTAAGCAGCTGCACCTGTGCTACAATATCGTGAAGGACAGATATGTGCGGGTGTCCAACAATAACCA

GACCATCTCTGGCTGGGAGAACGGCGTGTGGAAGATGGAGAGCATCTTTAGAAAGGTGGAGACAGATTGGCACATGGTGTACC

TGGCCCGGAAGGAGGGCTCTAGCTTCGCCTATATCAGCTGGAAGTTTGAGTGTGGCTCCGTGGGCCTGAAGGTGGACAGCATC

TCCATCAGAACCTCCTCTCAGACATTCCAGACCGGCACAGTGGAGTGGAAGCTGAGGTCCGATACCGCCCAGGTGGAGCTGAC

AGGCGACAATTCCCTGCACTCTTACGCCGATTTCTCTGGCGCCACCGAAGTGATCCTGGAGGCAGAGCTGAGCAGGGGCGACG

GCGATGTGGCCTGGCAGCACACACAGCTGTTTAGGCAGAGCCTGAACGACCACGAGGAGAATTGCCTGGAGATTATTATCAAG

TTTTCCGACCTGTGACTCGAGAATCAACCTCTGGATTACAAAATTTGTGAAAGATTGACTGGTATTCTTAACTATGTTGCTCC

TTTTACGCTATGTGGATACGCTGCTTTAATGCCTTTGTATCATGCTATTGCTTCCCGTATGGCTTTCATTTTCTCCTCCTTGT

ATAAATCCTGGTTGCTGTCTCTTTATGAGGAGTTGTGGCCCGTTGTCAGGCAACGTGGCGTGGTGTGCACTGTGTTTGCTGAC

GCAACCCCCACTGGTTGGGGCATTGCCACCACCTGTCAGCTCCTTTCCGGGACTTTCGCTTTCCCCCTCCCTATTGCCACGGC

GGAACTCATCGCCGCCTGCCTTGCCCGCTGCTGGACAGGGGCTCGGCTGTTGGGCACTGACAATTCCGTGGTGTTGTCGGGGA

AATCATCGTCCTTTCCTTGGCTGCTCGCCTGTGTTGCCACCTGGATTCTGCGCGGGACGTCCTTCTGCTACGTCCCTTCGGCC

CTCAATCCAGCGGACCTTCCTTCCCGCGGCCTGCTGCCGGCTCTGCGGCCTCTTCCGCGTCTTCGCCTTCGCCCTCAGACGAG

TCGGATCTCCCTTTGGGCCGCCTCCCCGCATCGATGATCTTTTTCCCTCTGCCAAAAATTATGGGGACATCATGAAGCCCCTT

GAGCATCTGACTTCTGGCTAATAAAGGAAATTTATTTTCATTGCAATAGTGTGTTGGAATTTTTTGTGTCTCTCACTCGCGGA

CCGAGCGGCCGCAGGAACCCCTAGTGATGGAGTTGGCCACTCCCTCTCTGCGCGCTCGCTCGCTCACTGAGGCCGGGCGACCA

AAGGTCGCCCGACGCCCGGGCTTTGCCCGGGCGGCCTCAGTGAGCGAGCGAGCGCGCAGCTGCCTGCAGG.

In some aspects, a rAAV vector can be a self-complementary vector that comprises a nucleic acid sequence encoding a NGLY1 protein or a portion thereof.

In particular aspects, the rAAV is an AAV9 serotype. Other serotypes with tropism for CNS cells may also be used. In particular embodiments, the rAAV has a capsid having the amino acid sequence of the AAV9 capsid, or that is 99%, 98%, 95%, 90% or 85% identical to the AAV9 capsid. The AAV9 capsid has the amino acid sequence as follows:

(SEQ ID NO: 10)

MAADGYLPDW LEDNLSEGIR EWWALKPGAP QPKANQQHQD

NARGLVLPGY KYLGPGNGLD KGEPVNAADA AALEHDKAYD

QQLKAGDNPY LKYNHADAEF QERLKEDTSF GGNLGRAVFQ

AKKRLLEPLG LVEEAAKTAP GKKRPVEQSP QEPDSSAGIG

KSGAQPAKKR LNFGQTGDTE SVPDPQPIGE PPAAPSGVGS

LTMASGGGAP VADNNEGADG VGSSSGNWHC DSQWLGDRVI

-continued

TTSTRTWALP TYNNHLYKQI SNSTSGGSSN DNAYFGYSTP

WGYFDFNRFH CHFSPRDWQR LINNNWGFRP KRLNFKLFNI

QVKEVTDNNG VKTIANNLTS TVQVFTDSDY QLPYVLGSAH

EGCLPPFPAD VFMIPQYGYL TLNDGSQAVG RSSFYCLEYF

PSQMLRTGNN FQFSYEFENV PFHSSYAHSQ SLDRLMNPLI

DQYLYYLSKT INGSGQNQQT LKFSVAGPSN MAVQGRNYIP

GPSYRQQRVS TTVTQNNNSE FAWPGASSWA LNGRNSLMNP

GPAMASHKEG EDRFFPLSGS LIFGKQGTGR DNVDADKVMI

TNEEEIKTTN PVATESYGQV ATNHQSAQAQ AQTGWVQNQG

ILPGMVWQDR DVYLQGPIWA KIPHTDGNFH PSPLMGGFGM

KHPPPQILIK NTPVPADPPT AFNKDKLNSF ITQYSTGQVS

VEIEWELQKE NSKRWNPEIQ YTSNYYKSNN VEFAVNTEGV

YSEPRPIGTR YLTRNL.

In some aspects, the isolated nucleic acids and/or rAAVs described herein can be modified and/or selected to enhance the targeting of the isolated nucleic acids and/or rAAVs to a target tissue (e.g., CNS). Non-limiting methods of modifications and/or selections include AAV capsid serotypes (e.g., AAV9), tissue-specific promoters, and/or targeting peptides. In some aspects, the isolated nucleic acids and rAAVs disclosed herein can comprise AAV capsid serotypes with enhanced targeting to CNS tissues (e.g., AAV9). In some aspects, the isolated nucleic acids and rAAVs described herein can comprise tissue-specific promoters. In some aspects, the isolated nucleic acids and rAAVs described herein can comprise AAV capsid serotypes with enhanced targeting to CNS tissues and tissue-specific promoters. While AAV9 targets CNS tissue, the rAAV9 vectors may also transduce other non-CNS tissues and, thus, the transgenes, under the control of a promoter such as the CAG promoter may be expressed both in the CNS and other tissues outside the CNS. In some aspects, CNS delivery of the constructs disclosed herein can target CNS tissue resulting in CNS expression of NGLY1 but also lead to NGLY1 expression in peripheral tissues including but not limited to liver and heart.

In some aspects, the disclosure provides isolated AAVs. As used herein with respect to AAVs, the term "isolated" refers to an AAV that has been artificially obtained or produced. Isolated AAVs can be produced using recombinant methods. Such AAVs are referred to herein as "recombinant AAVs". Recombinant AAVs (rAAVs) preferably have tissue-specific targeting capabilities, such that a transgene of the rAAV can be delivered specifically to one or more predetermined tissue(s). The AAV capsid can be an important element in determining these tissue-specific targeting capabilities. Thus, an rAAV having a capsid appropriate for the tissue being targeted can be selected. In some aspects, the rAAV comprises an AAV1, AAV2, AAV3, AAV4, AAV5, AAV6, AAV7, AAV8, AAVrh8, AAV9, AAV10, AAVrh10, or AAV.PHPB capsid protein, or a protein having substantial homology thereto. In some aspects, the rAAV comprises an AAV9 capsid protein. In some aspects, the rAAV comprises an AAVPHP.B capsid protein.

In some aspects, the rAAVs described herein can be pseudotyped rAAVs. Pseudotyping is the process of producing viruses or viral vectors in combination with foreign viral envelope proteins. The result is a pseudotyped virus particle. With this method, the foreign viral envelope proteins can be used to alter host tropism or an increased/decreased stability of the virus particles. In some aspects, a pseudotyped rAAV comprises nucleic acids from two or more different AAVs, wherein the nucleic acid from one AAV encodes a capsid protein and the nucleic acid of at least one other AAV encodes other viral proteins and/or the viral genome. In some aspects, a pseudotyped rAAV refers to an AAV comprising an inverted terminal repeats (ITRs) of one AAV serotype and an capsid protein of a different AAV serotype. For example, a pseudotyped AAV vector containing the ITRs of serotype X encapsidated with the proteins of Y can be designated as AAVX/Y (e.g., AAV2/1 has the ITRs of AAV2 and the capsid of AAV1). In some aspects, pseudotyped rAAVs can be useful for combining the tissue-specific targeting capabilities of a capsid protein from one AAV serotype with the viral DNA from another AAV serotype, thereby allowing targeted delivery of a transgene to a target tissue.

Methods for obtaining recombinant AAVs having a desired capsid protein are well known in the art. (See, for example, US Patent Application Publication Number US 2003/0138772, the contents of which are incorporated herein by reference in their entirety). Typically the methods involve culturing a host cell which contains a nucleic acid sequence encoding an AAV capsid protein or fragment thereof, a functional rep gene; a recombinant AAV vector composed of, AAV inverted terminal repeats (ITRs) and a transgene; and sufficient helper functions to permit packaging of the recombinant AAV vector into the AAV capsid proteins. Typically, capsid proteins are structural proteins encoded by the cap gene of an AAV. In some aspects, AAVs comprise three capsid proteins, virion proteins 1 to 3 (named VP1, VP2 and VP3), which are transcribed from a single cap gene via alternative splicing. In some aspects, the molecular weights of VP1, VP2 and VP3 are respectively about 87 kDa, about 72 kDa and about 62 kDa. In some aspects, upon translation, capsid proteins form a spherical 60-mer protein shell around the viral genome. In some aspects, capsid proteins protect a viral genome, deliver a genome and/or interact with a host cell. In some aspects, capsid proteins deliver the viral genome to a host in a tissue specific manner.

In some aspects, the AAV capsid protein can be an AAV serotype selected from the group consisting of AAV3, AAV4, AAV5, AAV6, AAV8, AAVrh8 AAV9, AAV10 and AAVrh10. In some aspects, the AAV capsid protein can be an AAVrh8, AAVrh10, or AAV.PHPB serotype. In some aspects, the AAV capsid protein can be an AAVrh8 serotype. In some aspects, the AAV capsid protein can be an AAV9 serotype. In some aspects, the AAV capsid protein can be an AAV.PHPB serotype.

In some aspects, components to be cultured in the host cell to package a rAAV vector in an AAV capsid can be provided to the host cell in trans. Alternatively, any one or more of the required components (e.g., recombinant AAV vector, rep sequences, cap sequences, and/or helper functions) can be provided by a stable host cell which has been engineered to contain one or more of the required components using methods known to those of skill in the art.

In some aspects, such a stable host cell can contain the required component(s) under the control of an inducible promoter. However, the required component(s) can be under the control of a constitutive promoter. Examples of suitable inducible and constitutive promoters are provided herein, in the discussion of regulatory elements suitable for use with the transgene. In some aspects, a selected stable host cell can contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

The recombinant AAV vector, rep sequences, cap sequences, and helper functions useful for producing the rAAV described herein can be delivered to the packaging host cell using any appropriate genetic element (vector). The selected genetic element can be delivered by any suitable method, including those described herein. The methods used to construct any of compositions disclosed herein are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al, J. Virol., 70:520-532 (1993) and U.S. Pat. No. 5,478,745.

In some aspects, recombinant AAVs can be produced using the triple transfection method (described in detail in U.S. Pat. No. 6,001,650). Typically, the recombinant AAVs can be produced by transfecting a host cell with a recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. In some aspects, the AAV helper function vector can support efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

Cells. Disclosed herein are transfected host cells. The term "transfection" is used to refer to the uptake of foreign DNA by a cell, and a cell has been "transfected" when exogenous DNA has been introduced through the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

As used herein, the term "host cell" refers to any cell that harbors, or is capable of harboring, a substance of interest. Often a host cell can be a mammalian cell (e.g., a non-human primate, rodent, or human cell). In some aspects, the host cell can be a mammalian cell, a yeast cell, a bacterial cell, an insect cell, a plant cell, or a fungal cell. A host cell can be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein can refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

Provided herein are host cells for production of rAAV, particularly rAAV9 particles, containing a genome comprising a transgene encoding NGLY1 (including the nucleotide sequence of SEQ ID NO: 1) operably linked to regulatory elements that promote expression of the NGLY1 transgene in vivo. For example, operably linked to a CAG promoter and a polyA signal sequence. The gene expression cassette may have the nucleotide sequence of SEQ ID NO: 8 and may include flanking ITR sequences, for example, the entire construct with the flanking ITR sequences may have the nucleotide sequence of SEQ ID NO: 9.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the term "recombinant cell" refers to a cell into which an exogenous DNA segment, such as DNA segment that leads to the transcription of a biologically-active polypeptide or production of a biologically active nucleic acid such as an RNA, has been introduced.

Method of Treatment

Provided are methods of treating a subject suffering from NGLY1 deficiency by administration of an rAAV comprising a transgene encoding NGLY1 and engineered to express the NGLY1 protein in the CNS and other tissue(s), in particular an rAAV9 vector comprising, for example, the construct disclosed herein, such as comprising the nucleotide sequence of SEQ ID NO: 1. The rAAV encoding the NGLY1 protein may be administered by any method known in the art. In some aspects, the rAAV is delivered by intracerebroventricular administration or intra cisterna magna (ICM) administration. In some aspects, methods for delivering a transgene to CNS tissue in a subject can comprise co-administering of an effective amount of a rAAV by two different administration routes, e.g., by intracerebroventricular administration and by intravenous administration. Co-administration of the rAAV can be performed at approximately the same time, or different times. In some aspects, the rAAV is delivered at an appropriate dosage, for example $6\times10^{6}$ to $6\times10^{16}$ genome copies/kg (or alternatively a dosage assessed according to brain volume or CSF volume for brain administration). The combination of the rAAV serotype, including AAV9, the regulatory elements, and mode of administration result in therapeutically effective delivery of the NGLY1 protein to CNS tissues as well as other peripheral tissues that promote the therapeutic benefit of the administration.

In some aspects, the CNS tissue to be targeted can be cortex, hippocampus, thalamus, hypothalamus, cerebellum, brain stem, cervical spinal cord, thoracic spinal cord, lumbar spinal cord, or a combination thereof. In some aspects, the tissue to be targeted is the PNS. The administration route for targeting CNS tissue can depend on the AAV serotype. In some aspects, the administration route can be intravascular injection when the AAV serotype is AAVPHP.B, AAV1, AAV6, AAV6.2, AAV7, AAV8, AAV9, rh.10, rh.39, rh.43 and CSp3. In some aspects, the administration route can be intrathecal and/or intracerebral injection when the AAV serotype is AAVPHP.B, AAV1, AAV2, AAV5, AAV6, AAV6.2, AAV7, AAV8, AAV9, rh.10, rh.39, rh.43 and CSp3. In some aspects, the administration route can be intracerebroventricular or ICM administration when the AAV serotype is AAVPHP.B, AAV1, AAV6, AAV6.2, AAV7, AAV8, AAV9, rh.10, rh.39, rh.43 and CSp3. In some aspects, the administration route can be intracerebroventricular or ICM administration when the AAV serotype is AAVPHP.B, AAV1, AAV2, AAV5, AAV6, AAV6.2, AAV7, AAV8, AAV9, rh.10, rh.39, rh.43 and CSp3.

In some aspects, the composition (e.g., a pharmaceutical composition) can comprise an rAAV comprising a nucleic acid encoding a NGLY1. In some aspects, the compositions comprising a recombinant AAV comprising at least one modified genetic regulatory sequence or element can further comprise a pharmaceutically acceptable carrier. Suitable carriers can be selected for the indication for which the rAAV is directed. For example, one suitable carrier includes saline, which may be formulated with a variety of buffering solutions (e.g., phosphate buffered saline). Examples of other suitable carriers include but are not limited to sterile saline, lactose, sucrose, calcium phosphate, gelatin, dextran, agar, pectin, peanut oil, sesame oil, and water. Optionally, the compositions disclosed herein can also include, in addition to the rAAV and carrier(s), other pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

In some aspects, the rAAV is administered in a pharmaceutical composition comprising phosphate buffered saline (PBS), pH 7.3 and 0.001% of a pharmaceutically acceptable non-ionic surfactant, such as, for example, pluronic F-68 (PF68), or other appropriate pharmaceutically acceptable buffers or excipients. The formulation may be frozen until ready for use and then thawed and administered.

In some aspects, the compositions disclosed herein can comprise an rAAV alone, or in combination with one or more other viruses (e.g., a second rAAV encoding having one or more different transgenes). In some aspects, a composition can comprise 1, 2, 3, 4, 5, 6, 7, 8, 9, 10, or more different rAAVs each having one or more different transgenes.

rAAVs can be administered in sufficient amounts to transfect the cells of a desired tissue and to provide sufficient levels of gene transfer and expression without undue adverse effects. In some aspects, acceptable routes of administration include, but are not limited to, direct delivery to the selected organ (e.g., injection into the liver, skeletal muscle), oral, inhalation (including intranasal and intratracheal delivery), intraocular, intravenous, intramuscular, subcutaneous, intradermal, intratumoral, and other parental routes of administration. In some aspects, the route of administration can be by intracerebroventricular injection. Routes of administration may be combined, if desired.

The dose of rAAV virions required to achieve a particular "therapeutic effect," e.g., the units of dose in genome copies/per kilogram of body weight (GC/kg), the units of dose in genome copies per brain volume, and units of dose in genome copies per CSF volume, will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An effective amount of an rAAV is an amount sufficient to target infect an animal, target a desired tissue. The effective amount will depend primarily on factors such as the species, age, weight, health of the subject, and the tissue to be targeted, and may thus vary among animal and tissue. For example, an effective amount of the rAAV can be in the range from about 1 ml to about 100 ml of solution containing from about $10^6$ to $10^{16}$ genome copies (e.g., from $1\times10^6$ to $1\times10^{16}$, inclusive). In methods disclosed herein, the therapeutically effective dose is between $6\times10^{13}$ gc/kg to $6\times10^{14}$ gc/kg, including $7\times10^{13}$ gc/kg, $8\times10^{13}$ gc/kg, $9\times10^{13}$ gc/kg, $1\times10^{14}$ gc/kg, $2\times10^{14}$ gc/kg, $3\times10^{14}$ gc/kg, $4\times10^{14}$ gc/kg, or $5\times10^{14}$ gc/kg (or alternatively, genome copies per brain volume, CSF volume or other measurement appropriate for ICV or ICM delivery). In some aspects, a dosage between about $10^{11}$ to $10^{12}$ per kg or appropriate measurement rAAV genome copies can be appropriate. In some aspects, a dosage of between about $10^{11}$ to $10^{13}$ per kg or appropriate measurement rAAV genome copies can be appropriate. In some aspects, a dosage of between about $10^{11}$ to $10^{14}$ per kg or appropriate measurement rAAV genome copies can be appropriate. In some aspects, a dosage of between about $10^{11}$ to $10^{15}$ per kg or appropriate measurement rAAV genome copies can be appropriate. In some aspects, a dosage of about $1\times10^{14}$ vector genome (vg) copies per kg or appropriate measurement can be appropriate. In some aspects, the dosage can vary or be reduced when specifically targeting one or more brain region(s). In some aspects, a dosage between about $10^7$ to $10^8$ rAAV genome copies per kg or appropriate measurement can be appropriate. In some aspects, a dosage of between about 108 to $10^9$ rAAV genome copies per kg or appropriate measurement can be appropriate. In some aspects, a dosage of between about $10^9$ to $10^{10}$ rAAV genome copies per kg or appropriate measurement can be appropriate. In some aspects, a dosage of between about $10^{10}$ to $10^{11}$ rAAV genome copies per kg or other appropriate measurement can be appropriate.

In some aspects, a potential side-effect for administering an AAV to a subject can be an immune response in the subject to the AAV, including inflammation, and, and may depend on the route of administration, and in particularly, when the administration of an AAV is systemic. In some aspects, a subject can be immunosuppressed prior to administration of one or more rAAVs as described herein.

As used herein, "immunosuppressed" or "immunosuppression" refers to a decrease in the activation or efficacy of an immune response in a subject. Immunosuppression can be induced in a subject using one or more (e.g., multiple, such as 2, 3, 4, 5, or more) agents, including, but not limited to, rituximab, methylprednisolone, prednisolone, sirolimus, immunoglobulin injection, prednisone, methotrexate, and any combination thereof.

In some aspects, methods disclosed herein can further comprise the step of inducing immunosuppression (e.g., administering one or more immunosuppressive agents) in a subject prior to the subject being administered an rAAV (e.g., an rAAV or pharmaceutical composition as disclosed herein). In some aspects, a subject can be immunosuppressed (e.g., immunosuppression is induced in the subject) between about 30 days and about 0 days (e.g., any time between 30 days until administration of the rAAV, inclusive) prior to administration of the rAAV to the subject. In some aspects, the subject can be pretreated with immune suppression agent (e.g., rituximab, sirolimus, and/or prednisone) for at least 7 days.

In some aspects, immunosuppression of a subject maintained during and/or after administration of a rAAV or pharmaceutical composition. In some aspects, a subject can be immunosuppressed (e.g., administered one or more immunosuppressants) for between 1 day and 1 year after administration of the rAAV or pharmaceutical composition.

In some aspects, rAAV compositions can be formulated to reduce aggregation of AAV particles in the composition, particularly where high rAAV concentrations are present (e.g., $10^{13}$ GC/ml or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions are well-known to those of skill in the art, as is the development of suitable dosing and treatment regimens for using the particular compositions described herein in a variety of treatment regimens.

In some aspects, these formulations can contain at least about 0.1% of the active compound or more, although the percentage of the active ingredient(s) may, of course, be varied and can be conveniently be between about 1 or 2% and about 70% or 80% or more of the weight or volume of the total formulation. Naturally, the amount of active compound in each therapeutically-useful composition can be prepared in such a way that a suitable dosage can be obtained in any given unit dose of the compound. Factors such as solubility, bioavailability, biological half-life, route of administration, product shelf life, as well as other pharmacological considerations can be contemplated by one skilled in the art of preparing such pharmaceutical formulations, and as such, a variety of dosages and treatment regimens can be desirable.

In some aspects, it will be desirable to deliver the rAAV-based therapeutic constructs in suitably formulated pharmaceutical compositions as disclosed herein either subcutaneously, intrapancreatically, intranasally, parenterally, intravenously, intramuscularly, intrathecally, or orally, intraperitoneally, intracerebroventricularly, or by inhalation. In some aspects, the administration modalities as described in U.S. Pat. Nos. 5,543,158; 5,641,515 and 5,399,363 (each specifically incorporated herein by reference in its entirety) can be used to deliver rAAVs. In some embodiments, a preferred mode of administration can be by intracerebroventricular injection.

The pharmaceutical forms suitable for injectable use include sterile aqueous solutions or dispersions and sterile powders for the extemporaneous preparation of sterile injectable solutions or dispersions. Dispersions can also be prepared in glycerol, liquid polyethylene glycols, and mixtures thereof and in oils. Under ordinary conditions of storage and use, these preparations contain a preservative to prevent the growth of microorganisms. In many cases the form can be sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, isotonic agents, for example, sugars or sodium chloride can be included. Prolonged absorption of the injectable compositions can be brought about by the use in the compositions of agents delaying absorption, for example, aluminum monostearate and gelatin.

For administration of an injectable aqueous solution, for example, the solution can be suitably buffered, if necessary, and the liquid diluent first rendered isotonic with sufficient saline or glucose. These particular aqueous solutions can be suitable for intravenous, intramuscular, subcutaneous, intracerebroventricular, and intraperitoneal administration. In this connection, a sterile aqueous medium that can be employed will be known to those of skill in the art. For example, one dosage can be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). In particular embodiments, the rAAV is formulated in phosphate buffered saline (PBS) at pH 7.3, including 0.001% of a pharmaceutically acceptable non-ionic surfactant, such as, for example, PF68. Some variation in dosage will necessarily occur depending on the condition of the host. The person responsible for administration will, in any event, determine the appropriate dose for the individual host.

Sterile injectable solutions can be prepared by incorporating the active rAAV in the required amount in the appropriate solvent with various of the other ingredients enumerated herein, as required, followed by filtered sterilization. Generally, dispersions can be prepared by incorporating the various sterilized active ingredients into a sterile vehicle which contains the basic dispersion medium and the required other ingredients from those enumerated above. In the case of sterile powders for the preparation of sterile injectable solutions, the methods of preparation can be vacuum-drying and freeze-drying techniques which yield a powder of the active ingredient plus any additional desired ingredient from a previously sterile-filtered solution thereof.

The rAAV compositions disclosed herein can be also be formulated in a neutral or salt form. Pharmaceutically-acceptable salts, include the acid addition salts (formed with the free amino groups of the protein) and which can be formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations can be easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes can be formulated for delivery either encapsulated in a lipid particle, a liposome, a vesicle, a nanosphere, or a nanoparticle or the like.

Such formulations can be used for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes can be formed from phospholipids that can be dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Angstroms, containing an aqueous solution in the core.

Alternatively, nanocapsule formulations of the rAAV can be used. Nanocapsules can generally entrap substances in a stable and reproducible way. To avoid side effects due to intracellular polymeric overloading, such ultrafine particles (sized around 0.1 p.m) should be designed using polymers able to be degraded in vivo. Biodegradable polyalkyl-cyanoacrylate nanoparticles that meet these requirements are contemplated for use.

In addition to the methods of delivery described above, the following techniques can also be used as alternative methods of delivering the rAAV compositions to a host. Sonophoresis (e.g., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

In some aspects, the methods can include administering one or more additional therapeutic agents to a subject who has been administered an rAAV or pharmaceutical composition as described herein.

Disclosed herein are methods of treating a NGLYI deficiency by administration of an rAAV vector described herein that contains a transgene encoding NGLY1 engineered to be expressed in the CNS, and may be an AAV9 serotype. NGLY1 deficiency, which results from loss-of-function mutations in the NGLY1 gene is an ultra-rare genetic disorder, and patients suffer from developmental delay, seizures, lack of tears, elevated liver transaminases in childhood, and movement disorder. In some aspects, gene replacement therapy as described herein that can be useful to restore NGLY1 function, primarily in the central nervous system (CNS), but also other tissues including liver and heart, which can alleviate the disease symptoms.

Disclosed herein are isolated nucleic acids, rAAVs, compositions, and methods useful in treating NGLY1 Deficiency. In some aspects, the methods for treating NGLY1 deficiency in a subject can comprise administering an rAAV that contains a transgene encoding NGLY1, for example having a coding sequence of SEQ ID NO: 1, in a gene expression cassette engineered to express the NGLY1 in the CNS (for example under the control of a CAG promoter, for example, the construct having the nucleotide sequence of SEQ ID NO: 8 (including the nucleotide sequence of SEQ ID NO: 1 operably linked to a CAG promoter and a polyA signal sequence) or SEQ ID NO: 9 (the entire construct with the flanking ITR sequences)) and the rAAV is an AAV9 serotype. In certain embodiments, the rAAV is administered ICV or, alternatively, to the cisterna magna. In some aspects, delivery to the cisterna magna can be by direct injection (e.g., intra-cisterna-magna (ICM)) or by lumbar puncture. Certain patients with NGLY1 deficiency may suffer from scoliosis making it difficult to administer the therapeutic to them by lumbar puncture. Accordingly, in patients with scoliosis, the rAAV is administered by ICV or directly to the cisterna magna by ICM. In some aspects, rAAV is administered ICM in subjects with scoliosis. In some aspects, the rAAV is administered ICV and IV, or by ICM and IV.

Also disclosed herein are methods of promoting expression of functional NGLY1 protein in a subject (e.g., in the central nervous system (CNS) and in other tissues of a subject) comprising administering, including ICV administration (or, alternatively, to the cisterna magna), the rAAVs described herein to a subject having or suspected of having a disease of disorder associated with low levels of NGLY1 expression (e.g., NGLY1 deficiency). As used herein, a disease of disorder associated with low levels of NGLY1 expression is a disease or disorder in which a subject has at least 10%, at least 20%, at least 30%, at least 40%, at least 50%, at least 60%, at least 70%, at least 80%, or at least 90% lower levels of NGLY1 expression relative to a control subject (e.g., a healthy subject or an untreated subject).

In some aspects, administering the rAAVs described herein to a subject promotes expression of NGLY1 by between 2-fold and 100-fold (e.g., 2-fold, 5-fold, 10-fold, 20-fold, 50-fold, 75-fold, 100-fold, etc.) compared to a control subject. In some aspects, administering the rAAVs described herein to a subject promotes expression of NGLY1 in the CNS of a subject by between 2-fold and 100-fold (e.g., 2-fold, 5-fold, 10-fold, 20-fold, 50-fold, 75-fold, 100-fold, etc.) compared to a control subject. As used herein a “control” subject may refer to a subject that is not administered the isolated nucleic acids, the rAAVs, or the compositions described herein or a healthy subject. In some aspects, a control subject can be the same subject that is administered the isolated nucleic acids, the rAAVs, or the compositions described herein (e.g., prior to the administration). In some aspects, administering the isolated nucleic acids, the rAAVs, or the compositions described to a subject promotes expression of NGLY1 by 2-fold compared to a control. In some aspects, administering the rAAVs described to a subject promotes expression of NGLY1 by 100-fold compared to a control. In some aspects, administering the rAAVs described to a subject promotes expression of NGLY1 by 5-fold compared to a control. In some aspects, administering the rAAVs described to a subject promotes expression of NGLY1 by 10-fold compared to a control. In some aspects, administering the rAAVs described herein to a subject promotes expression of NGLY1 by 5-fold to 100-fold compared to control (e.g., 5-fold to 10-fold, 10-fold to 15-fold, 10-fold to 20-fold, 15-fold to 25-fold, 20-fold to 30-fold, 25-fold to 35-fold, 30-fold to 40-fold, 35-fold to 45-fold, 40-fold to 60-fold, 50-fold to 75-fold, 60-fold to 80-fold, 75-fold to 100-fold compared to a control).

In some aspects, administering the rAAVs described herein to a subject promotes expression of NGLY1 in a subject (e.g., promotes expression of NGLY1 in the CNS of a subject) by between a 5% and 200% increase (e.g., 5-50%, 25-75%, 50-100%, 75-125%, 100-200%, or 100-150% etc.) compared to a control subject.

Further disclosed herein are methods of treating a subject having a disease of disorder associated with low levels of NGLY1 expression (e.g., NGLY1 deficiency). In some aspects, the methods can comprise administering to the subject an effective amount of an rAAV comprising a capsid containing a nucleic acid engineered to express NGLY1 in the CNS of the subject particularly by ICV administration (or alternatively to the cisterna magna). As used herein, the term "treating" refers to the application or administration of a composition (e.g., an isolated nucleic acid or rAAV as described herein) to a subject who has a disease or disorder associated with low levels of NGLY1 expression (e.g., NGLY1 deficiency), with the purpose to cure, heal, alleviate, relieve, alter, remedy, ameliorate, improve, or affect the disorder, the symptom of the disease, or the predisposition toward a disease.

Alleviating a disease associated with low levels of NGLY1 expression (e.g., NGLY1 deficiency) includes delaying the development or progression of the disease, or reducing disease severity. Alleviating the disease does not necessarily require curative results. As used therein, "delaying" the development of a disease means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

In particular, administration of the rAAV described herein to a human subject suffering from NGLY1 deficiency will within 10 weeks, 15 weeks, 20 weeks, 25 weeks, 30 weeks, 40 weeks, 50 weeks or 1 year after the administration will result in reduction in one or more biomarkers or hallmarks of the disease. In particular, will result in reduction in hypolacrimation, incidence of seizures, developmental delay, reduction or slowing the progression of peripheral neuropathy or reduction in levels of liver transaminases. The inventors have identified levels and accumulation in bodily fluids of GlcNAc-Asn (GNA) as a marker for NGLY1 deficiency and accordingly reduction in GNA levels after administration of the rAAV therapeutic, for example, in fluid samples and as measured by LC-MS/MS is indicative of therapeutic efficacy (see infra).

"Development" or "progression" of a disease means initial manifestations and/or ensuing progression of the disease. Development of the disease can be detectable and assessed using standard clinical techniques as well known in the art. However, development also refers to progression that can be undetectable. As used herein the terms development or progression refer to the biological course of the symptoms. "Development" includes occurrence, recurrence, and onset. As used herein "onset" or "occurrence" of a disease can be associated with low levels of NGLY1 expression (e.g., NGLY1 deficiency).

In some aspects, the subject can be a human, a mouse, a rat, a pig, a dog, a cat, or a non-human primate. In some aspects, a subject has or is suspected of having a disease or disorder associated with low levels of NGLY1 expression (e.g., NGLY1 deficiency). In some aspects, a subject having a disease or disorder associated with low levels of NGLY1 expression (e.g., NGLY1 deficiency) comprises at least one NGLY1 allele having a loss-of-function mutation (e.g., associated with NGLY1 deficiency). In some aspects, a NGLY1 allele having a loss-of-function mutation (e.g., associated with NGLY1 deficiency) comprises a frameshift mutation, a splice site mutation, a missense mutation, a truncation mutation or a nonsense mutation. A subject may have two NGLY1 alleles having the same loss-of-function mutations (homozygous state) or two NGLY1 alleles having different loss-of-function mutations (compound heterozygous state). In certain aspects, the subject is a carrier of an NGLY1 deficiency and, in certain aspects, is heterozygous for a loss of function allele described herein.

In some aspects, a NGLY1 allele having a loss-of-function mutation can comprise a frameshift mutation in exon 12. In some aspects, a NGLY1 allele having a loss-of-function mutation can comprise a nonsense mutation in exon 8 resulting in an Arg401-to-Ter (e.g. a stop codon) (R401X) substitution. In some aspects, a NGLY1 allele having a loss-of-function mutation comprises a frameshift mutation resulted from a 1-bp deletion (c.1891delC). In some aspects, a NGLY1 allele having a loss-of-function mutation comprises a c.1201A-T transversion in exon 8 resulting in an Arg401-to-Ter (e.g., a stop codon) (R401X) substitution. In some aspects, a NGLY1 allele having a loss-of-function mutation can comprise a 1-bp duplication (c.1370dupG) in exon 9, resulting in a frameshift and premature termination (Arg458-to-Ter). In some aspects, a NGLY1 allele having a loss-of-function mutation comprises a 3-bp deletion (c.1205 1207delTTC), resulting in the deletion of 1 residue (402del). In some aspects, a NGLY1 allele having a loss-of-function mutation can comprise a c.1570C-T transition, resulting in an Arg542-to-Ter (R542X) substitution.

In some aspects, the rAAVs disclosed herein can be administered in sufficient amounts to transfect the cells of a desired tissue and to provide sufficient levels of gene transfer and expression without undue adverse effects. Pharmaceutically acceptable routes of administration include, but are not limited to, direct delivery to the selected organ (e.g., to the central nervous system), by ICV or administration to the cisterna magna, oral, inhalation (including intranasal and intratracheal delivery), intraocular, intracerebroventricular, intravenous, intramuscular, subcutaneous, intradermal, and other parental routes of administration. Routes of administration can be combined, if desired.

In some aspects, the dose of rAAV virions required to achieve a particular "therapeutic effect," e.g., the units of dose in genome copies/per kilogram of body weight (GC/kg) (or alternatively based upon brain size or CSF volume), can vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art. An effective amount of an rAAV is an amount sufficient to target infect a subject or target a desired tissue. In some aspects, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of the rAAV can be in the range of from about 1 ml to about 100 ml of solution containing from about $10^9$ to $10^{16}$ genome copies. In some aspects, the rAAV transduces hepatocytes. In some aspects, the effective amount of rAAV can be $10^{10}$, $10^{11}$, $10^{12}$, $10^{13}$, or $10^{14}$ genome copies per kg. In some aspects, the effective amount of rAAV can be $10^{10}$, $10^{11}$, $10^{12}$, $10^{13}$, $10^{14}$, or $10^{15}$ genome copies per subject. In some cases, a dosage between about $6\times10^{09}$ to $6\times10^{14}$ rAAV genome copies can be appropriate.

In some aspects, rAAV compositions can be formulated to reduce aggregation of AAV particles in the composition, particularly where high rAAV concentrations are present (e.g., $10^{13}$ GC/ml or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Assessment of Therapeutic Efficacy. The efficacy of the rAAV compositions described herein may be assessed by in vitro assays and by in vivo assays, for example in NGLY1 deficiency animal models. Assessment of efficacy of administration is described in Examples 1 and 2 herein.

GNA as biomarker. NGLY1 deficiency is a slowly progressive, ultra-low-prevalence rare disease resulting from a single enzyme defect in NGLY1. NGLY1 is required to cleave the bond linking the reducing end GlcNAc (from an N-linked glycan) to an asparagine in misfolded proteins. This disease is associated with significant accumulation of the NGLY1 substrate, GlcNAc-Asparagine (GNA), in plasma, CSF, and tissues. The accumulation of GNA has been observed in all preclinical models and patient samples examined to date. These observations combined with the biochemical understanding that the bond linking GlcNAc to asparagine (ASN) in GNA is the same bond that is normally cleaved by NGLY1 indicates that GNA accumulation is the primary biochemical event in this disease. The restoration of NGLY1 function will prevent the accumulation of GNA.

The accumulation of GNA in critical CNS regions is a direct consequence of the absence of NGLY enzymatic activity and has been shown to correlate with disease severity in NGLY1 deficient rats. Introduction of the wild-type NGLY1 gene into tissues of these animals results in a significant reduction of GNA levels that correlates with improved pathology and animal behavior. Data from the NGLY1 natural history study suggests that NGLY1 deficiency shows high phenotypic variability and slow progression of most aspects of the disease, which may require extended clinical observation to measure progression. Based on the biochemical understanding of NGLY1 function, the therapeutic approached aimed at replacing wild type NGLY1, and the nonclinical data, GNA levels are reasonably likely to reflect NGLY1 correction and to predict clinical benefit.

In NGLY1 deficient cells, N-linked glycoprotein degradation is disrupted and results in the generation of GNA. NGLY1 normally works with the cytosolic mannosidase (Man2c1), ENGase, the proteosome, and the lysosomal system to break the N-linked glycoprotein down to monosaccharides and amino acids. In NGLY1 deficient cells, the cytosolic mannosidase (Man2c1), ENGase, proteases, and the lysosomal system still function normally; however, in the absence of NGLY1 cells are not able to metabolize the bond linking the terminal GlcNAc to asparagine. This metabolic block leads to the accumulation of GNA in tissues and fluids throughout the body.

In the absence of NGLY1, GNA cannot be cytosolically catabolized so is the "limit digestion product" of all accumulating cytosolic N-linked glycoproteins. Since GNA is the substrate "sum" of all NGLY1 target glycoproteins it is considered an optimal substrate measure of NGLY1 enzymatic activity.

Mouse model for NGLY1 deficiency. The Ngly1 deficient mouse is embryonic lethal in the C57BL/6 background (Fujihira 2017). Although the absence of Ngly1 is lethal in mice, other mouse studies suggest that 4- to 5-fold overexpression of hNGLY1 is not toxic, and that a relatively small amount of active NGLY1 protein is required to rescue embryonic lethality in mice.

Rat model for NGLY1 deficiency. A rat model of NGLY1 deficiency has been created using CRISPR-Cas9 in the Sprague Dawley rat (Asahina 2020). This model is homozygous for a deletion of exons 11 and 12 of as well as the 3' poly A region of the Ngly1 gene. Exons 11 and 12 encode the PAW (mannose-binding) domain of NGLY1. Ngly1−/− rats exhibit potential disease relevant phenotypes as measured using rotarod, locomotor/rearing, and passive avoidance behavior assessments. Therapeutic efficacy for NGLY1 therapeutics may be assessed in this model. NGLY1-deficient human HEK293, HepG2 and ReNcell VM cell lines that represent both the systemic (kidney cells, liver cells) and the CNS/PNS (neuronal progenitor cells) components of NGLY1 deficiency are also useful for assessment of the therapeutic efficacy.

In addition to the characterization of behavioral phenotypes in the rat model, the substrate biomarker GNA was also assessed in the Ngly1 deficient rat and in the NGLY1 deficient HEK293, HepG2, and ReNcell VM cell lines. All three NGLY1 deficient cell lines exhibited increased levels of GNA compared with their wild-type controls. In particular, the Ngly1−/− animals showed significant elevation of the substrate biomarker in urine, blood, CSF and all tissues examined compared with wild-type animals. GNA substrate biomarker accumulation was the highest in the brain compared with PNS and systemic tissues, highlighting the necessity of efficient delivery to CNS tissues. A reduction in the GNA substrate levels in Ngly1−/− animals would be an indicator of therapeutic efficacy, for example within days or weeks of administration.

With respect to pathology, Ngly1−/− rats showed progressive CNS and PNS pathology. Early-onset axon/myelin degeneration of both DRGs and the spinal cord increased in severity while infiltrating immune cells appeared later in life. The same was true with respect to neuronal loss, mineralization and gliosis in the thalamus, which were not detectable at 33 days after birth.

Kits

Disclosed herein are kits comprising any of the agents described herein. In some aspects, any of the agents disclosed herein can be assembled into pharmaceutical or diagnostic or research kits to facilitate their use in therapeutic, diagnostic or research applications. A kit can include one or more containers housing the components of the disclosure and instructions for use. Specifically, such kits may include one or more agents described herein, along with instructions describing the intended application and the proper use of these agents. In some aspects, the agents in a kit can be in a pharmaceutical formulation and dosage suitable for a particular application and for a method of administration of the agents. Kits for research purposes can contain the components in appropriate concentrations or quantities for running various experiments.

Also disclosed herein are kits for producing a rAAV. In some aspects, the kit can comprise a container housing an isolated nucleic acid encoding a NGLY1 protein or a portion thereof. In some aspects, the kits can further comprise instructions for producing the rAAV. In some aspects, the kit further comprises at least one container housing a recombinant AAV vector, wherein the recombinant AAV vector comprises a transgene.

In some aspects, the kits can comprise a container housing a recombinant AAV as described supra. In some aspects, the kits can further comprises a container housing a pharmaceutically acceptable carrier. For example, a kit can comprise one container housing a rAAV and a second container housing a buffer suitable for injection of the rAAV into a subject. In some aspects, the container can be a syringe.

In some aspects, the kits can be designed to facilitate use of the methods described herein by researchers and can take many forms. Each of the compositions of the kit, where applicable, may be provided in liquid form (e.g., in solution), or in solid form, (e.g., a dry powder). In some aspects, some of the compositions can be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions can be associated with the kit, for example, audiovisual (e.g., videotape, DVD, etc.), Internet, and/or web-based communications, etc. The written instructions can be in a form prescribed by a governmental agency regulating the manufacture, use or sale of pharmaceuticals or biological products, which instructions can also reflect approval by the agency of manufacture, use or sale for animal administration.

The kits disclosed herein can also contain any one or more of the components described herein in one or more containers. In some aspects, the kits can include instructions for mixing one or more components of the kit and/or isolating and mixing a sample and applying to a subject. The kits can include a container housing agents described herein. The agents can be in the form of a liquid, gel or solid (powder). The agents can be prepared sterilely, packaged in syringe and shipped refrigerated. Alternatively, it can be housed in a vial or other container for storage. A second container can have other agents prepared sterilely. Alternatively the kits can include the active agents premixed and shipped in a syringe, vial, tube, or other container. The kits can have one or more or all of the components required to administer the agents to an animal, such as a syringe, topical application devices, or iv needle tubing and bag, particularly in the case of the kits for producing specific somatic animal models.

In some aspects, the method disclosed herein can involve transfecting cells with total cellular DNAs isolated from the tissues that potentially harbor proviral AAV genomes at very low abundance and supplementing with helper virus function (e.g., adenovirus) to trigger and/or boost AAV rep and cap gene transcription in the transfected cell. In some aspects, RNA from the transfected cells can provide a template for RT-PCR amplification of cDNA and the detection of novel AAVs. In cases where cells are transfected with total cellular DNAs isolated from the tissues that potentially harbor proviral AAV genomes, it is often desirable to supplement the cells with factors that promote AAV gene transcription. For example, the cells can also be infected with a helper virus, such as an Adenovirus or a Herpes Virus. In some aspects, the helper functions can be provided by an adenovirus. The adenovirus can be a wild-type adenovirus, and can be of human or non-human origin, for example, non-human primate (NHP) origin. Similarly, adenoviruses known to infect non-human animals (e.g., chimpanzees, mouse) can also be employed in the methods of the disclosure (See, e.g., U.S. Pat. No. 6,083,716). In addition to wild-type adenoviruses, recombinant viruses or non-viral vectors (e.g., plasmids, episomes, etc.) carrying the necessary helper functions can be utilized. Such recombinant viruses are known in the art and may be prepared according to published techniques. See, e.g., U.S. Pat. Nos. 5,871,982 and 6,251,677, which describe a hybrid Ad/AAV virus. A variety of adenovirus strains are available from the American Type Culture Collection, Manassas, Va., or available by request from a variety of commercial and institutional sources. Further, the sequences of many such strains are available from a variety of databases including, e.g., PubMed and GenBank.

Cells can also be transfected with a vector (e.g., helper vector) which provides helper functions to the AAV. The vector providing helper functions can provide adenovirus functions, including, e.g., E1a, E 1b, E2a, E40RF6. The sequences of adenovirus gene providing these functions can be obtained from any known adenovirus serotype, such as serotypes 2, 3, 4, 7, 12 and 40, and further including any of the presently identified human types known in the art. Thus, in some aspects, the methods involve transfecting the cell with a vector expressing one or more genes necessary for AAV replication, AAV gene transcription, and/or AAV packaging.

In some aspects, an isolated capsid gene can be used to construct and package recombinant AAV vectors, using methods well known in the art, to determine functional characteristics associated with the novel capsid protein encoded by the gene. For example, isolated capsid genes can be used to construct and package recombinant AAV (rAAV) vectors comprising a reporter gene (e.g., B-Galactosidase, GFP, Luciferase, etc.). The rAAV vector can then be delivered to an animal (e.g., mouse) and the tissue targeting properties of the isolated capsid gene can be determined by examining the expression of the reporter gene in various tissues (e.g., heart, liver, kidneys) of the animal. Other methods for characterizing isolated capsid genes are disclosed herein and still others are well known in the art.

The kits disclosed can have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kits can be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kits can also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The instructions included within the kit can involve methods for detecting a latent AAV in a cell. In addition, kits of the disclosure can include, instructions, a negative and/or positive control, containers, diluents and buffers for the sample, sample preparation tubes and a printed or electronic table of reference AAV sequence for sequence comparisons.

EXAMPLES

Example 1: ICV Delivery of AAV9-NGLY1 Gene Replacement Therapy Improves Phenotypic and Biomarker Endpoints in Ngly1 Deficient Rats NGLY1 deficiency is a devastating, ultra-rare, autosomal recessive disease caused by loss of function mutations in NGLY1. Approximately 90 patients have been confirmed worldwide by the Grace Science Foundation and as reported in publications. The NGLY1 gene encodes N-glycanase 1, a conserved enzyme that cleaves N-glycans from misfolded glycoproteins destined for proteasomal degradation as part of the endoplasmic reticulum-associated degradation (ERAD) pathway. Symptoms of NGLY1 deficiency include hyperkinetic movements, neuropathy, low muscle tone, scoliosis, constipation, gait abnormalities, small hands and/or feet, abnormal liver function, developmental delay, hypo/alacrima, seizures, lack of language development and swallowing difficulties.

Disclosed herein is an AAV9 gene therapy (e.g., GS-100) that delivers a functional copy of the full-length human NGLY1 gene (hNGLY1) for the treatment of NGLY1 deficiency.

Vector design. Described herein is an rAAV9 vector that contains a codon-optimized full-length version of hNGLY1 (SEQ ID NO: 1) under the control of the CAG promoter (see FIG. 8; also SEQ ID NO: 8 (including the nucleotide sequence of SEQ ID NO: 1 operably linked to a CAG promoter and a polyA signal sequence) or SEQ ID NO: 9 (the entire construct with the flanking ITR sequences).

The vector elements are: AAV2 ITRs, CAG promoter, chimeric CB-BG intron, codon-optimized human NGLY1 cDNA, WPRE-mut6 enhancer element, and Rb-BG poly A signal. The vector can be packaged in the AAV9 capsid in a human embryonic kidney (HEK) 293 cell culture production system. The elements within the GS-100 vector genome were chosen to provide sustained broad expression across tissues.

Promoter. The CAG promoter (0.97 kb) combines the CMV early enhancer with the chicken B-actin promoter for broad expression across tissues.

Enhancer. The WPRE-mut6 sequence was included in the vector to increase protein expression Intron. Sequences from both the chicken beta-actin promoter (including the first exon and intron) and the rabbit beta-globin intron were included to increase nuclear export and translation.

Transgene. The transgene itself was modified from its known coding sequence (NM_018297.4) to allow for cloning and optimal protein translation. The rabbit B-globin poly-adenylation site is a strong poly-adenylation signal and was included to facilitate mRNA stability and maintain expression levels.

Methods. A rat model of NGLY1 deficiency was used. Rats were injected with GS-100 between day 39 and day 45 postnatal; and sacrificed at 9 weeks. GS-100 was administered intravenous (IV), intracerebroventricular (ICV), or both (dual IV+ICV) in sequence. Rats were assessed using rotarod, location (open field with rearing), and biomarker determination.

Results. FIG. 1 shows that ICV GS-100 administration results in broad vector genome biodistribution. GS-100 vector genome (VG) DNA was quantified by qPCR to calculate VG copies per diploid genome. The results demonstrate that ICV and ICV+IV administration results in higher biodistribution in CNS tissues than IV alone; and broad distribution in the peripheral tissues (heart and liver). Dual administration (ICV+IV) did not result in a consistent significant increase in biodistribution relative to ICV alone. IV administration had substantially lower distribution in the CNS than either ICV or ICV+IV administration.

Figure 2:
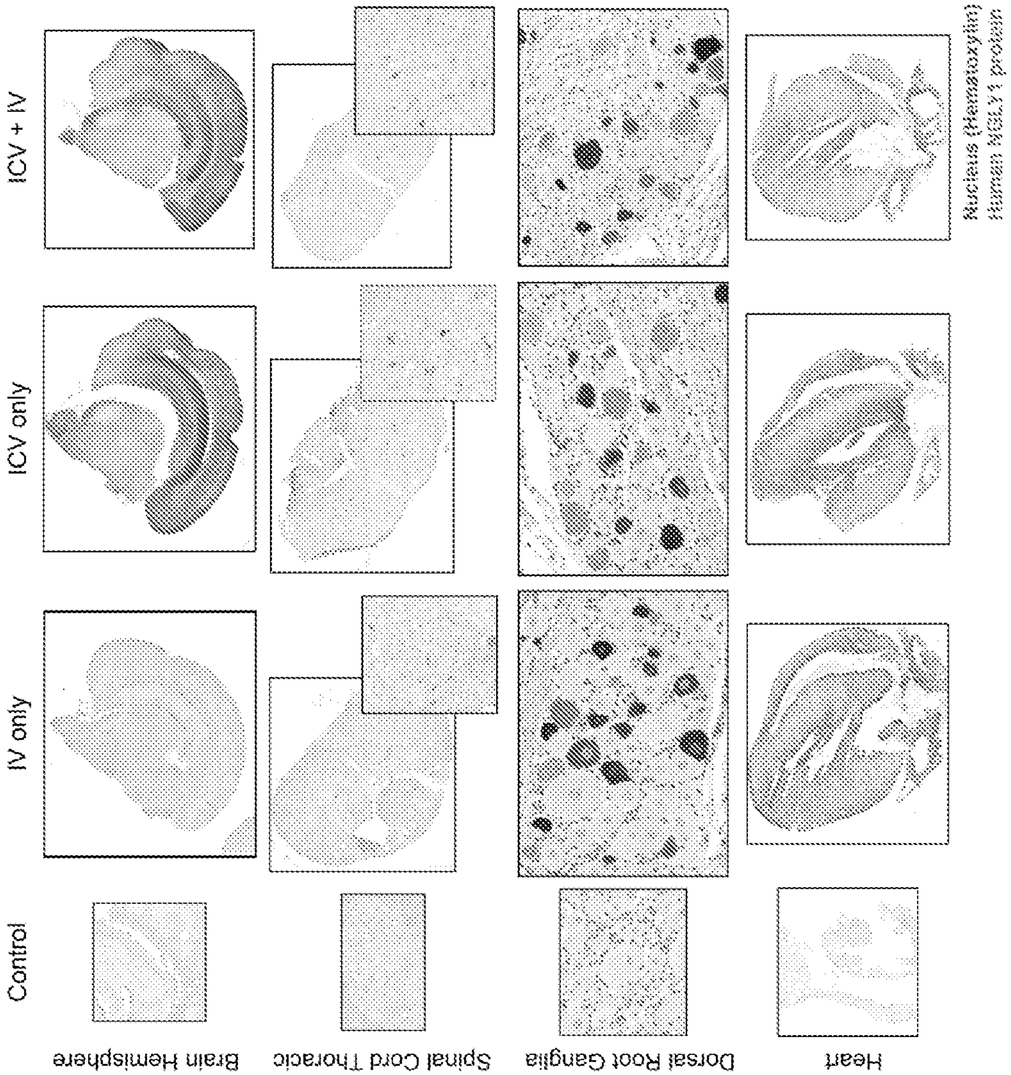
FIG. 2 shows that ICV GS-100 administration results in CNS hNGLY1 (human NGLY1) protein expression in an animal model of NGLY1 deficiency.

Immunohistochemistry (IHC) analysis was carried out on heart, dorsal root ganglia, spinal cord, and brain tissues after GS-100 administration and compared to a control. IHC analysis of rat tissues detected hNGLY1 protein expression in GS-100 treated rats. FIG. 2 shows that ICV GS-100 administration results in CNS hNGLY1 protein expression. ICV and ICV+IV administration results in substantial hNGLY1 protein expression in the CNS. ICH analysis of IV administration of GS-100 did not detect substantial CNS expression of hNGLY1 protein.

Figure 3:
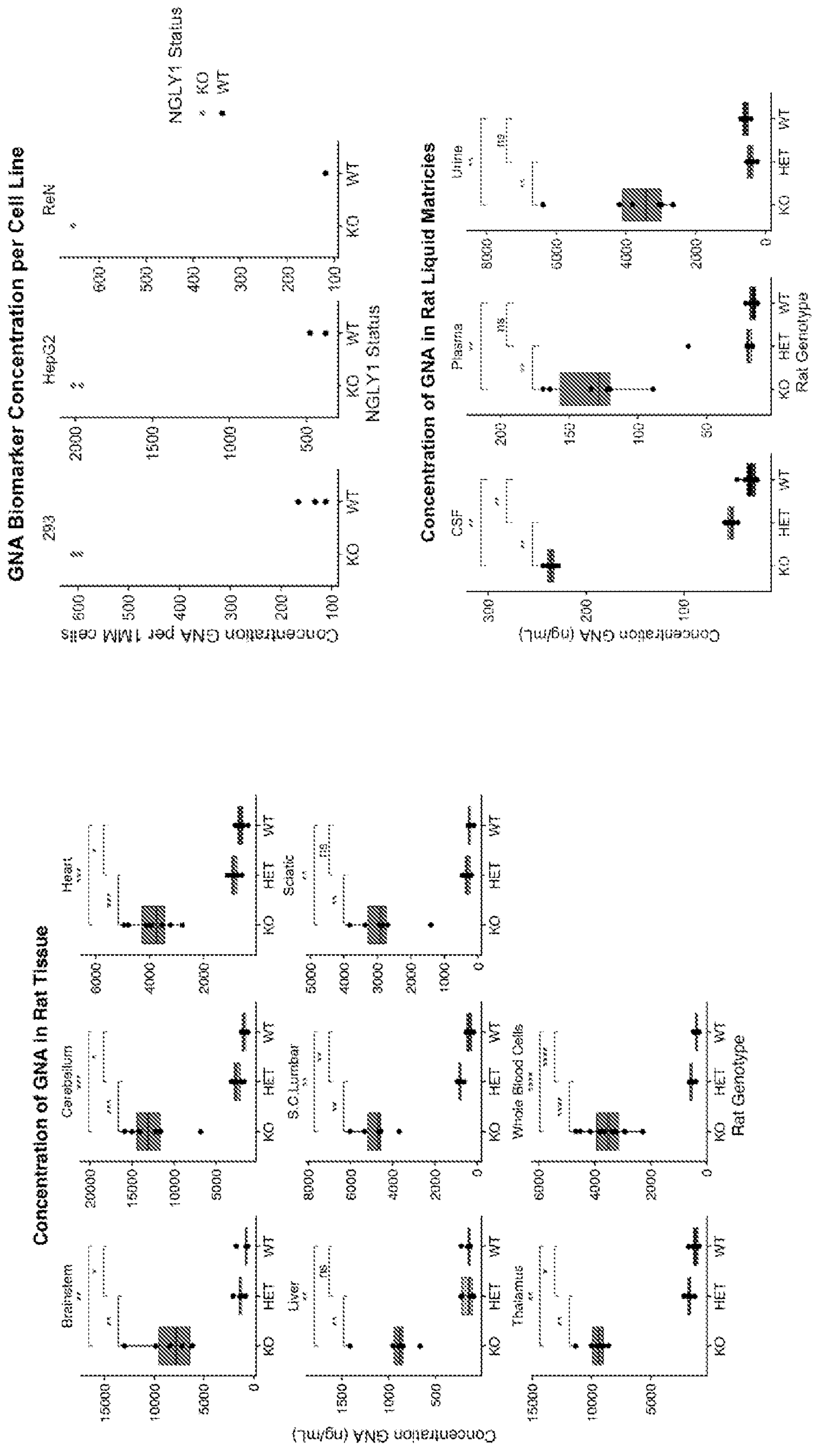
FIG. 3 shows that GNA can be detected in NGLY1 deficient organisms.
Figure 4:
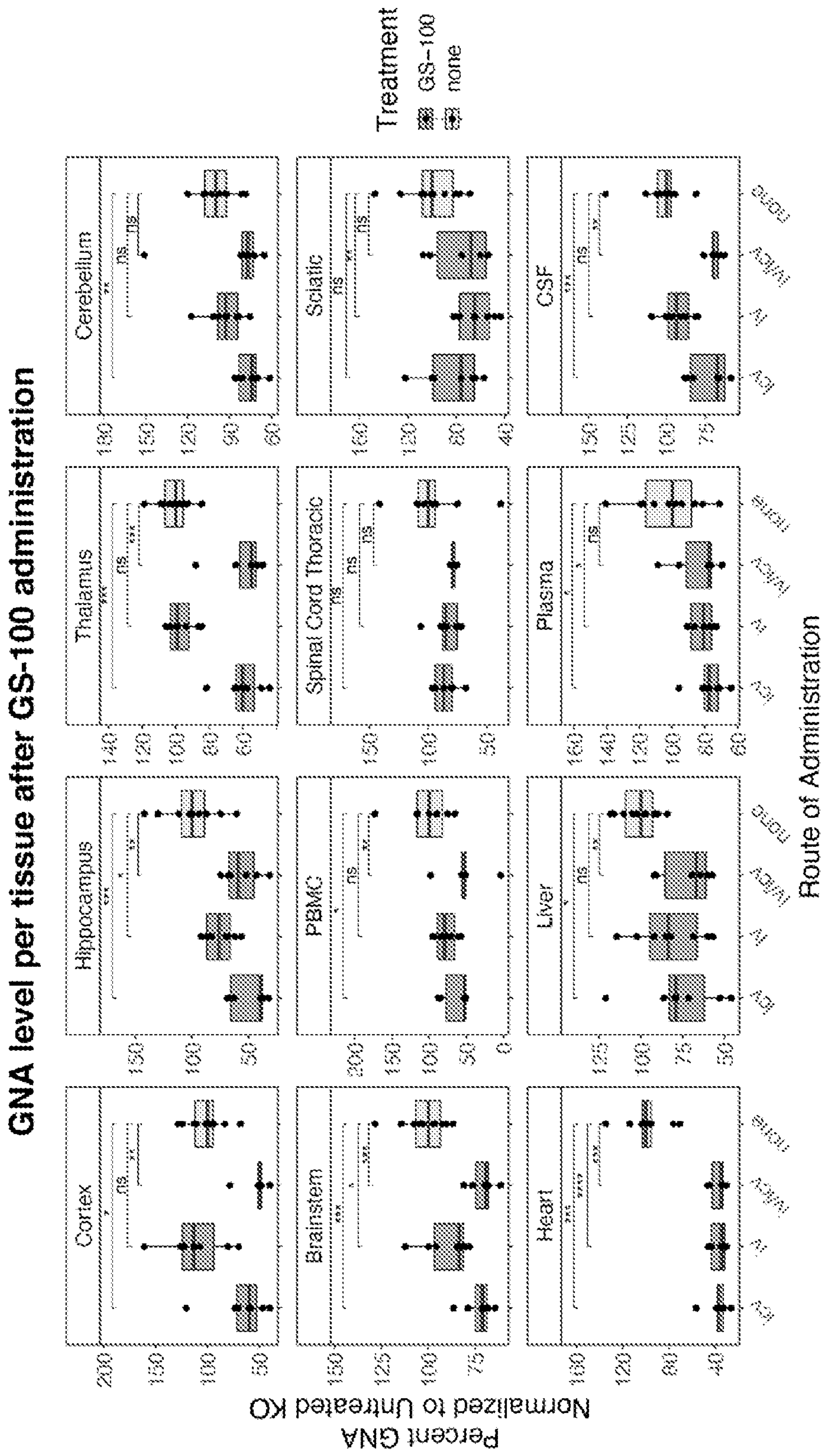
FIG. 4 shows that GS-100 administration reduced GNA biomarker levels.

Next, in the absence of NGLY1, the inability to completely cleave N-glycans from glycoproteins results in the accumulation of GlcNAc-Asn (GNA). For example, GNA can be detected in NGLY1 deficient organisms (human cell line and rat data shown, Wilcoxon $p<0.01$; FIG. 3). GNA biomarker levels were quantitatively measured following GS-100 administration using LC-MS/MS. FIG. 4 demonstrates that GS-100 administration reduced GNA biomarker levels. ICV or ICV+IV administration significantly reduces GNA accumulation in most tissues (Dunn's $p<0.01$), with no additional significant benefit provided by dual administration. IV administration of GS-100 reduces GNA accumulation in two brain regions and some peripheral tissues.

Figure 5:
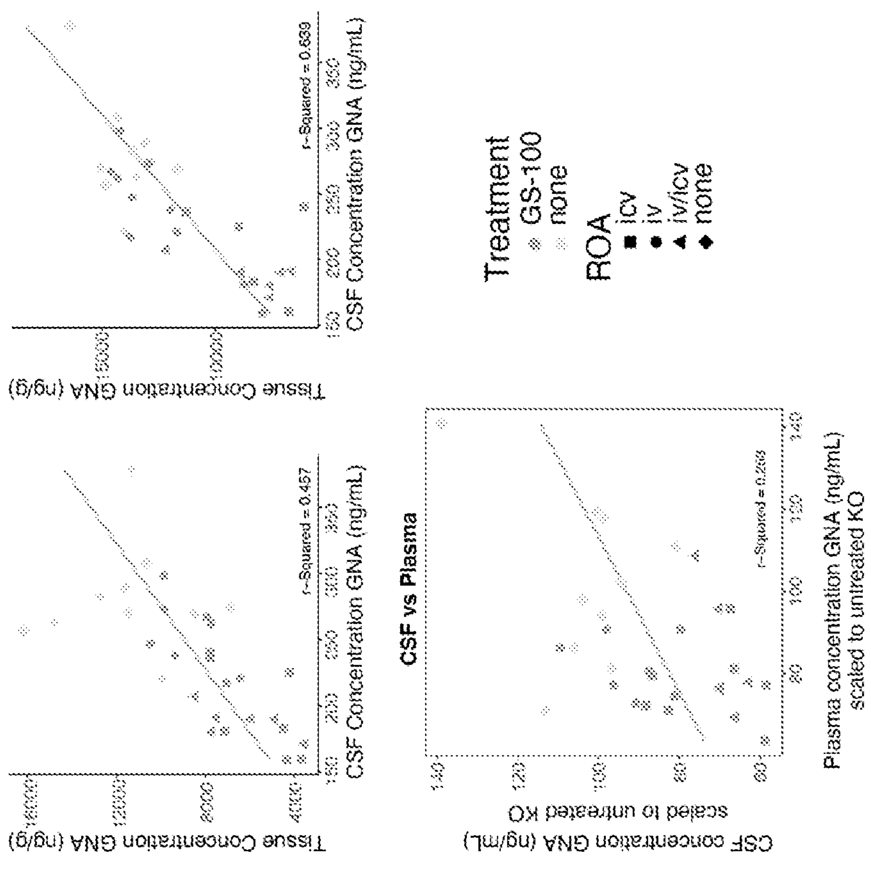
FIG. 5 shows that GNA biomarker reduction correlates in tissues and fluids.

The reduction in GNA biomarker levels correlates in tissues and fluids. GNA concentrations, measured by LC-MS/MS, were compared between tissue and liquid matrices following administration with GS-100. FIG. 5 shows that GNA concentrations in brain tissues correlate with GNA concentrations in CSF (linear model, $p<0.001$), and GNA concentrations correlate with GNA concentrations in plasma (linear model, $p<0.05$). These data provide evidence that GNA accumulation in liquid matrices can be used as a marker for the presence of functional NGLY1 in the tissue.

Figure 6A:
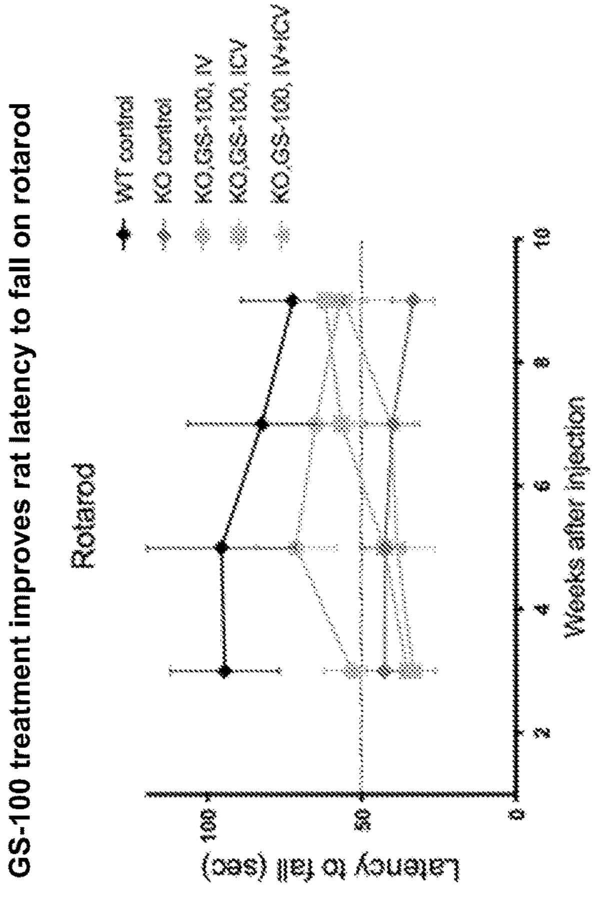
FIGS. 6A-B shows that GS-100 improves Ngly1 deficient rat behavioral deficits.
Figure 6B:
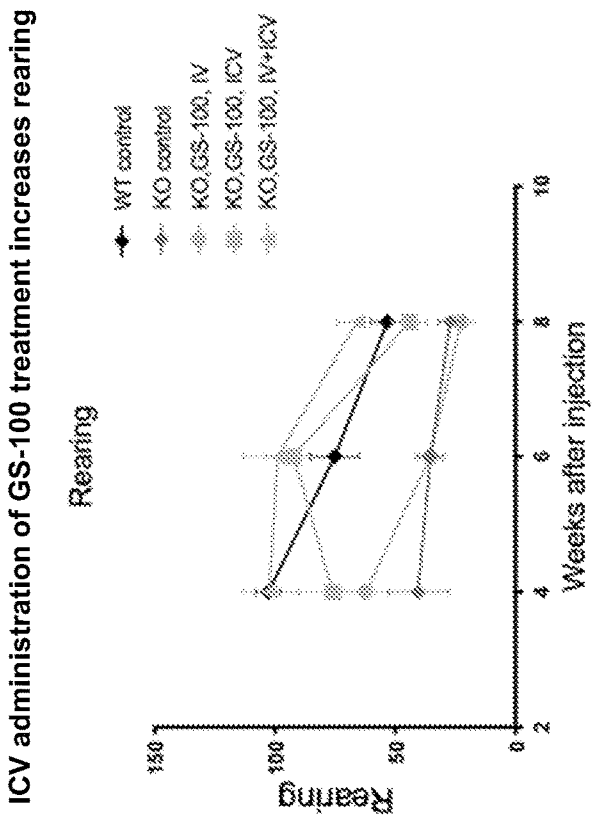

GS-100 improves Ngly1 deficient rat behavioral deficits. Behavioral analysis of Ngly1 deficient rats indicates deficits as assessed by decreased latency to fall off the rotarod and their ability to rear in open field locomotor testing compared with wild-type littermates. Following ICV administration of GS-100, the deficits in these behaviors improved significantly ($p<0.01$) compared to untreated controls (see, FIG. 6). There was not a significant difference in behavioral improvement for ICV+IV administration compared with ICV administration.

Figure 7:
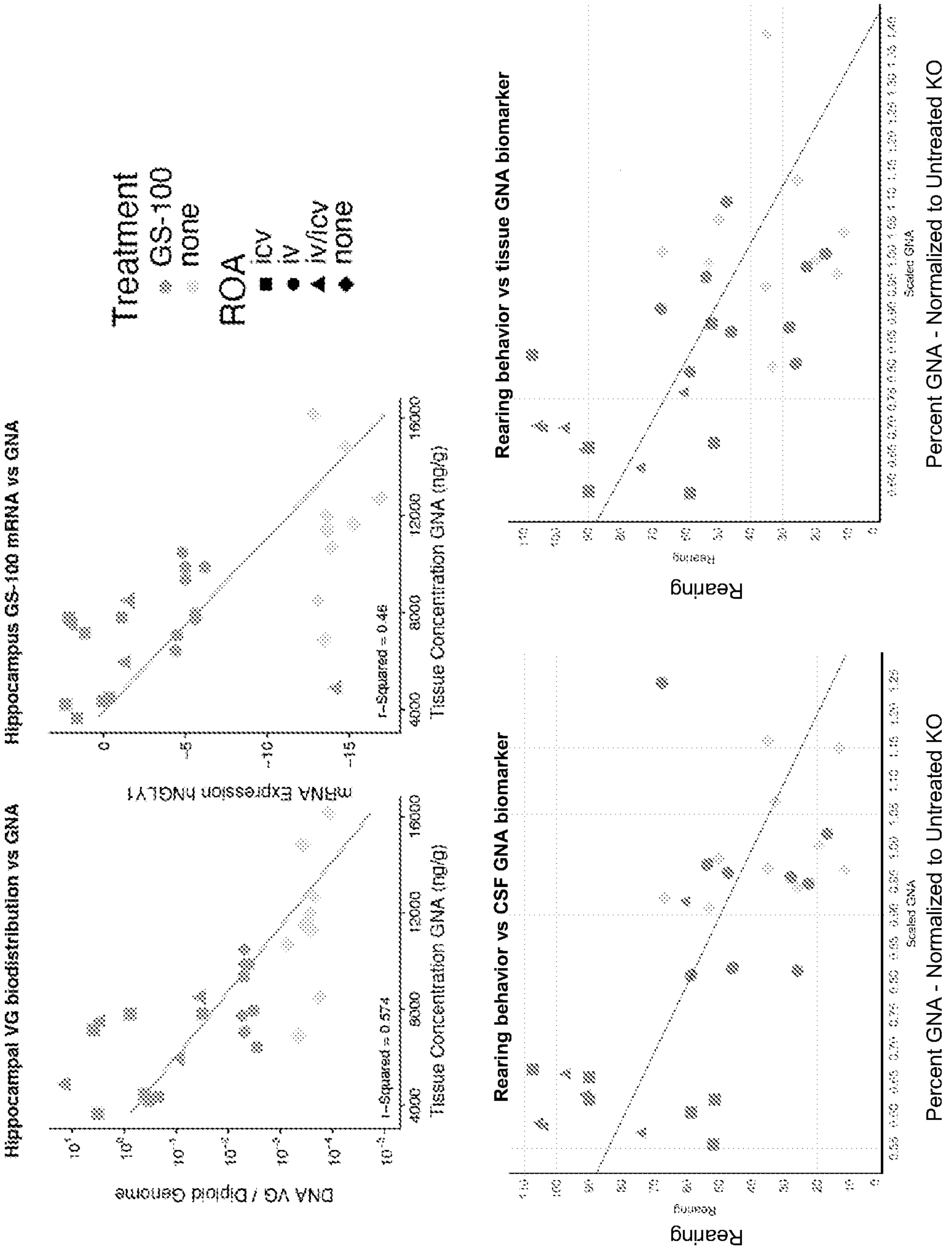
FIG. 7 shows that GS-100 vector genome and hNGLY1 mRNA expression correlates with GNA tissue concentration in the hippocampus.

GNA biomarker reduction also correlates with GS-100. GS-100 vector genome (VG) DNA and mRNA expression were determined by qPCR (hNGLY1 mRNA compared to Hprt mRNA expression). FIG. 7 shows that GNA accumulation level was quantified using LC-MS/MS. GS-100 delivery (VG DNA) or expression (mRNA) inversely correlated with GNA concentration (linear model, $p<0.001$). Improved behavioral outcomes following GS-100 administration correlate with reduced GNA concentrations. These data demonstrate that the GNA biomarker acts as a pharmacodynamic marker of GS-100 mediated delivery of functional hNGLY1.

Discussion GS-100 is an AAV9 gene therapy that delivers a functional copy of the full-length human NGLY1 gene for the treatment of NGLY1 deficiency. GS-100 administration via ICV and ICV+IV in Ngly1 deficient rats results in widespread biodistribution of AAV9 encoding human NGLY1 DNA and corresponding human NGLY1 protein expression. IV administration did not provide substantial delivery to CNS tissues, but GS-100 administration delivered by ICV or by the dual route ICV+IV significantly reduced levels of the biomarker GNA in the CNS. ICV and ICV+IV GS-100 treated Ngly1 deficient rats display improvement in functional behavioral testing. ICV+IV administration compared with ICV alone did not provide additional GS-100 transduction or expression levels in the CNS or additional improvements in behavioral phenotypes. Biomarker reduction following ICV administration of GS-100 correlated with vector DNA biodistribution, hNGLY1 mRNA expression, and behavioral improvement. The correlation between tissue GNA and fluid GNA, combined with the correlation between GNA level and GS-100, demonstrate that GNA could serve as a pharmacodynamic marker for delivery of functional human NGLY1.

In sum, these data provide evidence that ICV delivery of GS-100 can be useful as a therapy for NGLY1 deficiency.

Figure 9:
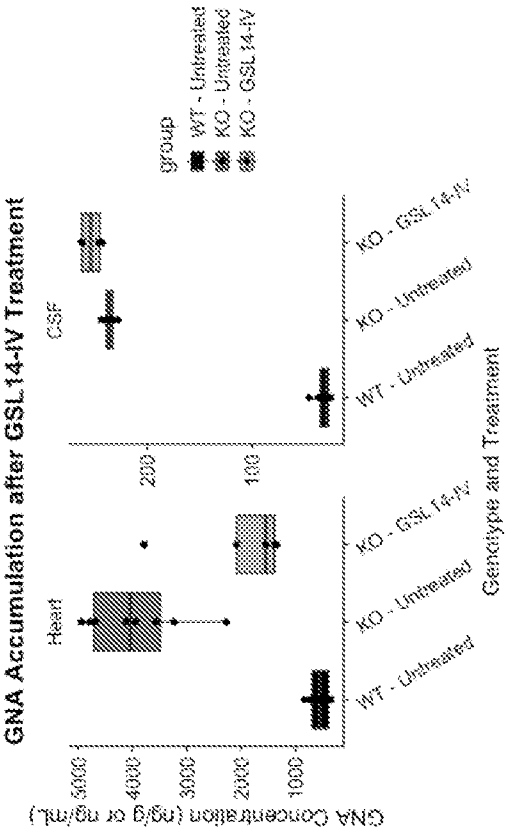
FIG. 9 shows a trend toward reduction in GNA accumulation after GSL-14 (e.g., AAV-NGLY1; hNGLY1 cDNA codon optimized for reduced CpG content and a V5 tag included using a CAG promoter) intravenous administration.

Example 2: AAV9-Mediated Gene Therapy for NGLY1 Deficiency and Assessment of GNA Biomarker Changes in a Rat Disease Model Elevated GNA and NHGNA were recently reported in dried blood spots and urine samples, respectively, from NGLY1 patients. Based on this data, it was tested whether cytosolic GNA (and NHGNA) accumulation is a characteristic of NGLY1 deficiency, correlating directly with a lack of NGLY1 activity. Although Ngly1 knockout mice are perinatal lethal, a Ngly1 knockout ($Ngly1^{-/-}$) rat model was used. Approximately 25% of these homozygous animals survive beyond weaning. Characterization of these surviving knockouts reveals decreased initial body weight and abnormalities in rotarod and grip strength tests. Longitudinal assessments of these phenotypes, as well as GNA biomarker changes in blood, urine and CSF were carried out after treatment with AAV-NGLY1 (GSL-14; hNGLY1 cDNA was codon optimized for reduced CpG content and a V5 tag was included using a CAG promoter; SEQ ID NO: 11). Cohorts of study animals (wildtype and $Ngly1^{-/-}$ rats) were treated with a single intravenous dose ($3\times10^{13}$ of an AAV9 vector expressing human NGLY1) at age 5-7 weeks. GNA levels in serum/urine were monitored weekly and CSF was collected at 5 weeks post-administration, the study's end, for comparison with untreated wildtype and Ngly1-/- controls. The results showed decreased biomarker in the heart but not in the brain or CSF (see, FIG. 9). The GNA biomarker, linked tightly to NGLY1's enzymatic activity, combined with an NGLY1 disease rat model that exhibits early onset of motor neuron defects consistent with patient phenotypes are both important to determining the in vivo efficacy of GS-100 gene therapy.

(CMV enhancer-CB promoter-chimeric intron-midGC transgene codon optimized-WPREmut6-rGB poly A):

SEQ ID NO: 11

```
ctagtcgacattgattattgactagttattaatagtaatcaattacggggtcattagttcatagcccatatatggagttccgcgttacat

aacttacggtaaatggcccgcctggctgaccgcccaacgacccccgcccattgacgtcaataatgacgtatgttcccatagtaacgccaata

gggactttccattgacgtcaatgggtggagtatttacggtaaactgcccacttggcagtacatcaagtgtatcatatgccaagtacgccccta

ttgacgtcaatgacggtaaatggcccgcctggcattatgcccagtacatgaccttatgggactttcctacttggcagtacatctacgtattagtc

atcgctattaccatgtcgaggacgcgtccacgttctgcttcactctccccatctcccccccctccccacccccaattttgtatttatttatttt

taattattttgtgcagcgatgggggcgggggggggggggcgcgcgccaggcggggcggggggggcgaggggggggggggcgaggcg

gagaggtgcggcggcagccaatcagagcggcgcgctccgaaagtttccttttatggcgaggcggcggcggcggcggccctataaaaag

cgaagcgcgcggcgggcgggagcaagctttattgcggtagtttatcacagttaaattgctaacgcagtcagtgcttctgacacaacagtctc

gaacttaagctgcagaagttggtcgtgaggcactgggCAGgtaagtatcaaggttacaagacaggtttaaggagaccaatagaaactgg

gcttgtcgagacagagaagactcttgcgtttctgataggcacctattggtcttactgacatccactttgcctttctctccacagGCAgtgtcca

ctcccagttcaattacagctcttaaggctagagtacttaatacgactcactatagGAATTCgccaccATGGCTGCAGCTGC

ACTGGGgTCCTCTTCCGGCTCCGCTTCTCCTGCTGTTGCTGAACTGTGTCAAAATACA

CCAGAAACATTTTTAGAAGCaTCTAAATTACTGTTAACATATGCCGATAATATACTG

AGAAATCCCAATGACGAAAAGTATAGATCTATTAGAATTGGAAATACAGCTTTTTCT

ACTAGACTGTTACCTGTTAGAGGAGCCGTTGAATGTCTGTTTGAAATGGGATTCGAA

GAAGGCGAAACACATCTGATTTTTCCTAAGAAAGCaTCAGTTGAACAACTGCAAAAA

ATTAGgGACCTGATTGCCATAGAGAGAAGTAGCAGATTAGATGGCTCCAATAAGAG

CCACAAAGTAAAGTCATCCCAGCAACCTGCAGCCTCCACACAACTCCCCACAACCC

CATCTTCAAATCCTAGTGGATTAAATCAACATACAAGAAATAGACAAGGACAATCTT

CTGATCCTCCATCTGCTTCAACTGTGGCTGCTGATTCTGCTATTTTAGAAGTTCTCCA

ATCTAATATTCAACATGTTCTCGTTTATGAAAATCCTGCTTTACAAGAAAAAGCATT
```

-continued

AGCTTGTATACCAGTCCAAGAATTAAAAAGAAAATCACAAGAAAAACTCTCCAGAG

CTAGAAAATTAGATAAAGGTATTAATATAAGTGATGAAGATTTTCTGTTGCTGGAAT

TATTGCATTGGTTTAAAGAAGAATTTTTTCATTGGGTGAATAATGTGTTATGTTCCAA

GTGTGGAGGACAAACTAGATCCAGAGATAGATCATTATTACCTAGTGATGATGAAC

TGAAATGGGGTGCCAAAGAGGTGGAGGATCACTATTGTGATGCTTGCCAATTTAGC

AATAGATTTCCAAGATATAACAATCCCGAAAAGTTACTGGAAACAAGATGTGGAAG

ATGTGGAGAATGGGCTAATTGTTTTACACTGTGTTGTAGAGCTGTGGGATTTGAAGC

TAGATATGTTTGGGATTACACAGACCATGTGTGGACAGAGGTCTATAGCCCTTCCCA

ACAGAGATGGCTCCACTGTGATGCCTGTGAGGATGTGTGTGACAAACCCTTATTATA

TGAGATAGGATGGGGAAAGAAACTGTCTTATGTGATTGCATTCTCAAAGGATGAGG

TGGTGGATGTCACCTGGAGATATAGCTGTAAACATGAGGAGGTGATTGCCAGAAGA

ACCAAGGTGAAGGAGGCATTACTTAGAGACACCATTAATGGACTTAATAAACAGAG

ACAACTGTTTCTGTCCGAAAACAGAAGAAAAGAACTTCTCCAGAGAATTATTGTGG

AGTTGGTGGAATTtATCTCTCCCAAGACCCCCAAGCCTGGAGAGCTCGGGGGAAGAA

TCTCTGGATCAGTGGCCTGGAGAGTTGCCAGAGGAGAGATGGGACTGCAGAGAAAG

GAGACtCTGTTCATCCCCTGTGAGAATGAGAAGATCTCTAAACAGCTCCACCTGTGTT

ACAATATTGTGAAAGATAGATATGTTAGAGTGTCAAACAACAATCAGACCATTTCTG

GATGGGAGAATGGAGTGTGGAAAATGGAATCTATCTTCAGAAAAGTGGAAACAGAT

TGGCATATGGTGTATCTGGCAAGAAAGGAAGGtTCCTCTTTTGCTTACATCTCCTGGA

AGTTCGAGTGCGGGTCTGTTGGACTGAAAGTGGATTCTATCTCCATTAGAACAAGCA

GTCAAACCTTTCAGACAGGAACAGTGGAATGGAAACTGAGGAGCGATACAGCCCAA

GTGGAACTGACAGGAGATAACTCCCTCCACTCCTATGCTGATTTTTCTGGTGCCACA

GAAGTGATTCTGGAAGCAGAACTGTCCAGAGGAGATGGTGATGTGGCTTGGCAACA

CACCCAGTTATTCAGACAATCTCTGAATGACCATGAGGAAAACTGTCTGGAGATCAT

TATCAAATTCAGTGACCTGggtaagcctatccctaaccctctcctcggtctcgattctacgTGActcgagAATCAA

CCTCTGGATTACAAAATTTGTGAAAGATTGACTGGTATTCTTAACTATGTTGCTCCTT

TTACGCTATGTGGATACGCTGCTTTAATGCCTTTGTATCATGCTATTGCTTCCCGTAT

GGCTTTCATTTTCTCCTCCTTGTATAAATCCTGGTTGCTGTCTCTTTATGAGGAGTTGT

GGCCCGTTGTCAGGCAACGTGGCGTGGTGTGCACTGTGTTTGCTGACGCAACCCCCA

CTGGTTGGGGCATTGCCACCACCTGTCAGCTCCTTTCCGGGACTTTCGCTTTCCCCCT

CCCTATTGCCACGGCGGAACTCATCGCCGCCTGCCTTGCCCGCTGCTGGACAGGGGC

TCGGCTGTTGGGCACTGACAATTCCGTGGTGTTGTCGGGGAAATCATCGTCCTTTCCT

TGGCTGCTCGCCTGTGTTGCCACCTGGATTCTGCGCGGGACGTCCTTCTGCTACGTCC

CTTCGGCCCTCAATCCAGCGGACCTTCCTTCCCGCGGCCTGCTGCCGGCTCTGCGGC

CTCTTCCGCGTCTTCGCCTTCGCCCTCAGACGAGTCGGATCTCCCTTTGGGCCGCCTC

CCCGCATCGATgatctttttccctctgccaaaaattatggggacatcatgaagccccttgagcatctgacttctggctaataaaggaa atttattttcattgcaatagtgtgttggaatttttgtgtctctcactcg.

Although the foregoing invention has been described in some detail by way of illustration and example for purposes of clarity of understanding, certain changes and modifications may be practiced within the scope of the appended claims.

REFERENCES

1. Greene, J. A. and S. H. Podolsky, *Reform, regulation, and pharmaceuticals—the Kefauver-Harris Amendments at 50*. N Engl J Med, 2012. 367(16): p. 1481-3.
2. Wraith, J. E., et al., *Enzyme replacement therapy for mucopolysaccharidosis I: a randomized, double-blinded, placebo-controlled, multinational study of recombinant human alpha-L-iduronidase (laronidase)*. J Pediatr, 2004. 144(5): p. 581-8.
3. Kakkis, E. D., et al., *Long-term and high-dose trials of enzyme replacement therapy in the canine model of mucopolysaccharidosis I*. Biochem Mol Med, 1996. 58(2): p. 156-67.
4. Clarke, L. A., et al., *Long-term efficacy and safety of laronidase in the treatment of mucopolysaccharidosis I*. Pediatrics, 2009. 123(1): p. 229-40.
5. Harmatz, P., et al., *Enzyme replacement therapy for mucopolysaccharidosis VI: a phase 3, randomized, double-blind, placebo-controlled, multinational study of recombinant human N-acetylgalactosamine 4-sulfatase (recombinant human arylsulfatase B or rhASB) and follow-on, open-label extension study*. J Pediatr, 2006. 148 (4): p. 533-539.
6. Muenzer, J., et al., *A phase II/III clinical study of enzyme replacement therapy with idursulfase in mucopolysaccharidosis II (Hunter syndrome)*. Genet Med, 2006. 8(8): p. 465-73.
7. Chi, G. Y., *Some issues with composite endpoints in clinical trials*. Fundam Clin Pharmacol, 2005. 19(6): p. 609-19.
8. Sankoh, A. J., H. Li, and R. B. D'Agostino, Sr., *Use of composite endpoints in clinical trials*. Stat Med, 2014. 33(27): p. 4709-14.
9. Garcia-Garcia, H. M., et al., *Standardized End Point Definitions for Coronary Intervention Trials: The Academic Research Consortium-2 Consensus Document*. Circulation, 2018. 137(24): p. 26352650.
10. Mazzone, E. S., et al., *Reliability of the North Star Ambulatory Assessment in a multicentric setting*. Neuromuscul Disord, 2009. 19(7): p. 458-61.
11. Mayhew, J., et al., *Development and preliminary evidence of the psychometric properties of the GNE myopathy functional activity scale*. J Comp Eff Res, 2018. 7(4): p. 381-395.
12. Vockley, J., et al., *Results from a 78-week, single-arm, open-label phase 2 study to evaluate UX007 in pediatric and adult patients with severe long-chain fatty acid oxidation disorders (LC-FAOD)*. J Inherit Metab Dis, 2019. 42(1): p. 169-177.
13. Balwani, M., et al., *Phase 3 Trial of RNAi Therapeutic Givosiran for Acute Intermittent Porphyria*. N Engl J Med, 2020. 382(24): p. 2289-2301.
14. O'Brien, P. C., *Procedures for comparing samples with multiple endpoints*. Biometrics, 1984. 40(4): p. 1079-87.
15. Pocock, S. J., N. L. Geller, and A. A. Tsiatis, *The analysis of multiple endpoints in clinical trials*. Biometrics, 1987. 43(3): p. 487-98.
16. Tandon, P. K., *Applications of global statistics in analysing quality of life data. Stat Med,* 1990. 9(7): p. 819-27.
17. Harmatz, P., et al., *A novel Blind Start study design to investigate vestronidase alfa for mucopolysaccharidosis VII, an ultra-rare genetic disease*. Mol Genet Metab, 2018. 123(4): p. 488494.
18. Redelmeier, D. A., et al., *Interpreting small differences in functional status: the Six Minute Walk test in chronic lung disease patients*. Am J Respir Crit Care Med, 1997. 155(4): p. 1278-82.
19. Puhan, M. A., et al., *Interpretation of treatment changes in 6-minute walk distance inpatients with COPD*. Eur Respir J, 2008. 32(3): p. 637-43.
20. du Bois, R. M., et al., *Six-minute-walk test in idiopathic pulmonary fibrosis: test validation and minimal clinically important difference*. Am J Respir Crit Care Med, 2011. 183(9): p. 1231-7.
21. Abuduxikuer K, Zou L, Wang L, Chen L, Wang J S. Novel NGLY1 gene variants in Chinese children with global developmental delay, microcephaly, hypotonia, hypertransaminasemia, alacrimia, and feeding difficulty. J Hum Genet. 2020; 65(4):387-396.
22. Ahmed S S, Rubin H, Wang M, Faulkner D, Sengooba A, Dollive S N, et al. Sustained correction of a murine model of phenylketonuria following a single intravenous administration of AAVHSC15-PAH. Mol Ther Methods Clin Dev. 2020; 17:568-580.
23. Aiello-Laws L, Rutledge DN. Management of adult patients receiving intraventricular chemotherapy for the treatment of leptomeningeal metastasis. Clin J Oncol Nurs. 2008; 12(3):429-35.
24. Arvin M, Mononen I. Aspartylglycosaminuria: a review. Orphanet J Rare Dis. 2016; 11(1):162.
25. Asahina M, Fujinawa R, Nakamura S, Yokoyama K, Tozawa R, Suzuki T. Ngly1−/− rats develop neurodegenerative phenotypes and pathological abnormalities in their peripheral and central nervous systems. Hum Mol Genet. 2020; 29(10):1635-1647.
26. Atkinson A J. Intracerebroventricular drug administration. Transl Clin Pharmacol. 2017; 25(3):117-124.
27. Bevan A K, Duque S, Foust K D, Morales P R, Braun L, Schmelzer L, et al. Systemic gene delivery in large species for targeting spinal cord, brain, and peripheral tissues for pediatric disorders. Mol Ther. 2011; 19(11): 1971-1980.
28. Bailey R M, Armao D, Nagabhushan Kalburgi S, Gray S J. Development of intrathecal AAV9 gene therapy for giant axonal neuropathy. Mol Ther Methods Clin. Dev. 2018; 9:160-171.
29. Bolon B, Garmin R H, Pardo I D, Jensen K, Sills R C, Roulois A, et al. STP position paper: recommended practices for sampling and processing the nervous system (brain, spinal cord, nerve, and eye) during nonclinical general toxicity studies. Toxicol Pathol. 2013; 41(7): 1028-1048.
30. Bolon B, Krinke G, Butt M T, Rao D B, Pardo I D, Jortner B S, et al. STP position paper: recommended best practices for sampling, processing, and analysis of the peripheral nervous system (nerves and somatic and autonomic ganglia) during nonclinical toxicity studies. Toxicol Pathol. 2018 June; 46(4):372-402.
31. Buccafusco J J. Methods of behavior analysis in neuroscience. In Fronteirs in Neuroscience. 2nd Ed. Boca Raton, FL: CRC Press/Taylor & Francis. 2009.
32. Caglayan A O, Comu S, Baranoski J F, Parman Y, Kaymakgalan H, Akgumus G T, et al. NGLY1 mutation causes neuromotor impairment, intellectual disability, and neuropathy. Eur J Med Genet. 2015; 58(1):39-43.

33. Cahan E M, Frick S L. Orthopaedic phenotyping of NGLY1 deficiency using an international, family-led disease registry. Orphanet J Rare Dis. 2019; 14(1):148.
34. Chou A H. Polyglutamine-expanded ataxin-3 causes cerebellar dysfunction of SCA3 transgenic mice by inducing transcriptional dysregulation. Neurobiol Dis. 2008; 31(1):89-101.
35. Colella P, Ronzitti G, Mingozzi F. Emerging issues in AAV-mediated in vivo gene therapy. Mol Ther Methods Clin Dev. 2017; 8:87-104.
36. Crawley J N. Behavioral phenotyping of rodents. Comp Med. 2003; 53:140-146.
37. Crawley J N. Behavioral phenotyping strategies for mutant mice. Neuron. 2008; 57(6):809-818.
38. Davidoff A M, Ng C Y C, Zhou J, Spence Y, Nathwani A C. Sex significantly influences transduction of murine liver by recombinant adeno-associated viral vectors through an androgen-dependent pathway. Blood. 2003; 102(2):480¬488.
39. Duan D. Systemic AAV micro-dystrophin gene therapy for Duchenne muscular dystrophy. Mol Ther. 2018; 26(10):2337-2356.
40. Enns G M, Shashi V, Bainbridge M, Gambello M J, Zahir F R, Gast T, et al. Mutations in NGLY1 cause an inherited disorder of the endoplasmic reticulum-associated degradation pathway. Genet Med. 2014; 16(10):751-758.
41. Foust K D, Wang X, McGovern V L, Braun L, Bevan A K, Haidet A M, et al. Rescue of the spinal muscular atrophy phenotype in a mouse model by early postnatal delivery of SMN. Nat Biotechnol. 2010; 28(3):271-274.
42. Fujihira H, Masahara-Negishi Y, Tamura M, Huang C, Harada Y, Wakana S, et al. Lethality of mice bearing a knockout of the Ngly1-gene is partially rescued by the additional deletion of the Engase gene. PLoS Genet. 2017; 13(4):e1006696.
43. Ge H, Wu Q, Lu H, Huang Y, Zhou T, Tan D, et al. Two novel compound heterozygous mutations in NGLY1 as a cause of congenital disorder of deglycosylation: a case presentation. BMC Med Genet. 2020; 21:135.
44. Greig J A, Nordin J M L, Draper C, McMenamin D, Chroscinski E A, Bell P, et al. Determining the minimally effective dose of a clinical candidate AAV vector in a mouse model of Crigler-Najjar syndrome. Mol Ther Methods Clin Dev. 2018; 10:237-244.
45. Guyenet S J, Furrer S A, Damian V M, Baughan T D, La Spada A R, Garden G A. A simple composite phenotype scoring system for evaluating mouse models of cerebellar ataxia. J Vis Exp. 2010; 21:1787.
46. Haijes H A, de Sain-van der Velden M G M, Prinsen H C M T, Willems A P, van der Ham M, Gerrits J, et al. Aspartylglycosamine is a biomarker for NGLY1-CDDG, a congenital disorder of deglycosylation. Mol Genet Metab. 2019; 127(4):368-372.
47. Hall P L, Lam C, Alexander J J, Asif G, Berry G T, Ferreira C, et al. Urine oligosaccharide screening by MALDI-TOF for the identification of NGLY1 deficiency. Mol Genet Metab. 2018; 124(1):82-86.
48. Harmatz P, Whitley C B, Wang R Y, Bauer M, Song W, Haller C, et al. A novel Blind Start study design to investigate vestronidase alfa for mucopolysaccharidosis VII, an ultra-rare genetic disease. Mol Genet Metab. 2018; 123(4):488-494.
49. Hendriksz C J, Giugliani R, Harmatz P, Mengel E, Haller C. Multi-domain impact of elosulfase alfa in Morquio A syndrome in the pivotal Phase III trial. Mol Genet Metab. 2015; 114(2):178-185.
50. Hirai T, Enomoto M, Kaburagi H, Sotome S, Yoshida-Tanaka K, Ukegawa M, et al. Intrathecal AAV serotype 9-mediated delivery of shRNA against TRPV1 attenuates thermal hyperalgesia in a mouse model of peripheral nerve injury. Mol Ther. 2014; 22(2):409-419.
51. Hocquemiller M, Giersch L, Audrain M, Parker S, Cartier N. Adeno-associated virus-based gene therapy for CNS diseases. Hum Gene Ther. 2016; 27(7):478-496.
52. Hordeaux J, Buza E L, Dyer C, Goode T, Mitchell T W, Richman L, et al. Adeno-associated virus-induced dorsal root ganglion pathology. Hum Gene Ther. 2020; 31(15-16):808-818.
53. Huang C, Harada Y, Hosomi A, Masahara-Negishi Y, Seino J, Fujihira H, et al. Endo-β-N-acetylglucosaminidase forms N-GlcNAc protein aggregates during E R-associated degradation in Ngly1-defective cells. Proc Natl Acad Sci USA. 2015; 112(5):1398-1403.
54. Huang R, Cathey S, Pollard L, Wood T. UPLC-M S/M S analysis of urinary free oligosaccharides for lysosomal storage diseases: diagnosis and potential treatment monitoring. Clin Chem. 2018; 64(12):1772-177.
55. Jackson K L, Dayton R D, Klein R L. AAV9 supports wide-scale transduction of the CNS and TDP-43 disease modeling in adult rats. Mol Ther Methods Clin Dev. 2015; 2:15036.
56. Lalonde R, Strazielle C. Brain regions and genes affecting limb-clasping responses. Brain Res Rev. 2011; 67(1-2):252-259.
57. Lam C, Wolfe L, Need A, Shashi V, Enns G. NGLY1-related congenital disorder of deglycosylation. In: Adam M P, Ardinger H H, Pagon R A, Wallace S E, Bean L J H, Stephens K, Amemiya A, editors. GeneReviews® [Internet]. Seattle (W A): University of Washington, Seattle; 1993-2019. 2018 Feb. 8.
58. Lam C, Ferreira C, Krasnewich D, Toro C, Latham L, Zein W M, et al. Prospective phenotyping of NGLY1-CDDG, the first congenital disorder of deglycosylation. Genet Med. 2017; 19(2):160-168.
59. Lanoix J, Acheson N H. A rabbit beta-globin polyadenylation signal directs efficient termination of transcription of polyomavirus DNA. EMBO J. 1988; 7(8):2515-2522.
60. Lehrbach N J, Breen P C, Ruvkun G. Protein sequence editing of SKN-1A/Nrfl by peptide:N-glycanase controls proteasome gene expression. Cell. 2019; 177(3):737-750.
61. Levitt N, Briggs D, Gil A, Proudfoot N J. Definition of an efficient synthetic poly(A) site. Genes Dev. 1989; 3(7):1019-1025.
62. Lipari Pinto P, Machado C, Janeiro P, Dupont J, Quintas S, Soiusa A B, et al. NGLY1 deficiency-A rare congenital disorder of deglycosylation. JIMD Rep. 2020; 53(1):2-9.
63. Lipinski P, Cielecka-Kuszyk J, Socha P, Tylki-Szymanska A. Liver involvement in NGLY1 congenital disorder of deglycosylation. Pol J Pathol. 2020a; 71(1):66-68.
64. Lipinski P, Bogdanska A, Ròżdżyǹska-Ṡwiatkowska A, Wierzbicka-Rucińska A, Tylki-Szymańska A. NGLY1 deficiency: novel patient, review of the literature and diagnostic algorithm. JIMID Rep. 2020b51(1):82-88.
65. Maguire C A, Crommentuijn M H, Mu D, Hudry E, Serrano-Pozo A, Hyman B T, et al. Mouse gender influences brain transduction by intravascularly administered AAV9. Mol Ther. 2013; 21(8):1470-1471.
66. Meadows A S, Pineda R J, Goodchild L, Bobo T A, Fu H. Threshold for pre-existing antibody levels limiting transduction efficiency of systemic rAAV9 gene delivery: relevance for translation. Mol Ther Methods Clin Dev. 2019; 13:453-462.

67. Meadows A S, Duncan F J, Camboni M, Waligura K, Montgomery C, Zaraspe K, et al. A GLP-compliant toxicology and biodistribution study: systemic delivery of an rAAV9 vector for the treatment of mucopolysaccharidosis IIIB. Hum Gene Ther Clin Dev. 2015; 26(4):228-242.
68. Mendell J R, Al-Zaidy S, Shell R, Arnold W D, Rodino-Klapac L R, Prior T W, et al. Single-dose gene-replacement therapy for spinal muscular atrophy. N Engl J Med. 2017; 377(18):1713-1722.
69. Miyazaki J, Takaki S, Araki K, Tashiro F, Tominaga A, Takatsu K, et al. Expression vector system based on the chicken beta-actin promoter directs efficient production of interleukin-5. Gene. 1989; 79(2):269-277.
70. Mononen T, Parviainen M, Penttila I, Mononen I. Liquid-chromatographic detection of aspartylglycosaminuria. Clin Chem. 1986; 32(3):501-502.
71. Mononen I, Mononen T, Ylikangas P, Kaartinen V, Savolainen K. Enzymatic diagnosis of aspartylglycosaminuria by fluorometric assay of glycosylasparaginase in serum, plasma, or lymphocytes. Clin Chem. 1994; 40(3): 38 5-388.
72. Moser V C, McCormick J P, Creason J P, MacPhail R C. Comparison of chlordimeform and carbaryl using a functional observational battery. Fund Appl Toxicol. 1988; 11(2):189-206.
73. Moser V C, Ross J F. U S EPA/AIHC Training video and reference manual for a functional observational battery. Washington, D. C.: U S Environmental Protection Agency. 1996.
74. Nakamura S, Muramatsu S I, Takino N, Ito M, Jimbo E F, Shimazaki K, et al. Gene therapy for Glut1-deficient mouse using an adeno-associated virus vector with the human intrinsic GLUT1 promoter. J Gene Med. 2018; 20(4):e3013.
75. Need A C, Shashi V, Hitomi Y, Schoch K, Shianna K V, McDonald M T, et al. Clinical application of exome sequencing in undiagnosed genetic conditions. J Med Genet. 2012; 49(6):353-561.
76. Neville D C, Field R A, Ferguson M A. Hydrophobic glycosides of N-acetylglucosamine can act as primers for polylactosamine synthesis and can affect glycolipid synthesis in vivo. Biochem J. 1995; 307(Pt 3)(Pt 3):791-797.
77. Niemir N, Rouviere L, Besse A, Vanier M T, Dmytrus J, Marais T, et al. Intravenous administration of scAAV9-Hexb normalizes lifespan and prevents pathology in Sandhoff disease mice. Hum Mol Genet. 2018; 27(6):954-968.
78. Niwa H, Yamamura K, Miyaxaki J. Efficient selection for high-expression transfectants with a novel eukaryotic vector. Gene. 1991; 108(2):193-199.
79. Nott A, Le Hir, H, Moore M J. Splicing enhances translation in mammalian cells: an additional function of the exon junction complex. Genes Dev. 2004; 18(2):210-222.
80. Panneman D M, Wortmann S B, Haaxma C A, van Hasselt P M, Wolf N I, Hendriks Y, et al. Variants in NGLY1 lead to intellectual disability, myoclonus epilepsy, sensorimotor axonal polyneuropathy and mitochondrial dysfunction. Clin Genet. 2020; 97(4):556-566.
81. Peyrl A, Chocholous M, Azizi A A, Czech T, Dorfer C, Mitteregger D, et al. Safety of Ommaya reservoirs in children with brain tumors: a 20-year experience with 5472 intraventricular drug administrations in 98 patients. J Neurooncol. 2014; 120(1):139-145.
82. Pinto P L, Machado C, Janeiro P, Dupont J, Quintas S, Sousa A B, et al. NGLY1 deficiency-A rare congenital disorder of deglycosylation. JIMD Rep. 2020; 53(1):2-9.
83. Powell S K, Rivera-Soto R, Gray S J. Viral expression cassette elements to enhance transgene target specificity and expression in gene therapy. Discov Med. 2015; 19(102):49-57.
84. Ren L, Gao G, Wang D. Optimizing in vivo NGLY1 gene delivery towards gene therapy for NGLY1 deficiency. American Society of Gene and Cell Therapy (ASGCT) 22nd Annual Meeting. 29 Apr. to 2 May 2019.
85. Robinson L, Platt B, Riedel G. Involvement of the cholinergic system in conditioning and perceptual memory. Behav Brain Res. 2011; 221(2):443-465.
86. Saade D, Bharucha-Goebel D, Jain M, Waite M, Norato G, Cheung K, et al. Review of safety and interim analysis of efficacy of a first-in-human intrathecal gene transfer study for giant axonal neuropathy. Presented at the 22$^{nd}$
87. Annual Meeting for the American Society of Gene and cell Therapy. Washington, D C. 29 Apr.-2 May 2019. Available at https://cslide-us.ctimeetingtech.com/asgct23/attendee/eposter/file/1348 #1. Accessed September 2020.
88. Samaranch L, Salegio E A, San Sebastian W, Kells A P, Bringas J R, Forsayeth J, et al. Strong cortical and spinal cord transduction after AAV7 and AAV9 delivery into the cerebrospinal fluid of nonhuman primates. Hum Gene Ther. 2013; 24(5):526-532.
89. Seibenhener M L, Wooten M C. Use of the open field maze to measure locomotor and anxiety-like behavior in mice. J Vis Exp. 2015; (96):e52434.
90. Suzuki T, Huang C, Fujihira H. The cytoplasmic peptide: N-glycanase (NGLY1)-structure, expression and cellular functions. Gene. 2016; 577(1):1-7.
91. Suzuki T, Yano K, Sugimoto S, Kitajima K, Lennarz W J, Inoue S, et al. Endo-beta-N-acetylglucosaminidase, an enzyme involved in processing of free oligosaccharides in the cytosol. Proc Natl Acad Sci USA. 2002a; 99(15): 9691-9696.
92. Suzuki T, Park H, Lennarz W J. Cytoplasmic peptide: N-glycanase (PNGase) in eukaryotic cells: occurrence, primary structure, and potential functions. FASEB J. 2002b; 16(7):635-641.
93. Suzuki T, Park H, Hollingsworth N M, Sternglanz R, Lennarz W J. PNG1, a yeast gene encoding a highly conserved peptide:N-glycanase. J Cell Biol. 2000; 149 (5):1039-1052.
94. Talsness D M, Owings K G, Coelho E, Mercenne G, Pleinis J M, Zuberi A R, et al. A Drosophila natural variation screen identifies NKCC1 as a substrate of NGLY1 deglycosylation and a modifier of NGLY1 deficiency. bioRxiv 2020.04.13.039651; doi: https://doi.org/10.1101/2020.04.13.039651
95. Tomlin F M, Gerling-Driessen UIM, Liu Y C, Flynn R A, Vangala J R, Lentz C S, et al. Inhibition of NGLY1 inactivates the transcription factor Nrfl and potentiates proteasome inhibitor cytotoxicity. ACS Cent Sci. 2017; 3(11):1143-1155.
96. Tornoe J, Kusk P, Johansen T E, Jensen P R. Generation of a synthetic mammalian promoter library by modification of sequences spacing transcription factor binding sites. Gene. 2002; 297(1-2):21-32.
97. Valencia P, Dias A P, Reed R. Splicing promotes rapid and efficient mRNA export in mammalian cells. Proc Natl Acad Sci USA. 2008; 105(9):3386-3391.
98. van Keulen B J, Rotteveel J, Finken M J J. Unexplained death in patients with NGLY1 mutations may be explained by adrenal insufficiency. Physiol Rep. 2019; 7(3):e13979.

99. Wright J F. Codon modification and PAMPs in clinical AAV vectors: the tortoise or the hare? Mol Ther. 2020; 28(3):701-703.
100. Xia B, Asif G, Arthur L, Pervaiz M A, Li X, Liu R, et al. Oligosaccharide analysis in urine by maldi-tof mass spectrometry for the diagnosis of lysosomal storage diseases. Clin Chem. 2013; 59(9):1357-1368.
101. Zanta-Boussif M A, Charrier S, Brice-Ouset A, Martin S, Opolon P, Thrasher A J, et al. Validation of a mutated PRE sequence allowing high and sustained transgene expression while abrogating WHV-X protein synthesis: application to the gene therapy of WAS. Gene Ther. 2009; 16(5):605-619.
102. Zhou X, Zhao G, Truglio J J, Wang L, Li G, Lennarz W J, et al. Structural and biochemical studies of the C-terminal domain of mouse peptide-N-glycanase identify it as a mannose-binding module. Proc Natl Acad Sci USA. 2006; 103(46):17214-17219.
103. Zhu J, Li Y, Wang Z, Jia W, Xu R. Toll-like receptor 4 deficiency impairs motor coordination. Front Neurosci. 2016; 10:33.
104. Zolgensma® (onasemnogene abeparvovec-xioi) USPI. Revised May 2019. AveXis, Inc. Bannockburn, I L, USA. Accessed June 2019.
105. Mathai, S. C., et al., *The minimal important difference in the 6-minute walk test for patients with pulmonary arterial hypertension*. Am J Respir Crit Care Med, 2012. 186(5): p. 428-33.
106. Okuyama, T., et al., *Japan Elaprase Treatment (JET) study: idursulfase enzyme replacement therapy in adult patients with attenuated Hunter syndrome (Mucopolysaccharidosis II, MPS II)*. Mol Genet Metab, 2010. 99(1): p. 18-25.
107. *Photodynamic therapy of subfoveal choroidal neovascularization in age-related macular degeneration with verteporfin: one-year results of 2 randomized clinical trials—TAP report. Treatment of age-related macular degeneration with photodynamic therapy (TAP) Study Group*. Arch Ophthalmol, 1999. 117(10): p. 1329-45.
108. Ferris, F. L., 3rd, et al., *New visual acuity charts for clinical research*. Am J Ophthalmol, 1982. 94(1): p. 91-6.
109. Reeves, B. C., J. M. Wood, and A. R. Hill, *Reliability of high-and low-contrast letter charts*. Ophthalmic Physiol Opt, 1993. 13(1): p. 17-26.
110. Wuang, Y. P. and C. Y. Su, *Reliability and responsiveness of the Bruininks-Oseretsky Test of Motor Proficiency-Second Edition in children with intellectual disability*. Res Dev Disabil, 2009. 30(5): p. 847-55.
111. Wang, R. Y., et al., *The long-term safety and efficacy of vestronidase alfa, rhGUS enzyme replacement therapy, in subjects with mucopolysaccharidosis VII*. Mol Genet Metab, 2020. 129(3): p. 219-227.
112. Little, R. J. A. and Rubin, D. B. Statistical Analysis With Missing Data. 2nd ed. Princeton, N J: Wiley: 2002.

What is claimed is:

1. A method for treating N-glycanase 1 (NGLY1) deficiency in a subject in need thereof, the method comprising administering to the subject by intracerebroventricular administration or via the cisterna magna a therapeutically effective amount of a recombinant adeno-associated virus (rAAV) comprising a nucleic acid construct comprising the nucleotide sequence of SEQ ID NO: 8.

2. The method of claim 1, wherein the nucleic acid construct is flanked by adeno-associated virus-2 inverted terminal repeats.

3. The method of claim 1, wherein the rAAV is an AAV9 serotype or has a capsid that is at least 95% identical to SEQ ID NO: 10 (AAV9 sequence).

4. The method of claim 1, wherein at least 5 weeks after administration, the level of GlcNAc-Asn (GNA) in the plasma, urine or other tissue sample is reduced by between 10% and 90% compared to the level of GNA in the plasma, urine, cerebrospinal fluid or other tissue sample in the patient before said administration.

5. The method of claim 1, wherein at least 5 to 30 weeks after said administration there is a reduction or amelioration in one or more symptoms of NGLY1 deficiency in said patient relative to the symptom in the patient prior to said administration.

6. An rAAV comprising an AAV9 capsid containing a nucleic acid construct comprising the nucleotide sequence of SEQ ID NO: 8.

7. A pharmaceutical composition comprising the rAAV of claim 6.

8. The pharmaceutical composition of claim 7, which comprises phosphate buffered saline, pH 7.3 and 0.001% PF68.

9. A method of reducing accumulation of GlcNAc-Asn (GNA) in the central nervous system of a subject, the method comprising administering to the subject by intracerebroventricular administration or via the cisterna magna a therapeutically effective amount of a recombinant adeno-associated virus (rAAV) comprising a nucleic acid construct comprising the nucleotide sequence of SEQ ID NO: 8.

10. The method of claim 9, wherein the rAAV is an AAV9 serotype or has a capsid that is at least 95% identical to SEQ ID NO: 10 (AAV9 sequence).

11. The method of claim 9, wherein at least 5 to 30 weeks after administration, the level of GNA in the plasma, urine or other tissue sample is reduced by 10%, 20%, 50%, 75% or 90% compared to the level of GNA in the plasma, urine or other tissue sample in the patient before said administration.

12. A pharmaceutical composition for treatment of N-glycanase 1 (NGLY1) deficiency in a subject in need thereof, wherein the pharmaceutical composition comprises an rAAV of claim 6.

13. The pharmaceutical composition of claim 12, wherein the pharmaceutical composition is administered to the subject in a therapeutically effective amount selected from the group of intravenous administration, intracerebroventricular administration, cisterna magna administration or a combination thereof.

* * * * *

SEQUENCE LISTING

```
<160> NUMBER OF SEQ ID NOS: 11

<210> SEQ ID NO 1
<211> LENGTH: 1965
<212> TYPE: DNA
<213> ORGANISM: Artificial Sequence
<220> FEATURE:
<223> OTHER INFORMATION: Synthetic construct

<400> SEQUENCE: 1

atggccgctg ctgccctggg atcatcaagt gggtccgctt cacctgccgt cgccgaactg      60

tgccagaaca cccccgaaac cttcctggag gcatccaagc tgctgctgac ctacgccgac     120

aacatcctgc gcaatccaaa cgatgagaag tatcgctcca tcaggatcgg caataccgcc     180

ttctctacaa ggctgctgcc cgtgagggga gcagtggagt gcctgttcga gatgggcttt     240

gaggagggcg agacacacct gatctttccc aagaaggcca gcgtggagca gctgcagaag     300

atcagggacc tgatcgccat cgagagaagc tcccggctgg atggctctaa caagagccac     360

aaggtgaagt ctagccagca gcctgcagca agcacacagc tgcctaccac accatcctct     420

aatccatccg gcctgaacca gcacaccagg aatagacagg gacagagctc cgacccacct     480

agcgcctcca cagtggcagc cgattctgcc atcctggagg tgctgcagag caacatccag     540

cacgtgctgg tgtacgagaa tccagccctg caggagaagg ccctggcatg catcccagtg     600

caggagctga agcggaagag ccaggagaag ctgtccaggg caaggaagct ggacaagggc     660

atcaatatca gcgacgagga tttcctgctg ctggagctgc tgcactggtt taaggaggag     720

ttctttcact gggtgaacaa tgtgctgtgc tccaagtgtg gcggccagac caggagcaga     780

gatcggtccc tgctgccttc tgacgatgag ctgaagtggg gcgccaagga ggtggaggac     840

cactactgcg atgcctgtca gttctccaac cgctttccca ggtataacaa tcctgagaag     900

ctgctggaga caagatgcgg ccggtgtggc gagtgggcca attgtttcac actgtgctgt     960
```

-continued

```
agagccgtgg gctttgaggc cagatacgtg tgggactata ccgatcacgt gtggacagag   1020

gtgtactctc ccagccagca gagatggctg cactgcgacg cctgtgagga cgtgtgcgat   1080

aagcctctgc tgtacgagat cggctggggc aagaagctgt cttatgtgat cgccttcagc   1140

aaggacgagg tggtggatgt gacctggcgg tatagctgta agcacgagga agtgatcgcc   1200

aggagaacca aggtgaagga ggccctgctg cgcgacacaa tcaatggcct gaacaagcag   1260

aggcagctgt tcctgtccga gaaccggcgc aaggagctgc tgcagaggat catcgtggag   1320

ctggtggagt ttatctctcc taagacccca aagccaggag agctgggagg aaggatctcc   1380

ggctctgtgg cctggcgcgt ggccaggggc gagatgggcc tgcagaggaa ggagacactg   1440

ttcatcccat gcgagaacga gaagatctct aagcagctgc acctgtgcta caatatcgtg   1500

aaggacagat atgtgcgggt gtccaacaat aaccagacca tctctggctg ggagaacggc   1560

gtgtggaaga tggagagcat ctttagaaag gtggagacag attggcacat ggtgtacctg   1620

gcccggaagg agggctctag cttcgcctat atcagctgga agtttgagtg tggctccgtg   1680

ggcctgaagg tggacagcat ctccatcaga acctcctctc agacattcca gaccggcaca   1740

gtggagtgga agctgaggtc cgataccgcc caggtggagc tgacaggcga caattccctg   1800

cactcttacg ccgatttctc tggcgccacc gaagtgatcc tggaggcaga gctgagcagg   1860

ggcgacggcg atgtggcctg gcagcacaca cagctgttta ggcagagcct gaacgaccac   1920

gaggagaatt gcctggagat tattatcaag ttttccgacc tgtga                   1965


<210> SEQ ID NO 2
<211> LENGTH: 259
<212> TYPE: DNA
<213> ORGANISM: Artificial Sequence
<220> FEATURE:
<223> OTHER INFORMATION: Synthetic construct

<400> SEQUENCE: 2

cacgttctgc ttcactctcc ccatctcccc cccctcccca cccccaattt tgtatttatt     60

tattttttaa ttattttgtg cagcgatggg ggcggggggg gggggcgcgc gccaggcggg    120

gcggggcggg gcgaggggcg gggcggggcg aggcggagag gtgcggcggc agccaatcag    180

agcggcgcgc tccgaaagtt tccttttatg gcgaggcggc ggcggcggcg gccctataaa    240

aagcgaagcg cgcggcggg                                                 259


<210> SEQ ID NO 3
<211> LENGTH: 382
<212> TYPE: DNA
<213> ORGANISM: Artificial Sequence
<220> FEATURE:
<223> OTHER INFORMATION: Synthetic construct

<400> SEQUENCE: 3

ctagtcgaca ttgattattg actagttatt aatagtaatc aattacgggg tcattagttc     60

atagcccata tatggagttc cgcgttacat aacttacggt aaatggcccg cctggctgac    120

cgcccaacga cccccgccca ttgacgtcaa taatgacgta tgttcccata gtaacgccaa    180

tagggacttt ccattgacgt caatgggtgg agtatttacg gtaaactgcc cacttggcag    240

tacatcaagt gtatcatatg ccaagtacgc cccctattga cgtcaatgac ggtaaatggc    300

ccgcctggca ttatgcccag tacatgacct tatgggactt tcctacttgg cagtacatct    360

acgtattagt catcgctatt ac                                             382
```

<210> SEQ ID NO 4
<211> LENGTH: 658
<212> TYPE: DNA
<213> ORGANISM: Artificial Sequence
<220> FEATURE:
<223> OTHER INFORMATION: Synthetic construct

<400> SEQUENCE: 4
ctagtcgaca ttgattattg actagttatt aatagtaatc aattacgggg tcattagttc 60
atagcccata tatggagttc cgcgttacat aacttacggt aaatggcccg cctggctgac 120
cgcccaacga cccccgccca ttgacgtcaa taatgacgta tgttcccata gtaacgccaa 180
tagggacttt ccattgacgt caatgggtgg agtatttacg gtaaactgcc cacttggcag 240
tacatcaagt gtatcatatg ccaagtacgc cccctattga cgtcaatgac ggtaaatggc 300
ccgcctggca ttatgcccag tacatgacct tatgggactt tcctacttgg cagtacatct 360
acgtattagt catcgctatt accatgtcga ggacgcgtcc acgttctgct tcactctccc 420
catctccccc ccctccccac ccccaatttt gtatttattt atttttttaat tattttgtgc 480 agcgatgggg gcgggggggg ggggcgcgcg ccaggcgggg cggggcgggg cgaggggcgg 540
ggcggggcga ggcggagagg tgcggcggca gccaatcaga gcggcgcgct ccgaaagttt 600
ccttttatgg cgaggcggcg gcggcggcgg ccctataaaa agcgaagcgc gcggcggg 658

<210> SEQ ID NO 5
<211> LENGTH: 301
<212> TYPE: DNA
<213> ORGANISM: Artificial Sequence
<220> FEATURE:
<223> OTHER INFORMATION: Synthetic construct

<400> SEQUENCE: 5
tattgcggta gtttatcaca gttaaattgc taacgcagtc agtgcttctg acacaacagt 60
ctcgaactta agctgcagaa gttggtcgtg aggcactggg caggtaagta tcaaggttac 120
aagacaggtt taaggagacc aatagaaact gggcttgtcg agacagagaa gactcttgcg 180
tttctgatag gcacctattg gtcttactga catccacttt gcctttctct ccacaggcag 240
tgtccactcc cagttcaatt acagctctta aggctagagt acttaatacg actcactata 300
g 301

<210> SEQ ID NO 6
<211> LENGTH: 589
<212> TYPE: DNA
<213> ORGANISM: Artificial Sequence
<220> FEATURE:
<223> OTHER INFORMATION: Synthetic construct

<400> SEQUENCE: 6
aatcaacctc tggattacaa aatttgtgaa agattgactg gtattcttaa ctatgttgct 60
ccttttacgc tatgtggata cgctgcttta atgcctttgt atcatgctat tgcttcccgt 120
atggctttca ttttctcctc cttgtataaa tcctggttgc tgtctcttta tgaggagttg 180
tggcccgttg tcaggcaacg tggcgtggtg tgcactgtgt ttgctgacgc aacccccact 240
ggttggggca ttgccaccac ctgtcagctc ctttccggga ctttcgcttt ccccctccct 300
attgccacgg cggaactcat cgccgcctgc cttgcccgct gctggacagg ggctcggctg 360
ttgggcactg acaattccgt ggtgttgtcg gggaaatcat cgtcctttcc ttggctgctc 420
gcctgtgttg ccacctggat tctgcgcggg acgtccttct gctacgtccc ttcggccctc 480
aatccagcgg accttccttc ccgcggcctg ctgccggctc tgcggcctct tccgcgtctt 540
cgccttcgcc ctcagacgag tcggatctcc ctttgggccg cctccccgc 589

<210> SEQ ID NO 7
<211> LENGTH: 127
<212> TYPE: DNA
<213> ORGANISM: Artificial Sequence
<220> FEATURE:
<223> OTHER INFORMATION: Synthetic construct

<400> SEQUENCE: 7
gatctttttc cctctgccaa aaattatggg gacatcatga agccccttga gcatctgact 60
tctggctaat aaaggaaatt tattttcatt gcaatagtgt gttggaattt tttgtgtctc 120
tcactcg 127

<210> SEQ ID NO 8
<211> LENGTH: 3677
<212> TYPE: DNA
<213> ORGANISM: Artificial Sequence
<220> FEATURE:
<223> OTHER INFORMATION: Synthetic construct

<400> SEQUENCE: 8
ctagtcgaca ttgattattg actagttatt aatagtaatc aattacgggg tcattagttc 60
atagcccata tatggagttc cgcgttacat aacttacggt aaatggcccg cctggctgac 120
cgcccaacga cccccgccca ttgacgtcaa taatgacgta tgttcccata gtaacgccaa 180
tagggacttt ccattgacgt caatgggtgg agtatttacg gtaaactgcc cacttggcag 240
tacatcaagt gtatcatatg ccaagtacgc cccctattga cgtcaatgac ggtaaatggc 300
ccgcctggca ttatgcccag tacatgacct tatgggactt tcctacttgg cagtacatct 360
acgtattagt catcgctatt accatgtcga ggacgcgtcc acgttctgct tcactctccc 420
catctccccc ccctccccac ccccaatttt gtatttattt atttttaat tattttgtgc 480 agcgatgggg gcgggggggg ggggcgcgcg ccaggcgggg cggggcgggg cgaggggcgg 540
ggcggggcga ggcggagagg tgcggcggca gccaatcaga gcggcgcgct ccgaaagttt 600
ccttttatgg cgaggcggcg gcggcggcgg ccctataaaa agcgaagcgc gcggcgggcg 660
ggagcaagct ttattgcggt agtttatcac agttaaattg ctaacgcagt cagtgcttct 720
gacacaacag tctcgaactt aagctgcaga agttggtcgt gaggcactgg gcaggtaagt 780
atcaaggtta caagacaggt ttaaggagac caatagaaac tgggcttgtc gagacagaga 840
agactcttgc gtttctgata ggcacctatt ggtcttactg acatccactt tgcctttctc 900
tccacaggca gtgtccactc ccagttcaat tacagctctt aaggctagag tacttaatac 960
gactcactat aggaattcgc caccatggcc gctgctgccc tgggatcatc aagtgggtcc 1020
gcttcacctg ccgtcgccga actgtgccag aacacccccg aaaccttcct ggaggcatcc 1080
aagctgctgc tgacctacgc cgacaacatc ctgcgcaatc caaacgatga gaagtatcgc 1140
tccatcagga tcggcaatac cgccttctct acaaggctgc tgcccgtgag gggagcagtg 1200
gagtgcctgt tcgagatggg ctttgaggag ggcgagacac acctgatctt tcccaagaag 1260
gccagcgtgg agcagctgca gaagatcagg gacctgatcg ccatcgagag aagctcccgg 1320
ctggatggct ctaacaagag ccacaaggtg aagtctagcc agcagcctgc agcaagcaca 1380
cagctgccta ccacaccatc ctctaatcca tccggcctga accagcacac caggaataga 1440
cagggacaga gctccgaccc acctagcgcc tccacagtgg cagccgattc tgccatcctg 1500
gaggtgctgc agagcaacat ccagcacgtg ctggtgtacg agaatccagc cctgcaggag 1560
aaggccctgg catgcatccc agtgcaggag ctgaagcgga agagccagga gaagctgtcc 1620
agggcaagga agctggacaa gggcatcaat atcagcgacg aggatttcct gctgctggag 1680
ctgctgcact ggtttaagga ggagttcttt cactgggtga acaatgtgct gtgctccaag 1740
tgtggcggcc agaccaggag cagagatcgg tccctgctgc cttctgacga tgagctgaag 1800
tggggcgcca aggaggtgga ggaccactac tgcgatgcct gtcagttctc caaccgcttt 1860
cccaggtata acaatcctga gaagctgctg gagacaagat gcggccggtg tggcgagtgg 1920
gccaattgtt tcacactgtg ctgtagagcc gtgggctttg aggccagata cgtgtgggac 1980
tataccgatc acgtgtggac agaggtgtac tctcccagcc agcagagatg gctgcactgc 2040
gacgcctgtg aggacgtgtg cgataagcct ctgctgtacg agatcggctg gggcaagaag 2100
ctgtcttatg tgatcgcctt cagcaaggac gaggtggtgg atgtgacctg gcggtatagc 2160
tgtaagcacg aggaagtgat cgccaggaga accaaggtga aggaggccct gctgcgcgac 2220
acaatcaatg gcctgaacaa gcagaggcag ctgttcctgt ccgagaaccg gcgcaaggag 2280
ctgctgcaga ggatcatcgt ggagctggtg gagtttatct ctcctaagac cccaaagcca 2340
ggagagctgg gaggaaggat ctccggctct gtggcctggc gcgtggccag ggcgagatg 2400 ggcctgcaga ggaaggagac actgttcatc ccatgcgaga acgagaagat ctctaagcag 2460
ctgcacctgt gctacaatat cgtgaaggac agatatgtgc gggtgtccaa caataaccag 2520
accatctctg gctgggagaa cggcgtgtgg aagatggaga gcatctttag aaaggtggag 2580
acagattggc acatggtgta cctggcccgg aaggagggct ctagcttcgc ctatatcagc 2640
tggaagtttg agtgtggctc cgtgggcctg aaggtggaca gcatctccat cagaacctcc 2700
tctcagacat tccagaccgg cacagtggag tggaagctga ggtccgatac cgcccaggtg 2760
gagctgacag gcgacaattc cctgcactct tacgccgatt tctctggcgc caccgaagtg 2820
atcctggagg cagagctgag caggggcgac ggcgatgtgg cctggcagca cacacagctg 2880
tttaggcaga gcctgaacga ccacgaggag aattgcctgg agattattat caagttttcc 2940
gacctgtgac tcgagaatca acctctggat tacaaaattt gtgaaagatt gactggtatt 3000
cttaactatg ttgctccttt tacgctatgt ggatacgctg ctttaatgcc tttgtatcat 3060
gctattgctt cccgtatggc tttcattttc tcctccttgt ataaatcctg gttgctgtct 3120
ctttatgagg agttgtggcc cgttgtcagg caacgtggcg tggtgtgcac tgtgtttgct 3180
gacgcaaccc ccactggttg gggcattgcc accacctgtc agctcctttc cgggactttc 3240
gctttccccc tccctattgc cacggcggaa ctcatcgccg cctgccttgc ccgctgctgg 3300
acaggggctc ggctgttggg cactgacaat tccgtggtgt tgtcggggaa atcatcgtcc 3360
tttccttggc tgctcgcctg tgttgccacc tggattctgc gcgggacgtc cttctgctac 3420
gtcccttcgg ccctcaatcc agcggacctt ccttcccgcg gcctgctgcc ggctctgcgg 3480
cctcttccgc gtcttcgcct tcgccctcag acgagtcgga tctccctttg ggccgcctcc 3540
ccgcatcgat gatctttttc cctctgccaa aaattatggg gacatcatga agccccttga 3600
gcatctgact tctggctaat aaaggaaatt tattttcatt gcaatagtgt gttggaattt 3660
tttgtgtctc tcactcg 3677

<210> SEQ ID NO 9
<211> LENGTH: 3972
<212> TYPE: DNA

<213> ORGANISM: Artificial Sequence
<220> FEATURE:
<223> OTHER INFORMATION: Synthetic construct

<400> SEQUENCE: 9
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcct agtcgacatt gattattgac tagttattaa tagtaatcaa 180
ttacggggtc attagttcat agcccatata tggagttccg cgttacataa cttacggtaa 240
atggcccgcc tggctgaccg cccaacgacc cccgcccatt gacgtcaata atgacgtatg 300
ttcccatagt aacgccaata gggactttcc attgacgtca atgggtggag tatttacggt 360
aaactgccca cttggcagta catcaagtgt atcatatgcc aagtacgccc cctattgacg 420
tcaatgacgg taaatggccc gcctggcatt atgcccagta catgacctta tgggactttc 480
ctacttggca gtacatctac gtattagtca tcgctattac catgtcgagg acgcgtccac 540
gttctgcttc actctcccca tctccccccc ctccccaccc ccaattttgt atttatttat 600
tttttaatta ttttgtgcag cgatgggggc gggggggggg ggcgcgcgcc aggcggggcg 660
gggcggggcg aggggcgggg cggggcgagg cggagaggtg cggcggcagc caatcagagc 720
ggcgcgctcc gaaagtttcc ttttatggcg aggcggcggc ggcggcggcc ctataaaaag 780
cgaagcgcgc ggcgggcggg agcaagcttt attgcggtag tttatcacag ttaaattgct 840
aacgcagtca gtgcttctga cacaacagtc tcgaacttaa gctgcagaag ttggtcgtga 900
ggcactgggc aggtaagtat caaggttaca agacaggttt aaggagacca atagaaactg 960
ggcttgtcga gacagagaag actcttgcgt ttctgatagg cacctattgg tcttactgac 1020
atccactttg cctttctctc cacaggcagt gtccactccc agttcaatta cagctcttaa 1080
ggctagagta cttaatacga ctcactatag gaattcgcca ccatggccgc tgctgccctg 1140
ggatcatcaa gtgggtccgc ttcacctgcc gtcgccgaac tgtgccagaa caccccccgaa 1200 accttcctgg aggcatccaa gctgctgctg acctacgccg acaacatcct gcgcaatcca 1260
aacgatgaga agtatcgctc catcaggatc ggcaataccg ccttctctac aaggctgctg 1320
cccgtgaggg gagcagtgga gtgcctgttc gagatgggct ttgaggaggg cgagacacac 1380
ctgatctttc ccaagaaggc cagcgtggag cagctgcaga agatcaggga cctgatcgcc 1440
atcgagagaa gctcccggct ggatggctct aacaagagcc acaaggtgaa gtctagccag 1500
cagcctgcag caagcacaca gctgcctacc acaccatcct ctaatccatc cggcctgaac 1560
cagcacacca ggaatagaca gggacagagc tccgacccac ctagcgcctc cacagtggca 1620
gccgattctg ccatcctgga ggtgctgcag agcaacatcc agcacgtgct ggtgtacgag 1680
aatccagccc tgcaggagaa ggccctggca tgcatcccag tgcaggagct gaagcggaag 1740
agccaggaga agctgtccag ggcaaggaag ctggacaagg gcatcaatat cagcgacgag 1800
gatttcctgc tgctggagct gctgcactgg tttaaggagg agttctttca ctgggtgaac 1860
aatgtgctgt gctccaagtg tggcggccag accaggagca gagatcggtc cctgctgcct 1920
tctgacgatg agctgaagtg gggcgccaag gaggtggagg accactactg cgatgcctgt 1980
cagttctcca accgctttcc caggtataac aatcctgaga agctgctgga gacaagatgc 2040
ggccggtgtg gcgagtgggc caattgtttc acactgtgct gtagagccgt gggctttgag 2100
gccagatacg tgtgggacta taccgatcac gtgtggacag aggtgtactc tcccagccag 2160
cagagatggc tgcactgcga cgcctgtgag gacgtgtgcg ataagcctct gctgtacgag 2220
atcggctggg gcaagaagct gtcttatgtg atcgccttca gcaaggacga ggtggtggat 2280
gtgacctggc ggtatagctg taagcacgag gaagtgatcg ccaggagaac caaggtgaag 2340
gaggccctgc tgcgcgacac aatcaatggc ctgaacaagc agaggcagct gttcctgtcc 2400
gagaaccggc gcaaggagct gctgcagagg atcatcgtgg agctggtgga gtttatctct 2460
cctaagaccc caaagccagg agagctggga ggaaggatct ccggctctgt ggcctggcgc 2520
gtggccaggg gcgagatggg cctgcagagg aaggagacac tgttcatccc atgcgagaac 2580
gagaagatct ctaagcagct gcacctgtgc tacaatatcg tgaaggacag atatgtgcgg 2640
gtgtccaaca ataaccagac catctctggc tgggagaacg gcgtgtggaa gatggagagc 2700
atctttagaa aggtggagac agattggcac atggtgtacc tggcccggaa ggagggctct 2760
agcttcgcct atatcagctg gaagtttgag tgtggctccg tgggcctgaa ggtggacagc 2820
atctccatca gaacctcctc tcagacattc cagaccggca cagtggagtg gaagctgagg 2880
tccgataccg cccaggtgga gctgacaggc gacaattccc tgcactctta cgccgatttc 2940
tctggcgcca ccgaagtgat cctggaggca gagctgagca ggggcgacgg cgatgtggcc 3000
tggcagcaca cacagctgtt taggcagagc ctgaacgacc acgaggagaa ttgcctggag 3060
attattatca agttttccga cctgtgactc gagaatcaac ctctggatta caaaatttgt 3120
gaaagattga ctggtattct taactatgtt gctcctttta cgctatgtgg atacgctgct 3180
ttaatgcctt tgtatcatgc tattgcttcc cgtatggctt tcattttctc ctccttgtat 3240
aaatcctggt tgctgtctct ttatgaggag ttgtggcccg ttgtcaggca acgtggcgtg 3300
gtgtgcactg tgtttgctga cgcaaccccc actggttggg gcattgccac cacctgtcag 3360
ctcctttccg ggactttcgc tttccccctc cctattgcca cggcggaact catcgccgcc 3420
tgccttgccc gctgctggac aggggctcgg ctgttgggca ctgacaattc cgtggtgttg 3480
tcggggaaat catcgtcctt tccttggctg ctcgcctgtg ttgccacctg gattctgcgc 3540
gggacgtcct tctgctacgt cccttcggcc ctcaatccag cggaccttcc ttcccgcggc 3600
ctgctgccgg ctctgcggcc tcttccgcgt cttcgccttc gccctcagac gagtcggatc 3660
tccctttggg ccgcctcccc gcatcgatga tctttttccc tctgccaaaa attatgggga 3720
catcatgaag ccccttgagc atctgacttc tggctaataa aggaaattta ttttcattgc 3780
aatagtgtgt tggaattttt tgtgtctctc actcgcggac cgagcggccg caggaacccc 3840
tagtgatgga gttggccact ccctctctgc gcgctcgctc gctcactgag gccgggcgac 3900
caaaggtcgc ccgacgcccg ggctttgccc gggcggcctc agtgagcgag cgagcgcgca 3960
gctgcctgca gg 3972

<210> SEQ ID NO 10
<211> LENGTH: 736
<212> TYPE: PRT
<213> ORGANISM: Artificial Sequence
<220> FEATURE:
<223> OTHER INFORMATION: Synthetic construct

<400> SEQUENCE: 10

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

```
Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460
```

```
Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 11
<211> LENGTH: 3719
<212> TYPE: DNA
<213> ORGANISM: Artificial Sequence
<220> FEATURE:
<223> OTHER INFORMATION: Synthetic construct

<400> SEQUENCE: 11

ctagtcgaca ttgattattg actagttatt aatagtaatc aattacgggg tcattagttc      60

atagcccata tatggagttc cgcgttacat aacttacggt aaatggcccg cctggctgac     120

cgcccaacga cccccgccca ttgacgtcaa taatgacgta tgttcccata gtaacgccaa     180

tagggacttt ccattgacgt caatgggtgg agtatttacg gtaaactgcc cacttggcag     240

tacatcaagt gtatcatatg ccaagtacgc cccctattga cgtcaatgac ggtaaatggc     300

ccgcctggca ttatgcccag tacatgacct tatgggactt tcctacttgg cagtacatct     360

acgtattagt catcgctatt accatgtcga ggacgcgtcc acgttctgct tcactctccc     420

catctccccc ccctccccac ccccaatttt gtatttattt atttttttaat tattttgtgc     480

agcgatgggg gcgggggggg ggggcgcgcg ccaggcgggg cggggcgggg cgaggggcgg     540
```

-continued

```
ggcggggcga ggcggagagg tgcggcggca gccaatcaga gcggcgcgct ccgaaagttt    600
cctttatgg cgaggcggcg gcggcggcgg ccctataaaa agcgaagcgc gcggcgggcg    660
ggagcaagct ttattgcggt agtttatcac agttaaattg ctaacgcagt cagtgcttct    720
gacacaacag tctcgaactt aagctgcaga agttggtcgt gaggcactgg gcaggtaagt    780
atcaaggtta caagacaggt ttaaggagac caatagaaac tgggcttgtc gagacagaga    840
agactcttgc gtttctgata ggcacctatt ggtcttactg acatccactt tgcctttctc    900
tccacaggca gtgtccactc ccagttcaat tacagctctt aaggctagag tacttaatac    960
gactcactat aggaattcgc caccatggct gcagctgcac tggggtcctc ttccggctcc   1020
gcttctcctg ctgttgctga actgtgtcaa aatacaccag aaacattttt agaagcatct   1080
aaattactgt taacatatgc cgataatata ctgagaaatc ccaatgacga aaagtataga   1140
tctattagaa ttggaaatac agctttttct actagactgt tacctgttag aggagccgtt   1200
gaatgtctgt ttgaaatggg attcgaagaa ggcgaaacac atctgatttt tcctaagaaa   1260
gcatcagttg aacaactgca aaaaattagg gacctgattg ccatagagag aagtagcaga   1320
ttagatggct ccaataagag ccacaaagta aagtcatccc agcaacctgc agcctccaca   1380
caactcccca caaccccatc ttcaaatcct agtggattaa atcaacatac aagaaataga   1440
caaggacaat cttctgatcc tccatctgct tcaactgtgg ctgctgattc tgctatttta   1500
gaagttctcc aatctaatat tcaacatgtt ctcgtttatg aaaatcctgc tttacaagaa   1560
aaagcattag cttgtatacc agtccaagaa ttaaaaagaa aatcacaaga aaaactctcc   1620
agagctagaa aattagataa aggtattaat ataagtgatg aagattttct gttgctggaa   1680
ttattgcatt ggtttaaaga agaatttttt cattgggtga ataatgtgtt atgttccaag   1740
tgtggaggac aaactagatc cagagataga tcattattac ctagtgatga tgaactgaaa   1800
tggggtgcca aagaggtgga ggatcactat tgtgatgctt gccaatttag caatagattt   1860
ccaagatata acaatcccga aaagttactg gaaacaagat gtggaagatg tggagaatgg   1920
gctaattgtt ttacactgtg ttgtagagct gtgggatttg aagctagata tgtttgggat   1980
tacacagacc atgtgtggac agaggtctat agcccttccc aacagagatg gctccactgt   2040
gatgcctgtg aggatgtgtg tgacaaaccc ttattatatg agataggatg gggaaagaaa   2100
ctgtcttatg tgattgcatt ctcaaaggat gaggtggtgg atgtcacctg gagatatagc   2160
tgtaaacatg aggaggtgat tgccagaaga accaaggtga aggaggcatt acttagagac   2220
accattaatg gacttaataa acagagacaa ctgtttctgt ccgaaaacag aagaaaagaa   2280
cttctccaga gaattattgt ggagttggtg gaatttatct ctcccaagac cccccaagcct   2340
ggagagctcg gggaagaat ctctggatca gtggcctgga gagttgccag aggagagatg   2400
ggactgcaga gaaaggagac tctgttcatc ccctgtgaga atgagaagat ctctaaacag   2460
ctccacctgt gttacaatat tgtgaaagat agatatgtta gagtgtcaaa caacaatcag   2520
accatttctg gatgggagaa tggagtgtgg aaaatggaat ctatcttcag aaaagtggaa   2580
acagattggc atatggtgta tctggcaaga aaggaaggtt cctcttttgc ttacatctcc   2640
tggaagttcg agtgcgggtc tgttggactg aaagtggatt ctatctccat tagaacaagc   2700
agtcaaacct ttcagacagg aacagtggaa tggaaactga ggagcgatac agcccaagtg   2760
gaactgacag gagataactc cctccactcc tatgctgatt tttctggtgc cacagaagtg   2820
attctggaag cagaactgtc cagaggagat ggtgatgtgg cttggcaaca cacccagtta   2880
ttcagacaat ctctgaatga ccatgaggaa aactgtctgg agatcattat caaattcagt   2940
```

-continued

```
gacctgggta agcctatccc taaccctctc ctcggtctcg attctacgtg actcgagaat   3000

caacctctgg attacaaaat ttgtgaaaga ttgactggta ttcttaacta tgttgctcct   3060

tttacgctat gtggatacgc tgctttaatg cctttgtatc atgctattgc ttcccgtatg   3120

gctttcattt tctcctcctt gtataaatcc tggttgctgt ctctttatga ggagttgtgg   3180

cccgttgtca ggcaacgtgg cgtggtgtgc actgtgtttg ctgacgcaac ccccactggt   3240

tggggcattg ccaccacctg tcagctcctt tccgggactt tcgctttccc cctccctatt   3300

gccacggcgg aactcatcgc cgcctgcctt gcccgctgct ggacaggggc tcggctgttg   3360

ggcactgaca attccgtggt gttgtcgggg aaatcatcgt cctttccttg gctgctcgcc   3420

tgtgttgcca cctggattct gcgcgggacg tccttctgct acgtcccttc ggccctcaat   3480

ccagcggacc ttccttcccg cggcctgctg ccggctctgc ggcctcttcc gcgtcttcgc   3540

cttcgccctc agacgagtcg gatctccctt tgggccgcct ccccgcatcg atgatctttt   3600

tccctctgcc aaaaattatg ggacatcat gaagcccctt gagcatctga cttctggcta   3660

ataaaggaaa tttattttca ttgcaatagt gtgttggaat tttttgtgtc tctcactcg    3719
```